(12) United States Patent
Baidyaroy et al.

(10) Patent No.: US 9,068,235 B2
(45) Date of Patent: *Jun. 30, 2015

(54) FUNGAL STRAINS

(75) Inventors: Dipnath Baidyaroy, Fremont, CA (US); Ish Kumar Dhawan, Foster City, CA (US)

(73) Assignee: Codexis, Inc., Redwood City, CA (US)

(*) Notice: Subject to any disclaimer, the term of this patent is extended or adjusted under 35 U.S.C. 154(b) by 887 days.

This patent is subject to a terminal disclaimer.

(21) Appl. No.: 13/286,860

(22) Filed: Nov. 1, 2011

(65) Prior Publication Data

US 2012/0107880 A1    May 3, 2012

Related U.S. Application Data

(60) Provisional application No. 61/409,186, filed on Nov. 2, 2010, provisional application No. 61/409,217, filed on Nov. 2, 2010, provisional application No. 61/409,472, filed on Nov. 2, 2010, provisional application No. 61/409,480, filed on Nov. 2, 2010, provisional application No. 61/497,661, filed on Jun. 16, 2011.

(51) Int. Cl.

| C12N 1/20 | (2006.01) |
| C07H 21/04 | (2006.01) |
| C12Q 1/68 | (2006.01) |
| C12N 15/00 | (2006.01) |
| C12N 9/24 | (2006.01) |
| C12N 9/04 | (2006.01) |
| C12P 7/10 | (2006.01) |
| C12P 19/02 | (2006.01) |
| C12P 19/12 | (2006.01) |
| C12P 19/14 | (2006.01) |
| C12N 9/42 | (2006.01) |
| C13K 1/02 | (2006.01) |

(52) U.S. Cl.
CPC ....... *C12Y 101/99018* (2013.01); *C12N 9/0006* (2013.01); *C12P 7/10* (2013.01); *C12P 19/02* (2013.01); *C12P 19/12* (2013.01); *C12P 19/14* (2013.01); *C12P 2203/00* (2013.01); *C12N 9/2437* (2013.01); *Y02E 50/16* (2013.01); *C13K 1/02* (2013.01)

(58) Field of Classification Search
CPC ...... C12N 9/2402; C12N 1/14; C12N 145/09; C12N 2510/00
See application file for complete search history.

(56) References Cited

U.S. PATENT DOCUMENTS

| 4,356,196 A | 10/1982 | Hultquist |
| 4,451,648 A | 5/1984 | Parsons et al. |
| 4,461,648 A | 7/1984 | Foody |
| 4,556,430 A | 12/1985 | Converse et al. |
| 4,600,590 A | 7/1986 | Dale |
| 4,683,195 A | 7/1987 | Mullis et al. |
| 4,683,202 A | 7/1987 | Mullis |
| 4,965,188 A | 10/1990 | Mullis et al. |
| 5,037,663 A | 8/1991 | Dale |
| 5,171,592 A | 12/1992 | Holtzapple et al. |
| 5,811,381 A | 9/1998 | Emalfarb et al. |
| 5,939,544 A | 8/1999 | Karstens et al. |
| 6,015,707 A | 1/2000 | Emalfarb et al. |
| 6,090,595 A | 7/2000 | Foody et al. |
| 6,106,888 A | 8/2000 | Dale et al. |
| 6,117,679 A | 9/2000 | Stemmer |
| 6,176,176 B1 | 1/2001 | Dale et al. |
| 6,376,246 B1 | 4/2002 | Crameri et al. |
| 6,573,086 B1 | 6/2003 | Emalfrab et al. |
| 6,586,182 B1 | 7/2003 | Patten et al. |
| 6,933,133 B2 | 8/2005 | Alam et al. |
| 7,419,809 B2 | 9/2008 | Foody et al. |
| 7,465,791 B1 | 12/2008 | Hallberg et al. |
| 7,754,457 B2 | 7/2010 | Foody et al. |
| 7,883,872 B2 | 2/2011 | Gusakov et al. |
| 7,910,338 B2 | 3/2011 | Hennessey et al. |
| 7,932,063 B2 | 4/2011 | Dunson et al. |
| 7,998,713 B2 | 8/2011 | Dunson et al. |
| 2002/0164730 A1 | 11/2002 | Predices et al. |
| 2008/0104724 A1 | 5/2008 | Sticklen et al. |
| 2008/0194005 A1 | 8/2008 | Emalfarb et al. |
| 2008/0220990 A1 | 9/2008 | Fox |
| 2009/0099079 A1 | 4/2009 | Emalfarb et al. |
| 2009/0312196 A1 | 12/2009 | Colbeck et al. |

FOREIGN PATENT DOCUMENTS

| EP | 1482033 A1 | 12/2004 |
| WO | 98/15633 A1 | 4/1998 |
| WO | 2006/032282 A1 | 3/2006 |
| WO | 2006/110891 A2 | 10/2006 |
| WO | 2006/110901 A2 | 10/2006 |
| WO | 2008/073914 A2 | 6/2008 |
| WO | 2009/033071 A2 | 3/2009 |
| WO | 2009/045651 A2 | 4/2009 |
| WO | 2010/022511 A1 | 3/2010 |

(Continued)

OTHER PUBLICATIONS

Henriksson, G., et al., "A critical review of cellobiose dehydrogenases," Journal of Biotechnology, 78(2):93-113 [2000].

Subramaniam, S.S., et al., "Cloning and characterization of a thermostable cellobiose dehydrogenase from *Sporotrichum thermophile*," Archives of Biochemistry and Biophysics, 365(2):223-230 [1999].

Boisset, C., et al, "Imaging the Enzymatic Digestion of Bacterial Cellulose Ribbons Reveals the Endo Character of the Cellobiohydrolase Cel6A from Humicola insolens and Its Mode of Synergy with Cellobiohydrolase Cel7A," Appl Envir. Microbiol., 66:144-1452 [2000].

(Continued)

*Primary Examiner* — Yong Pak
(74) *Attorney, Agent, or Firm* — Codexis, Inc.

(57) ABSTRACT

The present invention provides improved fungal strains. In some embodiments, the improved fungal strains find use in hydrolyzing cellulosic material to glucose.

14 Claims, 2 Drawing Sheets

(56) References Cited

FOREIGN PATENT DOCUMENTS

| WO | 2010/080407 A2 | 7/2010 |
|---|---|---|
| WO | 2010/080532 A1 | 7/2010 |
| WO | 2011/066457 A2 | 6/2011 |
| WO | 2011/143632 A2 | 11/2011 |

OTHER PUBLICATIONS

Bhat, K.M., et al., "*Sporotrichum thermophile* Growth, Cellulose Degradation, and Cellulase Activity," Appl Envir. Microbiol., 53:2175-2182 [1987].

Rosgaard, L., et al., "Efficiency of new fungal cellulase systems in boosting enzymatic degradation of barley straw lignocellulose," Biotechnol Prog, 22(2):493-8 [2006].

Badhan, A.K., et al., "Production of multiple xylanolytic and cellulolytic enzymes by thermophilic fungus *Myceliophthora* sp. ImI 387099," Bioresour Technol, 98(3):504-10 [2007].

Adachi, K., et al., "Efficient gene identification and targeted gene disruption in the wheat blotch fungus *Mycosphaerella graminicola* using TAGKO," Curr Genet., 42:123-7 [2002].

Alizadeh, H., et al., "Pretreatment of switchgrass by ammonia fiber explosion (AFEX)," Appl. Biochem. Biotechnol., 121-124:1133-1141 [2005].

Altschul, S.F., et al., "Gapped BLAST and PSI-BLAST: a new generation of protein database search programs," Nucleic Acids Res., 25(17):3389-3402 (1997).

Awao, T., et al., "A new thermophilic species of *Myceliophthora*," Mycotaxon, 16(2):436-440 [1983].

Bailey, M.J, et al., "Interlaboratory testing of methods for assay of xylanase activity," J. Biotechnol., 23:257-270 [1992].

Ballesteros, I., et al., "Ethanol production from steam-explosion pretreated wheat straw," Appl. Biochem. Biotechnol., 129-132: 496-508 [2006].

Biely, P., et al., "Recent progress in the assays of xylanolytic enzymes," J. Sci. Food Agr. 86:1636-1647 [2006].

Cannon, P.F., "Name changes in fungi of microbiological, industrial and medical importance. Part 4," Mycopathol., 111:75-83 [1990].

Cavener, D.R., "GMC Oxidoreductases: A Newly Defined Family of Homologous Proteins with Diverse Catalytic Activities," J. Mol. Biol., 223:811-814 [1992].

Chandra, R.P., et al., "Substrate pretreatment: the key to effective enzymatic hydrolysis of lignocellulosics?" Adv. Biochem. Engin./Biotechnol., 108: 67-93 [2007].

Chang, X.-B., et al., "Modification of DNA ends can decrease end joining relative to homologous recombination in mammalian cells," Proc. Natl. Acad. Sci. USA, 84:4959-4963 [1987].

Chundawat, S.P.S., et al., "Effect of particle size based separation of milled corn stover on AFEX pretreatment and enzymatic digestibility," Biotechnol. Bioeng., 96(2):219-231 [2007].

Combier, J.-P., et al., "*Agrobacterium tumefaciens*-mediated transformation as a tool for insertional mutagenesis in the symbiotic ectomycorrhizal fungus *Hebeloma cylindrosporum*," FEMS Microbiol. Lett., 220:141-8 [2003].

Davidson, R.C., et al., "Gene disruption by biolistic transformation in serotype D strains of *Cryptococcus neoformans*," Fung. Genet. Biol., 29:38-48 [2000].

Davidson, R.C., et al., "A PCR-based strategy to generate integrative targeting alleles with large regions of homology," Microbiol., 148:2607-2615 [2002].

Dayhoff, M.O. et al., in Atlas of Protein Sequence and Structure, "A model of evolutionary change in proteins," vol. 5, Suppl. 3, Natl. Biomed. Res. Round, Washington D.C. [1978], pp. 345-352.

De Vries, R.P., et al., "aguA, the Gene Encoding an Extracellular alpha-Glucuronidase from *Aspergillus tubingensis*, Is Specifically Induced on Xylose and Not on Glucuronic Acid," J. Bacteriol., 180(2):243-249 [1998].

Duff, S.J.B., et al., "Bioconversion of Forest Products Industry Waste Cellulosics to Fuel Ethanol: A Review," Biores. Technol., 55: 1-33 [1996].

Dynan, W.S., et al., "Control of eukaryotic messenger RNA synthesis by sequence-specific DNA-binding proteins," Nature, 316:774-78 [1985].

Fab, S.H., et al., "Influence of Specific Signal Peptide Mutations on the Expression and Secretion of the alpha-Amylase Inhibitor Tendamistat in *Streptomyces lividans*," J. Biol. Chem., 271:15244-15252 [1996].

Fire, A., et al., "Potent and specific genetic interference by double-stranded RNA in *Caenorhabditis elegans*," Nature, 391:806-11 [1998].

Firon, A., et al., "Identification of Essential Genes in the Human Fungal Pathogen *Aspergillus fumigatus* by Transposon Mutagenesis," Eukaryot. Cell, 2:247-55 [2003].

Florea, S., et al., "Elimination of marker genes from transformed filamentous fungi by unselected transient transfection with a Cre-expressing plasmid," Fung. Genet. Biol., 46:721-730 [2009].

Foreman, P.K., et al., "Transcriptional Regulation of Biomass-degrading Enzymes in the Filamentous Fungus *Trichoderma reesei*," J. Biol. Chem., 278(34):31988-31997 [2003].

Galbe, M. et al., "Pretreatment of lignocellulosic materials for efficient bioethanol production," Adv. Biochem. Engin./Biotechnol., 108: 41-65 [2007].

Galbe, M., et al., "A review of the production of ethanol from softwood," Appl. Microbiol. Biotechnol., 59:618-628 [2002].

Garg, A.K., "An addition to the genus *Chrysosporium* Corda," Mycopathol., 30: 3-4 [1966].

Ghose, T.K., "Measurement of Cellulase Activities," Pure & Appl. Chem., 59(2):257-268 [1987].

Ghosh, P., et al., "Physicochemical and Biological Treatments for Enzymatic/Microbial Conversion of Lignocellulosic Biomass," Adv. Appl. Microbiol., 39:295-333 [1993].

Glenn, J.K., et al., "Mn(II) Oxidation Is the Principal Function of the Extracellular Mn-Peroxidase from *Phanerochaete chrysosporium*'," Arch. Biochem. Biophys., 251(2):688-696 [1986].

Gollapalli, L.E., et al., "Predicting digestibility of ammonia fiber explosion (AFEX)-treated rice straw," Appl. Biochem. Biotechnol., 98-100:23-35 [2002].

Gong, C.S., et al., "Ethanol production from renewable resources," Adv. Biochem. Engin./Biotechnol., 65: 207-241 [1999].

Guarro, J., et al., "*Myceliophthora vellerea* (*Chrysosporium asperatum*) anamorph of *Ctenomyces serratus*," Mycotaxon, 23: 419-427 [1985].

Hai, P.Q., et al., "Synergistic Effects of Cellobiose Dehydrogenase, Cellulases, and Beta-Glucosidase from *Irpex lacteus* in the Degradation of Various Types of Cellulose" J. Appl. Glycosci., 49:9-17 [2002].

Hallberg, B.M., et al., "Mechanism of the Reductive Half-reaction in Cellobiose Dehydrogenase", J. Biol. Chem., 278(9): 7160-7166 [2003].

Harris, P.V., et al., "Stimulation of lignocellulosic biomass hydrolysis by proteins of glycoside hydrolase family 61: structure and function of a large, enigmatic family," Biochem., 49(15):3305-16 [2010].

Harvey, P.J., et al., "Veratryl alcohol as a mediator and the role of radical cations in lignin biodegradation by *Phanerochaete chrysosporium*," FEBS Lett., 195(1,2):242-246 [1986].

Hendriks, A.T.W.M., et al., "Pretreatments to enhance the digestibility of lignocellulosic biomass," Biores. Technol., 100:10-18 [2009].

Henikoff, S., et al. "Amino acid substitution matrices from protein blocks," Proc. Natl. Acad. Sci. USA, 89:10915-10919 (1992).

Henriksson, G. et al, "Substrate specificity of cellobiose dehydrogenase from *Phanerochaete chrysosporium*," . Biochim. Biophys. Acta., 1383: 48-54 [1998].

Herrmann, M.C., et al., "The beta-D-xylosidase of *Trichoderma reesei* is a multifunctional beta-D-xylan xylohydrolase," Biochem. J., 321:375-381 [1997].

Horton, R.M., et al., "Gene splicing by overlap extension," Meth. Enzymol., 217:270-279 [1993].

Hsu, T.-A., "Pretreatment of Biomass," in Handbook on Bioethanol: Production and Utilization (Wyman, ed.), Taylor & Francis, Washington, D.C., pp. 179-212 [1996].=.

Igarashi, K., et al., "Cellobiose dehydrogenase enhances Phanerochaete chrysosporium cellobiohydrolase I activity by relieving product inhibition," Eur. J. Biochem., 253: 101-106 [1998].

(56) References Cited

OTHER PUBLICATIONS

Kadotani, N., et al. "RNA silencing in the phytopathogenic fungus *Magnaporthe oryzae*," Mol. Plant Microbe Interact., 16(9):769-76 [2003].
Kotiranta, P., et al., "Adsorption and activity of Trichoderma reesei cellobiohydrolase I, endoglucanase II, and the corresponding core proteins on steam pretreated willow," Appl. Biochem. Biotechnol., 81: 81-90 [1999].
Kurabi, A., et al., "Enzymatic hydrolysis of steam-exploded and ethanol organosolv-pretreated Douglas-Firby novel and commercial fungal cellulases," Appl. Biochem. Biotechnol., 121-124:219-230 [2005].
Lee, Y.Y., et al., "Dilute-Acid Hydrolysis of Lignocellulosic Biomass," Adv. Biochem. Eng. Biotechnol., 65: 93-115 [1999].
Lever, M., "A New Reaction for Calorimetric Determination of Carbohydrates," Anal. Biochem., 47:273-279 [1972].
Li, J., et al., "Crystal structure of cholesterol oxidase complexed with a steroid substrate: implications for flavin adenine dinucleotide dependent alcohol oxidases," Biochem., 32(43):11507-15 [1993].
Lynd, L.R., et al., "Large-Scale Fuel Ethanol from Lignocellulose," Appl. Biochem. Biotechnol., 24/25: 695-719 [1990].
Mansfield, S.D., et al., "Cellobiose Dehydrogenase, an Active Agent in Cellulose Depolymerization," Appl. Environ. Microbiol., 63(10): 3804-3809 [1997].
Martin, C., et al., "Investigation of cellulose convertibility and ethanolic fermentation of sugarcane bagasse pretreated by wet oxidation and steam explosion," J. Chem. Technol. Biotechnol., 81:1669-1677 [2006].
Melander, C., et al., "New approaches to the analysis of enzymatically hydrolyzed methyl cellulose. Part 2. Comparison of various enzyme preparations," Biomacromol., 7(5):1410-1421 [2006].
Miyagishi, M., et al., "U6 promoter-driven siRNAs with four uridine 3' overhangs efficiently suppress targeted gene expression in mammalian cells," Nat. Biotechnol., 19:497-500 [2002].
Mosier, N., et al., "Features of promising technologies for pretreatment of lignocellulosic biomass," Biores. Technol., 96: 673-686 [2005].
Mosier, N., et al., "Reaction Kinetics, Molecular Action, and Mechanisms of Cellulolytic Proteins," Advances in Biochemical Engineering/Biotechnology, 65:23-40 [1999].
Moustafa, A.F., et al., "*Thielavia aegyptiaca*, a New Thermotolerant Ascomycete from Egyptian Soils," Persoonia, 14(Part2):173-175[1990].
Ngiam, C., et al., "Characterization of a Foldase, Protein Disulfide Isomerase A, in the Protein Secretory Pathway of *Aspergillus niger*," Appl Environ. Microbiol., 66(2):775-82 [2000].
Olsson, L., et al., "Fermentation of lignocellulosic hydrolysates for ethanol production," Enz. Microb. Tech., 18:312-331 [1996].
Paddison, P.J., et al., "Short hairpin RNAs (shRNAs) induce sequence-specific silencing in mammalian cells,"Genes Dev.16:948-958 [2002].
Palonen, H., et al., "Evaluation of Wet Oxidation Pretreatment for Enzymatic Hydrolysis of Softwood," Appl. Biochem. Biotechnol., 117:1-17 [2004].
Pan, X., et al., "Bioconversion of Hybrid Poplar to Ethanol and Co-Products Using an Organosolv Fractionation Process: Optimization of Process Yields," Biotechnol. Bioeng., 94(5):851-861 [2006].
Pan, X., et al., "Biorefining of Softwoods Using Ethanol Organosolv Pulping: Preliminary Evaluation of Process Streams for Manufacture of Fuel-Grade Ethanol and Co-Products," Biotechnol. Bioeng., 90(4):473-481 [2005].
Rakotomanga, S., et al., "Simultaneous determination of gluconolactone, galactonolactone and galactitol in urine by reversed-phase liquid chromatography: application to galactosemia," J. Chromatog. B., 570:277-284 [1991].
Rothstein, R.J., "One-Step Gene Disruption in Yeast," Meth. Enzymol., 101:202-211 [1983].
Rotsaert, F.A., et al., "Site-Directed Mutagenesis of the Heme Axial Ligands in the Hemoflavoenzyme Cellobiose Dehydrogenase," Arch. Biochem. Biophys., 390(2):206-14 [2001].
Rotsaert, F.A.J., et al., "Role of the flavin domain residues, His689 and Asn732, in the catalytic mechanism of cellobiose dehydrogenase from phanerochaete chrysosporium," Biochem., 42:4049-4056 [2003].
Salheimo, M., et al., "Swollenin, a *Trichoderma reesei* protein with sequence similarity to the plant expansins, exhibits disruption activity on cellulosic materials," Eur. J. Biochem., 269:4202-4211 [2002].
Sassner, P., et al., "Bioethanol production based on simultaneous saccharification and fermentation of steam-pretreated Salix at high dry-matter content," Enzyme Microb. Technol., 39:756-762 [2006].
Schell, D.J., et al., "A bioethanol process development unit: initial operating experiences and results with a corn fiber feedstock," Biores. Technol., 91:179-188 [2004].
Schell, D.J., et al., "Dilute—Sulfuric Acid Pretreatment of Corn Stover in Pilot-Scale Reactor," Appl. Biochem. Biotechnol., 105-108:69-85 [2003].
Schmidt, A.S., et al. "Optimization of Wet Oxidation Pretreatment of Wheat Straw," Biores. Technol., 64:139-151 [1998].
Schou, C., et al., "Characterization of a cellobiose dehydrogenase from Humicola insolens," Biochem. J., 330:565-571 [1998].
Spanikova, S., et al., "Glucuronoyl esterase—Novel carbohydrate esterase produced by *Schizophyllum commune*," FEBS Lett., 580:4597-4601 [2006].
Taherzadeh, M.J., et al., "Pretreatment of Lignocellulosic Wastes to Improve Ethanol and Biogas Production: A Review," Int. J. Mol. Sci., 9:1621-1651 [2008].
Teeri, T.T., "Crystalline cellulose degradation: new insight into the function of cellobiohydrolases," Tr. Biotechnol., 15:160-167 [1997].
Teeri, T.T., et al., "*Trichoderma reesei* cellobiohydrolases: why so efficient on crystalline cellulose?" Biochem. Soc. Trans., 26:173-178 [1998].
Teymouri, F., et al., "Optimization of the ammonia fiber explosion (AFEX) treatment parameters for enzymatic hydrolysis of corn stover," Biores. Technol., 96:2014-2018 [2005].
Thon, M.R., et al., "Restriction Enzyme-Mediated Integration Used to Produce Pathogenicity Mutants of *Colletotrichum graminicola*," Mol. Plant Microbe Interact., 13(12):1356-65 [2000].
Trinder, P., "Determination of glucose in blood using glucose oxidase with an alternative oxygen acceptor," Ann. Clin. Biochem., 6:24-27 [1969].
Upadhyay, J.M., et al., "A new variety of thermophilic mold, *Thermoascus aurantiacus* var. levisporus," Mycopathol., 87:71-80 [1984].
Vallander, L., et al., "Production of Ethanol from Lignocellulosic Materials: State of the Art," Adv. Biochem. Eng./Biotechnol., 42:63-95 [1990].
Van Tilbeurgh, H., et al., "Detection and differentiation of cellulase components using low molecular mass fluorogenic substrates," FEBS Lett., 187(2):283-288 [1985].
Van Tilbeurgh, H., et al., "The use of 4-methylumbelliferyl and other chromophoric glycosides in the study of cellulolytic enzymes," FEBS Lett., 149:152-156 [1982].
Varga, E., et al., "High Solid Simultaneous Saccharification and Fermentation of Wet Oxidized Corn Stover to Ethanol," Biotechnol. Bioeng., 88(5):567-574 [2004].
Varga, E. et al., "Optimization of Steam Pretreatment of Corn Stover to Enhance Enzymatic Digestibility," Appl. Biochem. Biotechnol., 113-116:509-523 [2004].
Venturi, L.L., et al., "Extracellular Beta-D-glucosidase from *Chaetomium thermophilum* var. coprophilum: production, purification and some biochemical properties," J. Basic Microbiol., 42: 55-66 [2002].
Von Klopotek, A., "Revision der thermophilen Sporotrichum-Arten: *Chrysosporium thermophilum* (Apinis) comb. nov. und *Chrysosporium fergusii* spec. nov. = status conidialis von *Corynascus thermophilus* (Fergus und Sinden) comb. nov.," Arch. Microbiol., 98:365-369 [1974].
Wang, Y. et al.' "Agrobacterium-mediated gene disruption using split-marker in *Grosmannia clavigera*, a mountain pine beetle associated pathogen," Curr. Genet., 56:297-307 [2010].
Weil, J., et al., "Pretreatment of Yellow Poplar Sawdust by Pressure Cooking in Water," Appl. Biochem. Biotechnol., 68: 21-40 [1997].

(56) References Cited

OTHER PUBLICATIONS

Wiselogel, A., et al., "Biomass Feedstock Resources and Composition" in Handbook on Bioethanol, (Wyman, ed.), pp. 105-118, Taylor & Francis, Washington D.C. [1995].

Wyman, C.E., "Ethanol from Lignocellulosic Biomass: Technology, Economics, and Opportunities," Biores. Technol., 50: 3-16 [1994].

Wyman, C.E., et al., "Coordinated development of leading biomass pretreatment technologies," Biores. Technol., 96:1959-1966 [2005].

Yang, B., et al., "Pretreatment: the key to unlocking low-cost cellulosic ethanol" Biofuels Bioprod. Bioref.-Biofpr. 2: 26-40 [2008].

Zhang, Y.-H., et al., "Outlook for cellulase improvement: Screening and selection strategies," Biotechnol. Adv., 24:452-481 [2006].

Zrenner, R., et al., "Analysis of the expression of potato uridinediphosphate-glucose pyrophosphorylase and its inhibition by antisense RNA" Planta, 190:247-52 [1993].

Dumonceaux, T., et al., "Cellobiose dehydrogenase is essential for wood invasion and nonessential for kraft pulp delignification by Trametes versicolor," Enzyme and Microbial Technology, 29:478-489 [2001].

FIGURE 1.

(M. thermophila CDH1)

ATGAGGACCTCCTCTCGTTTAATCGGTGCCCTTGCGGCGGCACTCTTGCCGTCTGCCCTTGCGCAGAACAACGCGCCGGTAAC
CTTCACCGACCCGGACTCGGGCATTACCTTCAACACGTGGGGTCTCGCCGAGGATTCTCCCCAGACTAAGGGCGGTTTCACTTT
TGGTGTTGCTCTGCCCTCTGATGCCCTCACGACAGACGCCAAGGAGTTCATCGGTTACTTGAAATGCGCGAGGAACGATGAGA
GCGGTTGGTGCGGTGTCTCCCTGGGCGGCCCATGACCAACTCGCTCCTCATCGCGGCCTGGCCCCACGAGGACACCGTCTA
CACCTCTCTCCGCTTCGCCACCGGCTATGCCATGCCGGATGTCTACCAGGGGGACGCCGAGATCACCCAGGTCTCCTCCTCTG
TCAACTCGACGCACTTCAGCCTCATCTTCAGGTGCGAGAACTGCCTGCAATGGAGTCAAAGCGGCGCCACCGGCGGTGCCTCC
ACCTCGAACGGCGTGTTGGTCCTCGGCTGGGTCCAGGCATTCGCCGACCCCGGCAACCCGACCTGGCCCGACCAGATCACCC
TCGAGCAGCACGACAACGGCATGGGTATCTGGGGTGCCCAGCTCAACTCCGACGCCGCCAGCCCGTCCTACACCGAGTGGGC
CGCCCAGGCGACCAAGACCGTCACGGGTGACTGCGGCGGTCCCACCGAGACCTCTGTCGTCGGTGTCCCCGTTCCGACGGGC
GTCTCGTTCGATTACATCGTCGTGGGCGGCGGTGCCGGTGGCATCCCCGCCGCCGACAAGCTCAGCGAGGCCGGCAAGAGTG
TGCTGCTCATCGAGAAGGGCTTTGCCTCGACCGCCAACACCGGAGGCACTCTCGGCCCCGAGTGGCTCGAGGGCCACGACCT
TACCCGCTTTGACGTGCCGGGTCTGTGCAACCAGATCTGGGTTGACTCCAAGGGGATCGCTTGCGAGGATACCGACCAGATGG
CTGGCTGTGTCCTCGGCGGCGGGTACCGCCGTGAATGCCGGCCTGTGGTTCAAGCCCTACTCGCTCGACTGGGACTACCTCTTC
CCTAGTGGTTGGAAGTACAAAGACGTGCAGCCGGCCATCAACCGCGCGGTCTCGCGCATCCGGGGCACCGATGCTCCCTCGAC
CGACGGCAAGCGCTACTACCAACAGGGGTTCGACGTCGTCTCCAAGGGCCTGGCCGGCGGCGGCGGCTGGACCTGGTCACGGCC
AATAACGCGCCAGACAAGAAGAACCGCACCTTCTCGCATGCCGCCCTTCATGTTCGCCGGCGGCGAGCGCAACGGCCCGCTGG
GCACCTACTTCCAGACCGCCAAGAAGCGCAGGAACTTCAAGCTCTGGCTCAACACGTCGGTCAAGCGCGTGATCCGCCAGGGC
GGCCACATCACCGGCGTCGAGGTCGAGCCGTTCCGCGACGGCGGTTACCAAGGCATCGTCCCCGTCACCAAGGTTACGGGCC
GCGTCATCCTCTCTGCCGGTACCTTTGGCAGTGCAAAGATCCTGCTGAGGAGCGGTATCGGTCCGAACGATCAGCTGCAGGTT
GTCGCGGCCTCGGAGAAGGATGGCCCTACCATGATCAGCAACTCGTCCTGGATCAACCTGCCTGTCGGCTACAACCTGGATGA
CCACCTCAACACCGACACTGTCATCTCGCACCCCGACGTCGTGTTCTACGACTTCTACGAGGCGTGGGACAATCCCATCCAGTC
TGACAAGGACAGCTACCTCAACTCGCGCAGGGGCATCCTCGCCCAAGCGGGTCGCAACATTGGGCCTATGTTCTGGGAAGAGA
TCAAGGGTGCGGACGGCATTGTTCGCCAGCTCCAGTGGACTGCCCGTGTCGAGGGCAGCCTGGGTGCCCCAACGGCAAGAC
CATGACCATGTCGCAGTACCTCGGTCGTGGTGCCACCTCGCGCGGGCCGCATGACCATCACCCCGTCCCTGACAACTGTCGTCT
CGGACGTGCCGTACCTCAAGGACCCCAACGACAAGGAGGCCGTCATCCAGGGCATCATCAACCTGCAGAACGCCCTCAAGAAC
GTCGCCAACCTGACCTGGCTGCTTCCCCAACTCGACCCATCACGCCGCGCCAATACGTTGACAGCATGGTCGTCTCCCCGAGCAA
CCGGCGCTCCAACCACTGGATGGGCACCAACAAGATCGGCACCGACGACGGGGCGCAAGGGCGGCTCCGCCGTCGTCGACCTC
AACACCAAGGTCTACGGCACCGACAACCTCTTCGTCATCGACGCCTCCATCTTCGCCGGGGTGCCCACCACCAACCCCACCTCG
TACATCGTGACGGCGTCGGAGCACGCCTCGGCGCGCATCCTCGCCCTGCCCGACCTCACGCCCGTCCCCAAGTACGGGCAGT
GCGGCGGCCGCGAATGGAGCGGCAGCTTCGTCTGCGCCGACGGCTCCACGTGCCAGATGCAG
AACGAGTGGTACTCGCAGTGCTTGTGA (SEQ. ID NO:1)

MRTSSRLIGALAAALLPSALAQNNAPVTFTDPDSGITFNTWGLAEDSPQTKGGFTFGVALPSDALTTDAKEFIGYLKCARNDESGWCG
VSLGGPMTNSLLIAAWPHEDTVYTSLRFATGYAMPDVYQGDAEITQVSSSVNSTHFSLIFRCENCLQWSQSGATGGASTSNGVLVLG
WVQAFADPGNPTCPDQITLEQHDNGMGIWGAQLNSDAASPSYTEWAAQATKTVTGDCGGPTETSVVGVPVPTGVSFDYIVVGGGA
GGIPAADKLSEAGKSVLLIEKGFASTANTGGTLGPEWLEGHDLTRFDVPGLCNQIWVDSKGIACEDTDQMAGCVLGGGTAVNAGLWF
KPYSLDWDYLFPSGWKYKDVQPAINRALSRIPGTDAPSTDGKRYYQQGFDVLSKGLAGGGWTSVTANNAPDKKNRTFSHAPFMFAG
GERNGPLGTYFQTAKKRSNFKLWLNTSVKRVIRQGGHITGVEVEPFRDGGYQGIVPVTKVTGRVILSAGTFGSAKILLRSGIGPNDQL
QVVAASEKDGPTMISNSSWINLPVGYNLDDHLNTDTVISHPDVVFYDFYEAWDNPIQSDKDSYLNSRTGILAQAAPNIGPMFWEEIKG
ADGIVRQLQWTARVEGSLGAPNGKTMTMSQYLGRGATSRGRMTITPSLTTVVSDVPYLKDPNDKEAVIQGIINLQNALKNVANLTWLF
PNSTITPRQYVDSMVVSPSNRRSNHWMGTNKIGTDDGRKGGSAVVDLNTKVYGTDNLFVIDASIFPGVPTTNPTSYIVTASEHASARIL
ALPDLTPVPKYGQCGGREWSGSFVCADGSTCQMQNEWYSQCL* (SEQ ID NO:2)

SEQUENCE LISTING

```
<160> NUMBER OF SEQ ID NOS: 21

<210> SEQ ID NO 1
<211> LENGTH: 2487
<212> TYPE: DNA
<213> ORGANISM: Myceliophthora thermophila

<400> SEQUENCE: 1
atgaggacct cctctcgttt aatcggtgcc cttgcggcgg cactcttgcc gtctgccctt      60
gcgcagaaca acgcgccggt aaccttcacc gacccggact cgggcattac cttcaacacg     120
tggggtctcg ccgaggattc tccccagact aagggcggtt tcacttttgg tgttgctctg     180
ccctctgatg ccctcacgac agacgccaag gagttcatcg gttacttgaa atgcgcgagg     240
aacgatgaga gcggttggtg cggtgtctcc ctgggcggcc ccatgaccaa ctcgctcctc     300
atcgcggcct ggccccacga ggacaccgtc tacacctctc tccgcttcgc caccggctat     360
gccatgccgg atgtctacca gggggacgcc gagatcaccc aggtctcctc ctctgtcaac     420
tcgacgcact tcagcctcat cttcaggtgc gagaactgcc tgcaatggag tcaaagcggc     480
gccaccggcg gtgcctccac ctcgaacggc gtgttggtcc tcggctgggt ccaggcattc     540
gccgaccccg gcaacccgac ctgccccgac cagatcaccc tcgagcagca cgacaacggc     600
atgggtatct ggggtgccca gctcaactcc gacgccgcca gcccgtccta caccgagtgg     660
gccgcccagg ccaccaagac cgtcacgggt gactgcggcg gtcccaccga gacctctgtc     720
gtcggtgtcc ccgttccgac gggcgtctcg ttcgattaca tcgtcgtggg cggcggtgcc     780
```

```
ggtggcatcc ccgccgccga caagctcagc gaggccggca agagtgtgct gctcatcgag    840
aagggctttg cctcgaccgc caacaccgga ggcactctcg ccccgagtg gctcgagggc     900
cacgacctta cccgctttga cgtgccgggt ctgtgcaacc agatctgggt tgactccaag    960
gggatcgctt gcgaggatac cgaccagatg gctggctgtg tcctcggcgg cggtaccgcc   1020
gtgaatgccg gcctgtggtt caagccctac tcgctcgact gggactacct cttccctagt   1080
ggttggaagt acaaagacgt ccagccggcc atcaaccgcg ccctctcgcg catcccgggc   1140
accgatgctc cctcgaccga cggcaagcgc tactaccaac agggcttcga cgtcctctcc   1200
aagggcctgg ccggcggcgg ctggacctcg gtcacggcca ataacgcgcc agacaagaag   1260
aaccgcacct tctcccatgc ccccttcatg ttcgccggcg gcgagcgcaa cggcccgctg   1320
ggcacctact tccagaccgc caagaagcgc agcaacttca agctctggct caacacgtcg   1380
gtcaagcgcg tcatccgcca gggcggccac atcaccggcg tcgaggtcga gccgttccgc   1440
gacggcggtt accaaggcat cgtccccgtc accaaggtta cgggccgcgt catcctctct   1500
gccggtacct ttggcagtgc aaagatcctg ctgaggagcg tatcggtcc gaacgatcag    1560
ctgcaggttg tcgcggcctc ggagaaggat ggccctacca tgatcagcaa ctcgtcctgg   1620
atcaacctgc ctgtcggcta aacctggat gaccacctca acaccgacac tgtcatctcc    1680
caccccgacg tcgtgttcta cgacttctac gaggcgtggg acaatcccat ccagtctgac   1740
aaggacagct acctcaactc gcgcacgggc atcctcgccc aagccgctcc caacattggg   1800
cctatgttct gggaagagat caagggtgcg gacggcattg ttcgccagct ccagtggact   1860
gcccgtgtcg agggcagcct gggtgccccc aacggcaaga ccatgaccat gtcgcagtac   1920
ctcggtcgtg gtgccaccct cgcgcggccg catgaccatc accctgtccct gacaactgtc   1980
gtctcggacg tgcccacct caaggacccc aacgacaagg aggccgtcat ccagggcatc    2040
atcaacctgc agaacgccct caagaacgtc gccaacctga cctggctctt ccccaactcg   2100
accatcacgc cgccgccaata cgttgacagc atggtcgtct ccccgagcaa ccggcgctcc   2160
aaccactgga tgggcaccaa caagatcggc accgacgacg ggcgcaaggg cggctccgcc   2220
gtcgtcgacc tcaacaccaa ggtctacggc accgacaacc tcttcgtcat cgacgcctcc   2280
atcttccccg gcgtgcccac caccaacccc acctcgtaca tcgtgacggc gtcggagcac   2340
gcctcggccc gcatcctcgc cctgcccgac ctcacgcccg tccccaagta cgggcagtgc   2400
ggcggccgcg aatggagcgg cagcttcgtc tgcgccgacg gctccacgtg ccagatgcag   2460
aacgagtggt actcgcagtg cttgtga                                        2487
```

<210> SEQ ID NO 2
<211> LENGTH: 828
<212> TYPE: PRT
<213> ORGANISM: Myceliophthora thermophila

<400> SEQUENCE: 2

Met Arg Thr Ser Ser Arg Leu Ile Gly Ala Leu Ala Ala Ala Leu Leu
1               5                   10                  15

Pro Ser Ala Leu Ala Gln Asn Asn Ala Pro Val Thr Phe Thr Asp Pro
            20                  25                  30

Asp Ser Gly Ile Thr Phe Asn Thr Trp Gly Leu Ala Glu Asp Ser Pro
        35                  40                  45

Gln Thr Lys Gly Gly Phe Thr Phe Gly Val Ala Leu Pro Ser Asp Ala
    50                  55                  60

Leu Thr Thr Asp Ala Lys Glu Phe Ile Gly Tyr Leu Lys Cys Ala Arg

```
                65                  70                  75                  80
Asn Asp Glu Ser Gly Trp Cys Gly Val Ser Leu Gly Pro Met Thr
                        85                  90                  95

Asn Ser Leu Leu Ile Ala Ala Trp Pro His Glu Asp Thr Val Tyr Thr
            100                 105                 110

Ser Leu Arg Phe Ala Thr Gly Tyr Ala Met Pro Asp Val Tyr Gln Gly
            115                 120                 125

Asp Ala Glu Ile Thr Gln Val Ser Ser Val Asn Ser Thr His Phe
            130                 135                 140

Ser Leu Ile Phe Arg Cys Glu Asn Cys Leu Gln Trp Ser Gln Ser Gly
145                 150                 155                 160

Ala Thr Gly Gly Ala Ser Thr Ser Asn Gly Val Leu Val Leu Gly Trp
                165                 170                 175

Val Gln Ala Phe Ala Asp Pro Gly Asn Pro Thr Cys Pro Asp Gln Ile
                180                 185                 190

Thr Leu Glu Gln His Asp Asn Gly Met Gly Ile Trp Gly Ala Gln Leu
                195                 200                 205

Asn Ser Asp Ala Ala Ser Pro Ser Tyr Thr Glu Trp Ala Ala Gln Ala
            210                 215                 220

Thr Lys Thr Val Thr Gly Asp Cys Gly Gly Pro Thr Glu Thr Ser Val
225                 230                 235                 240

Val Gly Val Pro Val Pro Thr Gly Val Ser Phe Asp Tyr Ile Val Val
                245                 250                 255

Gly Gly Gly Ala Gly Gly Ile Pro Ala Ala Asp Lys Leu Ser Glu Ala
                260                 265                 270

Gly Lys Ser Val Leu Leu Ile Glu Lys Gly Phe Ala Ser Thr Ala Asn
            275                 280                 285

Thr Gly Gly Thr Leu Gly Pro Glu Trp Leu Glu Gly His Asp Leu Thr
            290                 295                 300

Arg Phe Asp Val Pro Gly Leu Cys Asn Gln Ile Trp Val Asp Ser Lys
305                 310                 315                 320

Gly Ile Ala Cys Glu Asp Thr Asp Gln Met Ala Gly Cys Val Leu Gly
                325                 330                 335

Gly Gly Thr Ala Val Asn Ala Gly Leu Trp Phe Lys Pro Tyr Ser Leu
            340                 345                 350

Asp Trp Asp Tyr Leu Phe Pro Ser Gly Trp Lys Tyr Lys Asp Val Gln
            355                 360                 365

Pro Ala Ile Asn Arg Ala Leu Ser Arg Ile Pro Gly Thr Asp Ala Pro
            370                 375                 380

Ser Thr Asp Gly Lys Arg Tyr Tyr Gln Gln Gly Phe Asp Val Leu Ser
385                 390                 395                 400

Lys Gly Leu Ala Gly Gly Gly Trp Thr Ser Val Thr Ala Asn Asn Ala
                405                 410                 415

Pro Asp Lys Lys Asn Arg Thr Phe Ser His Ala Pro Phe Met Phe Ala
            420                 425                 430

Gly Gly Glu Arg Asn Gly Pro Leu Gly Thr Tyr Phe Gln Thr Ala Lys
            435                 440                 445

Lys Arg Ser Asn Phe Lys Leu Trp Leu Asn Thr Ser Val Lys Arg Val
            450                 455                 460

Ile Arg Gln Gly Gly His Ile Thr Gly Val Glu Val Glu Pro Phe Arg
465                 470                 475                 480

Asp Gly Gly Tyr Gln Gly Ile Val Pro Val Thr Lys Val Thr Gly Arg
                485                 490                 495
```

Val Ile Leu Ser Ala Gly Thr Phe Gly Ser Ala Lys Ile Leu Leu Arg
                500                 505                 510

Ser Gly Ile Gly Pro Asn Asp Gln Leu Gln Val Val Ala Ala Ser Glu
                515                 520                 525

Lys Asp Gly Pro Thr Met Ile Ser Asn Ser Ser Trp Ile Asn Leu Pro
                530                 535                 540

Val Gly Tyr Asn Leu Asp Asp His Leu Asn Thr Asp Thr Val Ile Ser
545                 550                 555                 560

His Pro Asp Val Val Phe Tyr Asp Phe Tyr Glu Ala Trp Asp Asn Pro
                565                 570                 575

Ile Gln Ser Asp Lys Asp Ser Tyr Leu Asn Ser Arg Thr Gly Ile Leu
                580                 585                 590

Ala Gln Ala Ala Pro Asn Ile Gly Pro Met Phe Trp Glu Glu Ile Lys
                595                 600                 605

Gly Ala Asp Gly Ile Val Arg Gln Leu Gln Trp Thr Ala Arg Val Glu
                610                 615                 620

Gly Ser Leu Gly Ala Pro Asn Gly Lys Thr Met Thr Met Ser Gln Tyr
625                 630                 635                 640

Leu Gly Arg Gly Ala Thr Ser Arg Gly Arg Met Thr Ile Thr Pro Ser
                645                 650                 655

Leu Thr Thr Val Val Ser Asp Val Pro Tyr Leu Lys Asp Pro Asn Asp
                660                 665                 670

Lys Glu Ala Val Ile Gln Gly Ile Ile Asn Leu Gln Asn Ala Leu Lys
                675                 680                 685

Asn Val Ala Asn Leu Thr Trp Leu Phe Pro Asn Ser Thr Ile Thr Pro
                690                 695                 700

Arg Gln Tyr Val Asp Ser Met Val Val Ser Pro Ser Asn Arg Arg Ser
705                 710                 715                 720

Asn His Trp Met Gly Thr Asn Lys Ile Gly Thr Asp Asp Gly Arg Lys
                725                 730                 735

Gly Gly Ser Ala Val Val Asp Leu Asn Thr Lys Val Tyr Gly Thr Asp
                740                 745                 750

Asn Leu Phe Val Ile Asp Ala Ser Ile Phe Pro Gly Val Pro Thr Thr
                755                 760                 765

Asn Pro Thr Ser Tyr Ile Val Thr Ala Ser Glu His Ala Ser Ala Arg
                770                 775                 780

Ile Leu Ala Leu Pro Asp Leu Thr Pro Val Pro Lys Tyr Gly Gln Cys
785                 790                 795                 800

Gly Gly Arg Glu Trp Ser Gly Ser Phe Val Cys Ala Asp Gly Ser Thr
                805                 810                 815

Cys Gln Met Gln Asn Glu Trp Tyr Ser Gln Cys Leu
                820                 825

<210> SEQ ID NO 3
<211> LENGTH: 787
<212> TYPE: PRT
<213> ORGANISM: Myceliophthora thermophila

<400> SEQUENCE: 3

Met Lys Leu Leu Ser Arg Val Gly Ala Thr Ala Leu Ala Ala Thr Leu
1               5                   10                  15

Ser Leu Gln Gln Cys Ala Ala Gln Met Thr Glu Gly Thr Tyr Thr Asp
                20                  25                  30

Glu Ala Thr Gly Ile Gln Phe Lys Thr Trp Thr Ala Ser Glu Gly Ala

```
            35                  40                  45
Pro Phe Thr Phe Gly Leu Thr Leu Pro Ala Asp Ala Leu Glu Lys Asp
 50                  55                  60

Ala Thr Glu Tyr Ile Gly Leu Leu Arg Cys Gln Ile Thr Asp Pro Ala
 65                  70                  75                  80

Ser Pro Ser Trp Cys Gly Ile Ser His Gly Gln Ser Gly Gln Met Thr
                 85                  90                  95

Gln Ala Leu Leu Leu Val Ala Trp Ala Ser Glu Asp Thr Val Tyr Thr
                100                 105                 110

Ser Phe Arg Tyr Ala Thr Gly Tyr Thr Leu Pro Gly Leu Tyr Thr Gly
            115                 120                 125

Asp Ala Lys Leu Thr Gln Ile Ser Ser Val Ser Glu Asp Ser Phe
130                 135                 140

Glu Val Leu Phe Arg Cys Glu Asn Cys Phe Ser Trp Asp Gln Asp Gly
145                 150                 155                 160

Thr Lys Gly Asn Val Ser Thr Ser Asn Gly Asn Leu Val Leu Gly Arg
                165                 170                 175

Ala Ala Ala Lys Asp Gly Val Thr Gly Pro Thr Cys Pro Asp Thr Ala
                180                 185                 190

Glu Phe Gly Phe His Asp Asn Gly Phe Gly Gln Trp Gly Ala Val Leu
            195                 200                 205

Glu Gly Ala Thr Ser Asp Ser Tyr Glu Glu Trp Ala Lys Leu Ala Thr
            210                 215                 220

Thr Thr Pro Glu Thr Thr Cys Asp Gly Thr Gly Pro Gly Asp Lys Glu
225                 230                 235                 240

Cys Val Pro Ala Pro Glu Asp Thr Tyr Asp Tyr Ile Val Val Gly Ala
                245                 250                 255

Gly Ala Gly Gly Ile Thr Val Ala Asp Lys Leu Ser Glu Ala Gly His
                260                 265                 270

Lys Val Leu Leu Ile Glu Lys Gly Pro Pro Ser Thr Gly Leu Trp Asn
            275                 280                 285

Gly Thr Met Lys Pro Glu Trp Leu Glu Ser Asp Leu Thr Arg Phe
            290                 295                 300

Asp Val Pro Gly Leu Cys Asn Gln Ile Trp Val Asp Ser Ala Gly Ile
305                 310                 315                 320

Ala Cys Thr Asp Thr Asp Gln Met Ala Gly Cys Val Leu Gly Gly Gly
                325                 330                 335

Thr Ala Val Asn Ala Gly Leu Trp Trp Lys Pro His Pro Ala Asp Trp
                340                 345                 350

Asp Glu Asn Phe Pro Glu Gly Trp Lys Ser Ser Asp Leu Ala Asp Ala
            355                 360                 365

Thr Glu Arg Val Phe Lys Arg Ile Pro Gly Thr Ser His Pro Ser Gln
            370                 375                 380

Asp Gly Lys Leu Tyr Arg Gln Glu Gly Phe Glu Val Ile Ser Lys Gly
385                 390                 395                 400

Leu Ala Asn Ala Gly Trp Lys Glu Ile Ser Ala Asn Glu Ala Pro Ser
                405                 410                 415

Glu Lys Asn His Thr Tyr Ala His Thr Glu Phe Met Phe Ser Gly Gly
                420                 425                 430

Glu Arg Gly Gly Pro Leu Ala Thr Tyr Leu Ser Ala Ala Glu Arg
            435                 440                 445

Ser Asn Phe Asn Leu Trp Leu Asn Thr Ala Val Arg Arg Ala Val Arg
450                 455                 460
```

Ser Gly Ser Lys Val Thr Gly Val Glu Leu Glu Cys Leu Thr Asp Gly
465                 470                 475                 480

Gly Phe Ser Gly Thr Val Asn Leu Asn Glu Gly Gly Val Ile Phe
            485                 490                 495

Ser Ala Gly Ala Phe Gly Ser Ala Lys Leu Leu Leu Arg Ser Gly Ile
            500                 505                 510

Gly Pro Glu Asp Gln Leu Glu Ile Val Ala Ser Ser Lys Asp Gly Glu
            515                 520                 525

Thr Phe Thr Pro Lys Asp Glu Trp Ile Asn Leu Pro Val Gly His Asn
530                 535                 540

Leu Ile Asp His Leu Asn Thr Asp Leu Ile Ile Thr His Pro Asp Val
545                 550                 555                 560

Val Phe Tyr Asp Phe Tyr Ala Ala Trp Asp Glu Pro Ile Thr Glu Asp
            565                 570                 575

Lys Glu Ala Tyr Leu Asn Ser Arg Ser Gly Ile Leu Ala Gln Ala Ala
            580                 585                 590

Pro Asn Ile Gly Pro Met Met Trp Asp Gln Val Thr Pro Ser Asp Gly
            595                 600                 605

Ile Thr Arg Gln Phe Gln Trp Thr Cys Arg Val Glu Gly Asp Ser Ser
            610                 615                 620

Lys Thr Asn Ser Thr His Ala Met Thr Leu Ser Gln Tyr Leu Gly Arg
625                 630                 635                 640

Gly Val Val Ser Arg Gly Arg Met Gly Ile Thr Ser Gly Leu Ser Thr
            645                 650                 655

Thr Val Ala Glu His Pro Tyr Leu His Asn Asn Gly Asp Leu Glu Ala
            660                 665                 670

Val Ile Gln Gly Ile Gln Asn Val Val Asp Ala Leu Ser Gln Val Ala
            675                 680                 685

Asp Leu Glu Trp Val Leu Pro Pro Asp Gly Thr Val Ala Asp Tyr
690                 695                 700

Val Asn Ser Leu Ile Val Ser Pro Ala Asn Arg Arg Ala Asn His Trp
705                 710                 715                 720

Met Gly Thr Ala Lys Leu Gly Thr Asp Asp Gly Arg Ser Gly Gly Thr
            725                 730                 735

Ser Val Val Asp Leu Asp Thr Lys Val Tyr Gly Thr Asp Asn Leu Phe
            740                 745                 750

Val Val Asp Ala Ser Val Phe Pro Gly Met Ser Thr Gly Asn Pro Ser
            755                 760                 765

Ala Met Ile Val Ile Val Ala Glu Gln Ala Ala Gln Arg Ile Leu Ala
            770                 775                 780

Leu Arg Ser
785

<210> SEQ ID NO 4
<211> LENGTH: 623
<212> TYPE: PRT
<213> ORGANISM: Myceliophthora thermophila

<400> SEQUENCE: 4

Met Lys Phe Leu Arg Lys Ser Asp Arg Gly Ser Val Leu Gly Ser Thr
1               5                   10                  15

Leu Phe Ser Leu Ala Phe Leu Phe Tyr Ser Pro Pro Thr Ala Ala Gln
            20                  25                  30

Ser Pro Pro Pro Asp Gly Ala Val Tyr Asp Tyr Ile Val Ile Gly Ser

```
                35                  40                  45
Gly Pro Gly Gly Gly Val Val Gly Ala Asn Leu Ala Lys Ala Gly Tyr
 50                  55                  60

Ser Val Leu Leu Leu Glu Ala Gly Asp Asp Ser Pro Gly Ala Gly Phe
 65                  70                  75                  80

Gly Val Tyr Thr Pro Thr Val Thr Trp Asp Phe Tyr Val Lys His Tyr
                 85                  90                  95

Pro Glu Gly Asp Pro Arg Asp Asn Gln Tyr Ser His Leu Thr Trp Leu
            100                 105                 110

Thr Pro Asp Gly Arg Tyr Trp Val Gly Gln Ser Gly Ala Pro Glu Gly
        115                 120                 125

Ser Arg Leu Leu Gly Val Tyr Tyr Pro Arg Gly Ala Thr Leu Gly Gly
    130                 135                 140

Ser Ser Met Ile Asn Ala Met Val Val Trp Leu Pro Asn Asp Ser Asp
145                 150                 155                 160

Trp Asp Tyr His Ala Glu Val Thr Gly Asp Asp Ser Trp Arg Ala Glu
                165                 170                 175

Asn Met His Lys Ile Phe Gln Lys Ile Glu Lys Asn Asn Tyr Leu Pro
            180                 185                 190

Arg Gly Thr Ala Asn His Gly Phe Asp Gly Trp Phe Gln Thr Gln Met
        195                 200                 205

Gly Thr Met Val Gln Thr Asn Arg Thr Gly Pro Leu Gln Gly Asn Gly
    210                 215                 220

Val Met Thr Thr Tyr Ala Gln Asp Trp Asn Leu Thr Ile Pro Met Ser
225                 230                 235                 240

Asp Leu Leu Ile Arg Asp Pro Asn Glu Ile Gly Pro Asp Arg Asp Gln
                245                 250                 255

Thr Ser Ser Ile Tyr Gly Gln Val Ser His Gln Phe Ala Asn Gly Asn
            260                 265                 270

Arg Tyr Ser Ser Arg His Tyr Val Gln Asp Ala Val Ser Ser Gly Ala
        275                 280                 285

Asn Leu Thr Val Ser Leu Thr Ser Leu Ala Thr Arg Ile Leu Phe Asp
    290                 295                 300

Thr Val Thr Glu Pro Asp Ser Pro Arg Ala Thr Gly Val Glu Tyr Leu
305                 310                 315                 320

Phe Gly Lys Ser Leu Tyr Arg Gly Asp Arg Arg Ala Asp Gly Ala
                325                 330                 335

Ile Gly Val Asn Arg Thr Ala Val Ala Arg Arg Glu Val Ile Val Ser
            340                 345                 350

Gly Gly Ala Phe Asn Ser Pro Gln Leu Leu Leu Ser Gly Ile Gly
        355                 360                 365

Asn Ala Thr Glu Leu Glu Ala Leu Gly Ile Pro Val Ile Arg Asp Leu
    370                 375                 380

Pro Gly Val Gly Arg Asn Leu Met Asp Asn Gln Glu Met Pro Ile Val
385                 390                 395                 400

Gly Thr Gly Ser Pro Gly Gly Pro Gly Ala Val Ala Gly Val Ala
                405                 410                 415

Met Tyr Lys Thr Arg His Pro Ala His Gly Arg Asp Met Phe Leu
            420                 425                 430

Phe Gly Gly Pro Gly Phe Leu Phe Arg Gly Phe Trp Pro Asn Glu Ala
        435                 440                 445

Val His Leu Pro Asp Glu Pro Ala Gln Pro Val Tyr Gly Val Ser Met
    450                 455                 460
```

```
Val Lys Gly Ser Ser Val Asn Asn Gly Gly Trp Val Lys Leu Arg Ser
465                 470                 475                 480

Arg Asp Pro Thr Asp Thr Pro Glu Ile Asn Phe Asn His Tyr Ala Val
                485                 490                 495

Gly Ala Glu Tyr Asp Leu Glu Ala Val Lys Asp Thr Val Ala Trp Ile
            500                 505                 510

Arg Ser Val Tyr Arg Arg Val Gly Ile Ala Thr Val Glu Pro Pro Cys
        515                 520                 525

Ala Arg Gly Pro Asp Glu Asn Gly Tyr Cys Gly Glu Asp Glu Ala
    530                 535                 540

Trp Ile His Lys Gln Thr Phe Gly His His Pro Thr Ser Thr Asn Lys
545                 550                 555                 560

Ile Gly Ala Asp Asp Pro Thr Ala Val Leu Asp Ser Lys Phe Arg
                565                 570                 575

Val Arg Gly Val Arg Ala Leu Arg Val Val Asp Ala Ser Ala Phe Ala
            580                 585                 590

Arg Ile Pro Gly Val Phe Pro Val Val Ser Thr Phe Met Ile Ser Gln
        595                 600                 605

Lys Ala Ser Asp Asp Ile Leu Ala Glu Leu Ala Glu Ser Arg
    610                 615                 620

<210> SEQ ID NO 5
<211> LENGTH: 647
<212> TYPE: PRT
<213> ORGANISM: Myceliophthora thermophila

<400> SEQUENCE: 5

Met Gly Phe Leu Ala Ala Thr Leu Val Ser Cys Ala Ala Leu Ala Ser
1               5                   10                  15

Ala Ala Ser Ile Pro Arg Pro His Ala Lys Arg Gln Val Ser Gln Leu
                20                  25                  30

Arg Asp Asp Tyr Asp Phe Val Ile Val Gly Gly Gly Thr Ser Gly Leu
            35                  40                  45

Thr Val Ala Asp Arg Leu Thr Glu Ala Phe Pro Ala Lys Asn Val Leu
        50                  55                  60

Val Ile Glu Tyr Gly Asp Val His Tyr Ala Pro Gly Thr Phe Asp Pro
65              70                  75                  80

Pro Thr Asp Trp Ile Thr Pro Gln Pro Asp Ala Pro Ser Trp Ser
                85                  90                  95

Phe Asn Ser Leu Pro Asn Pro Asp Met Ala Asn Thr Thr Ala Phe Val
            100                 105                 110

Leu Ala Gly Gln Val Val Gly Gly Ser Ser Ala Val Asn Gly Met Phe
        115                 120                 125

Phe Asp Arg Ala Ser Arg His Asp Tyr Asp Ala Trp Thr Ala Val Gly
    130                 135                 140

Gly Ser Gly Phe Glu Gln Ser Ser His Lys Trp Asp Trp Glu Gly Leu
145                 150                 155                 160

Phe Pro Phe Phe Gln Lys Ser Val Thr Phe Thr Glu Pro Pro Ala Asp
                165                 170                 175

Ile Val Gln Lys Tyr His Tyr Thr Trp Asp Leu Ser Ala Tyr Gly Asn
            180                 185                 190

Gly Ser Thr Pro Ile Tyr Ser Ser Tyr Pro Val Phe Gln Trp Ala Asp
        195                 200                 205

Gln Pro Leu Leu Asn Gln Ala Trp Gln Glu Met Gly Ile Asn Pro Val
```

-continued

```
            210                 215                 220
Thr Glu Cys Ala Gly Gly Asp Lys Glu Gly Val Cys Trp Val Pro Ala
225                 230                 235                 240

Ser Gln His Pro Val Thr Ala Arg Arg Ser His Ala Gly Leu Gly His
                    245                 250                 255

Tyr Ala Asp Val Leu Pro Arg Ala Asn Tyr Asp Leu Leu Val Gln His
                260                 265                 270

Gln Val Val Arg Val Val Phe Pro Asn Gly Pro Ser His Gly Pro Pro
            275                 280                 285

Leu Val Glu Ala Arg Ser Leu Ala Asp Asn His Leu Phe Asn Val Thr
        290                 295                 300

Val Lys Gly Glu Val Ile Ile Ser Ala Gly Ala Leu His Thr Pro Thr
305                 310                 315                 320

Val Leu Gln Arg Ser Gly Ile Gly Pro Ala Ser Phe Leu Asp Asp Ala
                    325                 330                 335

Gly Ile Pro Val Thr Leu Asp Leu Pro Gly Val Gly Ala Asn Leu Gln
                340                 345                 350

Asp His Cys Gly Pro Pro Val Thr Trp Asn Tyr Thr Glu Pro Tyr Thr
            355                 360                 365

Gly Phe Phe Pro Leu Pro Ser Glu Met Val Asn Asn Ala Thr Phe Lys
        370                 375                 380

Ala Glu Ala Ile Thr Gly Phe Asp Glu Val Pro Ala Arg Gly Pro Tyr
385                 390                 395                 400

Thr Leu Ala Gly Gly Asn Asn Ala Ile Phe Val Ser Leu Pro His Leu
                    405                 410                 415

Thr Ala Asp Tyr Gly Ala Ile Thr Ala Asn Ile Arg Ala Met Val Ala
                420                 425                 430

Asp Gly Thr Ala Ala Ser Tyr Leu Ala Ala Asp Val Arg Thr Ile Pro
            435                 440                 445

Gly Met Val Ala Gly Tyr Glu Ala Gln Leu Leu Val Leu Ala Asp Leu
        450                 455                 460

Leu Asp Asn Pro Glu Ala Pro Ser Leu Glu Thr Pro Trp Ala Thr Ser
465                 470                 475                 480

Glu Ala Pro Gln Thr Ser Ser Val Leu Ala Phe Leu Leu His Pro Leu
                    485                 490                 495

Ser Arg Gly Ser Val Arg Leu Asn Leu Ser Asp Pro Leu Ala Gln Pro
                500                 505                 510

Val Leu Asp Tyr Arg Ser Gly Ser Asn Pro Val Asp Ile Asp Leu His
            515                 520                 525

Leu Ala His Val Arg Phe Leu Arg Gly Leu Leu Asp Thr Pro Thr Met
        530                 535                 540

Gln Ala Arg Gly Ala Leu Glu Thr Ala Pro Gly Ser Ala Val Ala Asp
545                 550                 555                 560

Ser Asp Glu Ala Leu Gly Glu Tyr Val Arg Ser His Ser Thr Leu Ser
                    565                 570                 575

Phe Met His Pro Cys Cys Thr Ala Ala Met Leu Pro Glu Asp Arg Gly
                580                 585                 590

Gly Val Val Gly Pro Asp Leu Lys Val His Gly Ala Glu Gly Leu Arg
            595                 600                 605

Val Val Asp Met Ser Val Met Pro Leu Leu Pro Gly Ala His Leu Ser
        610                 615                 620

Ala Thr Ala Tyr Ala Val Gly Glu Lys Ala Ala Asp Ile Ile Ile Gln
625                 630                 635                 640
```

```
Glu Trp Met Asp Lys Glu Gln
                645

<210> SEQ ID NO 6
<211> LENGTH: 655
<212> TYPE: PRT
<213> ORGANISM: Myceliophthora thermophila

<400> SEQUENCE: 6

Met Glu Leu Leu Arg Val Ser Leu Ala Ala Val Ala Leu Ser Pro Leu
1               5                   10                  15

Ile Leu Phe Gly Val Ala Ala His Pro Thr Ala Arg Ser Ile Ala
            20                  25                  30

Arg Ser Thr Ile Leu Asp Gly Ala Asp Gly Leu Leu Pro Glu Tyr Asp
        35                  40                  45

Tyr Ile Ile Gly Gly Thr Ser Gly Leu Thr Val Ala Asp Arg
    50                  55                  60

Leu Thr Glu Asn Arg Lys Arg Lys Phe Ser Arg Ser Pro Leu Pro Thr
65                  70                  75                  80

Ser Pro Ala Arg Ser Ser Pro Ala Trp Cys Tyr Ser Val Leu Val Leu
                85                  90                  95

Glu Arg Gly Ile Phe Gln Asn Ser Ser Ser Val Thr Thr Ile Ser Gly
            100                 105                 110

Gly Ser Arg Gly Leu Phe Asp Pro Ser Leu Thr Phe Asn Ile Asn Ser
        115                 120                 125

Val Pro Gln Ala Gly Leu Asp Asn Arg Ser Ile Ala Val Ile Gly Gly
130                 135                 140

Leu Ile Leu Gly Gly Ser Ser Gly Val Asn Gly Leu Gln Val Leu Arg
145                 150                 155                 160

Gly Gln Arg Glu Asp Tyr Asp Arg Trp Gly Ser Tyr Phe Gly Pro Asn
                165                 170                 175

Ser Asp Trp Ser Trp Lys Gly Leu Leu Pro Tyr Phe Lys Lys Ala Trp
            180                 185                 190

Asn Phe His Pro Pro Arg Pro Glu Leu Val Ser Gln Phe Asp Ile Lys
        195                 200                 205

Tyr Asp Pro Ser Tyr Trp Gly Asn Thr Ser Asp Val His Ala Ser Phe
210                 215                 220

Pro Thr Thr Phe Trp Pro Val Leu Lys Leu Glu Met Ala Ala Phe Gly
225                 230                 235                 240

Asp Ile Pro Gly Val Glu Tyr Pro Pro Asp Ser Ala Ser Gly Glu Thr
                245                 250                 255

Gly Ala Tyr Trp His Pro Ala Ser Val Asp Pro Ala Thr Val Leu Arg
            260                 265                 270

Ser Phe Ala Arg Pro Ala His Trp Asp Asn Ile Glu Ala Ala Arg Pro
        275                 280                 285

Asn Tyr His Thr Leu Thr Gly Gln Arg Val Leu Lys Val Ala Phe Asp
290                 295                 300

Gly Asn Arg Ala Thr Ser Val Val Phe Val Pro Ala Asn Ala Thr Asp
305                 310                 315                 320

His Ser Thr Ala Arg Ser Val Lys Ala Lys Lys Glu Ile Val Leu Ala
                325                 330                 335

Ala Gly Ala Ile His Thr Pro Gln Ile Leu Gln Ala Ser Gly Val Gly
            340                 345                 350

Pro Lys Gln Val Leu Lys Glu Ala Gly Val Pro Leu Val Val Asp Ala
```

```
                355                 360                 365
Pro Gly Val Gly Ser Asn Phe Gln Asp Gln Pro Tyr Val Val Ala Pro
370                 375                 380

Thr Phe Asn Phe Thr Lys Phe Pro Phe His Pro Asp Phe Tyr Asp Met
385                 390                 395                 400

Ile Leu Asn Gln Thr Phe Ile Ala Glu Ala Gln Ala Gln Phe Glu Lys
                405                 410                 415

Asp Arg Thr Gly Pro His Thr Ile Ala Ser Gly Tyr Cys Gly Ser Trp
            420                 425                 430

Leu Pro Leu Gln Ile Ile Ala Pro Asn Ser Trp Lys Asp Ile Ala Arg
        435                 440                 445

Arg Tyr Glu Ser Gln Asp Pro Ala Ala Tyr Leu Pro Ala Gly Thr Asp
    450                 455                 460

Glu Thr Val Ile Glu Gly Tyr Arg Ala Gln Gln Lys Ala Leu Ala Arg
465                 470                 475                 480

Ser Met Arg Ser Lys Gln Ser Ala Met Tyr Asn Phe Phe Leu Arg Gly
                485                 490                 495

Gly Tyr Glu Glu Gly Ser Val Val Tyr Leu His Pro Thr Ser Arg Gly
            500                 505                 510

Thr Val Arg Ile Asn Arg Ser Asp Pro Phe Phe Ser Pro Pro Glu Val
        515                 520                 525

Asp Tyr Arg Ala Leu Ser Asn Pro Thr Asp Leu Glu Val Leu Leu Glu
    530                 535                 540

Phe Thr Pro Phe Thr Arg Arg Tyr Phe Leu Glu Thr Arg Leu Lys Ser
545                 550                 555                 560

Leu Asp Pro Val Glu Leu Ser Pro Gly Ala Asn Val Thr Ala Pro Ala
                565                 570                 575

Asp Ile Glu Ala Trp Leu Arg Ser Val Met Ile Pro Ser Ser Phe His
            580                 585                 590

Pro Ile Gly Thr Ala Ala Met Leu Pro Arg His Leu Gly Gly Val Val
        595                 600                 605

Asp Glu Asn Leu Leu Val Tyr Gly Val Glu Gly Leu Ser Val Val Asp
    610                 615                 620

Ala Ser Val Met Pro Asp Leu Pro Gly Ser Tyr Thr Gln Gln Thr Val
625                 630                 635                 640

Tyr Ala Ile Ala Glu Lys Ala Ala Asp Leu Ile Lys Ser Arg Ala
                645                 650                 655

<210> SEQ ID NO 7
<211> LENGTH: 578
<212> TYPE: PRT
<213> ORGANISM: Myceliophthora thermophila

<400> SEQUENCE: 7

Met Gln Val Ala Ser Lys Leu Val Ala Val Thr Gly Gly Ala Leu Ala
1               5                   10                  15

Leu Trp Leu His Pro Val Ala Ala Gln Glu Gly Cys Thr Asn Ile Ser
                20                  25                  30

Ser Thr Glu Thr Tyr Asp Tyr Ile Val Val Gly Ser Gly Ala Gly Gly
            35                  40                  45

Ile Pro Val Ala Asp Arg Leu Ser Glu Ala Gly His Lys Val Leu Leu
        50                  55                  60

Ile Glu Lys Gly Pro Pro Ser Thr Gly Arg Trp Gly Gly Ile Met Lys
65                  70                  75                  80
```

```
Pro Glu Trp Leu Ile Gly Thr Asn Leu Thr Arg Phe Asp Val Pro Gly
                85                  90                  95

Leu Cys Asn Gln Ile Trp Ala Asp Pro Thr Gly Ala Ile Cys Thr Asp
            100                 105                 110

Val Asp Gln Met Ala Gly Cys Met Leu Gly Gly Thr Ala Val Asn
        115                 120                 125

Ala Gly Leu Trp Trp Lys Pro His Pro Ala Asp Trp Asp Val Asn Phe
    130                 135                 140

Pro Glu Gly Trp His Ser Glu Asp Met Ala Glu Ala Thr Glu Arg Val
145                 150                 155                 160

Phe Glu Arg Ile Pro Gly Thr Ile Thr Pro Ser Met Asp Gly Lys Arg
                165                 170                 175

Tyr Leu Ser Gln Gly Phe Asp Met Leu Gly Gly Ser Leu Glu Ala Ala
            180                 185                 190

Gly Trp Glu Tyr Leu Val Pro Asn Glu His Pro Asp Arg Lys Asn Arg
        195                 200                 205

Thr Tyr Gly His Ser Thr Phe Met Tyr Ser Gly Gly Glu Arg Gly Gly
    210                 215                 220

Pro Leu Ala Thr Tyr Leu Val Ser Ala Val Gln Arg Glu Gly Phe Thr
225                 230                 235                 240

Leu Trp Met Asn Thr Thr Val Thr Arg Ile Ile Arg Glu Gly Gly His
                245                 250                 255

Ala Thr Gly Val Glu Val Gln Cys Ser Asn Ser Glu Ala Gly Gln Ala
            260                 265                 270

Gly Ile Val Pro Leu Thr Pro Lys Thr Gly Arg Val Ile Val Ser Ala
        275                 280                 285

Gly Ala Phe Gly Ser Ala Lys Leu Leu Phe Arg Ser Gly Ile Gly Pro
    290                 295                 300

Lys Asp Gln Leu Asn Ile Val Lys Asn Ser Thr Asp Gly Pro Ser Met
305                 310                 315                 320

Ile Ser Glu Asp Gln Trp Ile Glu Leu Pro Val Gly Tyr Asn Leu Asn
                325                 330                 335

Asp His Val Gly Thr Asp Ile Glu Ile Ala His Pro Asp Val Val Phe
            340                 345                 350

Tyr Asp Tyr Tyr Gly Ala Trp Asp Glu Pro Ile Val Glu Asp Thr Glu
        355                 360                 365

Arg Tyr Val Ala Asn Arg Thr Gly Pro Leu Ala Gln Ala Ala Pro Asn
    370                 375                 380

Ile Gly Pro Ile Phe Trp Glu Thr Ile Lys Gly Ser Asp Gly Val Ser
385                 390                 395                 400

Arg His Leu Gln Trp Gln Ala Arg Val Glu Gly Lys Leu Asn Thr Ser
                405                 410                 415

Met Thr Ile Thr Gln Tyr Leu Gly Thr Gly Ser Arg Ser Arg Gly Arg
            420                 425                 430

Met Thr Ile Thr Arg Arg Leu Asn Thr Val Ser Thr Pro Pro Tyr
        435                 440                 445

Leu Arg Asp Glu Tyr Asp Arg Glu Ala Val Ile Gln Gly Ile Ala Asn
    450                 455                 460

Leu Arg Glu Ser Leu Lys Gly Val Ala Asn Leu Thr Trp Ile Thr Pro
465                 470                 475                 480

Pro Ser Asn Val Thr Val Glu Asp Phe Val Asp Ser Ile Pro Ala Thr
                485                 490                 495

Pro Ala Arg Arg Cys Ser Asn His Trp Ile Gly Thr Ala Lys Ile Gly
```

```
                500             505             510
Leu Asp Asp Gly Arg Glu Gly Thr Ser Val Val Asp Leu Asn Thr
            515             520             525

Lys Val Tyr Gly Thr Asp Asn Ile Phe Val Val Asp Ala Ser Ile Phe
            530             535             540

Pro Gly His Ile Thr Gly Asn Pro Ser Ala Ala Ile Val Ile Ala Ala
545             550             555             560

Glu Tyr Ala Ala Ala Lys Ile Leu Ala Leu Pro Ala Pro Glu Asp Ala
            565             570             575

Ala Ser

<210> SEQ ID NO 8
<211> LENGTH: 610
<212> TYPE: PRT
<213> ORGANISM: Myceliophthora thermophila

<400> SEQUENCE: 8

Met Ala Ser Val Asp Leu Asp Gln Pro Phe Asp Tyr Ile Val Val Gly
1               5                   10                  15

Gly Gly Thr Ala Gly Leu Val Val Ala Asn Arg Leu Ser Glu Asp Ser
            20                  25                  30

Asn Val Arg Val Leu Val Val Glu Ala Gly Ala Asp Arg Asn Ala Asp
        35                  40                  45

Pro Leu Val Leu Thr Pro Gly Leu Val Ala Gly Leu Tyr Gly Lys Asp
    50                  55                  60

Glu Tyr Asp Trp Asn Phe Ser Ser Pro Gln Pro Thr Leu Asn Asn
65                  70                  75                  80

Arg Arg Ile Asn Gln Ala Arg Gly Lys Met Leu Gly Gly Thr Ser Gly
                85                  90                  95

Leu Asn Phe Met Met Leu Leu Tyr Pro Ser Lys Gly Asn Ile Asp Ser
            100                 105                 110

Trp Ala Ala Leu Gly Asn Pro Ser Trp Asn Tyr Asp Ala Leu Ala Pro
        115                 120                 125

Tyr Leu Arg Lys Phe Ala Thr Val His Pro Ser Pro Gln Ser Ala Arg
    130                 135                 140

Asp Leu Leu Gly Leu Thr Tyr Ile Asp Glu Ser Leu Ala Ala Gly Asp
145                 150                 155                 160

Gly Pro Ile Gln Val Ser His Thr Asp Gly His Asn Val Thr Asn Lys
                165                 170                 175

Ala Trp Leu Glu Thr Phe Ala Ser Leu Gly Leu Glu Val Ser Thr Asp
            180                 185                 190

Pro Arg Asp Gly Lys Ala Leu Gly Ala Phe Gln Asn His Ala Ser Ile
        195                 200                 205

Asp Pro Ala Thr His Thr Arg Ser Phe Ala Gly Pro Ala Tyr Tyr Thr
    210                 215                 220

Pro Asp Val Ala Lys Arg Pro Asn Leu Val Val Leu Thr Glu Thr Leu
225                 230                 235                 240

Val Ala Arg Val Leu Phe Asp Thr Ala Gly Gly Glu Gly Asp Ala Val
                245                 250                 255

Ala Thr Gly Val Glu Ile Ile Thr Lys Asp Gly Gln Lys Lys Gln Val
            260                 265                 270

Ser Ala Cys Gly Glu Val Ile Leu Ala Ala Gly Ala Leu Gln Ser Pro
        275                 280                 285

Gln Ile Leu Glu Leu Ser Gly Val Gly Gly Arg Glu Leu Leu Glu Lys
```

```
                290                 295                 300
His Asn Ile Pro Val Val Asp Asn Pro Asn Val Gly Glu His Val
305                 310                 315                 320

Gln Asp His Pro Ile Val Cys Gln Ser Phe Glu Val Ala Asp Gly Val
                325                 330                 335

Pro Ser Gly Asp Val Leu Arg Asp Pro Asn Val Leu Gln Ala Val Val
                340                 345                 350

Gly Met Tyr Gln Ser Gly Gly Gly Ala Gly Pro Leu Gly Gln Ser Val
                355                 360                 365

Ile Ser Val Ala Tyr Thr Pro Leu Val Asp Gly Ser Gly Val Val Ser
                370                 375                 380

Ala Glu Ala Lys Ala Glu Leu Leu Ala Arg His Glu Ser Ser Phe Ser
385                 390                 395                 400

Thr Ala Glu Gly Lys Val Leu Arg Asp Leu Val Glu Ser Pro Ser Glu
                405                 410                 415

Ala Thr Phe Glu Phe Leu Leu Phe Pro Ser Gln Val Asp Ile Pro Glu
                420                 425                 430

Asn Pro Thr Ser Met Ala Gln Tyr Ile Thr Pro Val Leu Pro Glu Asn
                435                 440                 445

Tyr Ile Ser Val Met Thr Phe Ile His Gln Pro Phe Ser Arg Gly Lys
                450                 455                 460

Val His Ile Thr Ser Pro Asp Ile Arg Ala Ala Pro Leu Trp Asp Pro
465                 470                 475                 480

Arg Tyr Asn Ser Asp Pro Leu Asp Leu Glu Leu Leu Ala Arg Gly Val
                485                 490                 495

Gln Phe Val Glu Arg Ile Val Asp Ser Ala Thr Pro Phe Gly Arg Val
                500                 505                 510

Leu Lys Gln Gly Gly Lys Arg Gln Pro Pro Leu Arg Ala Asp Asp Leu
                515                 520                 525

Glu Thr Ala Arg Glu Ile Val Arg Gln Arg Gln Ile Ser Val Phe His
                530                 535                 540

Val Ser Gly Ser Cys Thr Met Arg Pro Arg Asp Gln Gly Gly Val Val
545                 550                 555                 560

Asp Glu Arg Leu Arg Val Tyr Gly Thr Arg Gly Leu Arg Val Val Asp
                565                 570                 575

Ala Ser Val Phe Pro Ile Glu Pro Val Gly Asn Ile Gln Ser Val Val
                580                 585                 590

Tyr Ala Val Ala Glu Arg Ala Ala Asp Leu Ile Lys Glu Asp Arg Ala
                595                 600                 605

Lys Ala
    610

<210> SEQ ID NO 9
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 9
cacgcggggt tctttctcca tctc                                            24

<210> SEQ ID NO 10
<211> LENGTH: 47
<212> TYPE: DNA
<213> ORGANISM: Artificial Sequence
```

```
<220> FEATURE:
<223> OTHER INFORMATION: Synthetic DNA primer

<400> SEQUENCE: 10
tgaggaaaac gccgagactg agctcgactc tgccggccta cctacga          47

<210> SEQ ID NO 11
<211> LENGTH: 48
<212> TYPE: DNA
<213> ORGANISM: Artificial Sequence
<220> FEATURE:
<223> OTHER INFORMATION: Synthetic DNA primer

<400> SEQUENCE: 11
atcagttggg tgcacgagtg ggttttgatg gggagttgag tttgtgaa          48

<210> SEQ ID NO 12
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 12
ggatggatga ggttgttttt gagc          24

<210> SEQ ID NO 13
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 13
aacccactcg tgcacccaac tgat          24

<210> SEQ ID NO 14
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 14
gaccacgatg ccggctacga tacc          24

<210> SEQ ID NO 15
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 15
acatggcccc actcgcttct taca          24

<210> SEQ ID NO 16
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 16
aagcgtgccg attttcctga tttc          24
```

```
<210> SEQ ID NO 17
<211> LENGTH: 21
<212> TYPE: DNA
<213> ORGANISM: Artificial Sequence
<220> FEATURE:
<223> OTHER INFORMATION: Synthetic DNA primer

<400> SEQUENCE: 17
gcatttctgg ggcggttagc a                                        21

<210> SEQ ID NO 18
<211> LENGTH: 21
<212> TYPE: DNA
<213> ORGANISM: Artificial Sequence
<220> FEATURE:
<223> OTHER INFORMATION: Synthetic DNA primer

<400> SEQUENCE: 18
tcatcgacgc ctccatcttc c                                        21

<210> SEQ ID NO 19
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 19
tttcggttgt cgtgtttcca ttat                                     24

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 20
ggagatcctg gaggatttcc                                          20

<210> SEQ ID NO 21
<211> LENGTH: 22
<212> TYPE: DNA
<213> ORGANISM: Artificial Sequence
<220> FEATURE:
<223> OTHER INFORMATION: Synthetic DNA primer

<400> SEQUENCE: 21
caggcggtgt gcgttatcaa aa                                       22
```

FUNGAL STRAINS

The present application claims priority to U.S. Prov. Patent Appln. Ser. Nos. 61/409,186, 61/409,217, 61/409,472, and 61/409,480, all of which were filed on Nov. 2, 2010, and U.S. Prov. Patent Appln. Ser. No. 61/497,661, filed on Jun. 16, 2011, all of which are hereby incorporated by reference herein.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX3-082US1_ST25.TXT, created on Dec. 7, 2011, 47,145 bytes, machine format IBM-PC, MS-Windows operating system, is hereby incorporated by reference.

FIELD OF THE INVENTION

The present invention provides improved fungal strains. In some embodiments, the improved fungal strains find use in hydrolyzing cellulosic material to glucose.

BACKGROUND OF THE INVENTION

Cellulose is a polymer of the simple sugar glucose linked by beta-1,4 glycosidic bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or landfilling the materials, and lower overall greenhouse gas production. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

SUMMARY OF THE INVENTION

The present invention provides improved fungal strains. In some embodiments, the improved fungal strains find use in hydrolyzing cellulosic material to glucose.

The present invention provides a fungal cell that has been genetically modified to reduce the amount of endogenous cellobiose dehydrogenase activity that is secreted by the cell, wherein the fungal cell is from the family Chaetomiaceae, wherein said cell comprises a deletion in the cellobiose dehydrogenase 1 (cdh1) gene. In some embodiments, the fungal cell is a species of *Myceliophthora*. In some further embodiments, the fungal cell is *Myceliophthora thermophila*. In some embodiments, the fungal cell has been genetically modified to disrupt the secretion signal peptide of the cellobiose dehydrogenase. In some additional embodiments, the fungal cell has been genetically modified to reduce the amount of the endogenous cellobiose dehydrogenase expressed by the cell. In some further embodiments, the fungal cell has been genetically modified to disrupt a translation initiation sequence in the transcript encoding the endogenous cellobiose dehydrogenase. In some still additional embodiments, the fungal cell has been genetically modified to introduce a frameshift mutation in the transcript encoding the endogenous cellobiose dehydrogenase. In some further embodiments, the fungal cell has been genetically modified to reduce the transcription level of a gene encoding the endogenous cellobiose dehydrogenase. In some additional embodiments, the fungal cell has been genetically modified to disrupt the promoter of a gene encoding the endogenous cellobiose dehydrogenase. In some embodiments, the fungal cell has been genetically modified to at least partially delete a gene encoding the endogenous cellobiose dehydrogenase. In some further embodiments, the fungal cell has been genetically modified to reduce the catalytic efficiency of the endogenous cellobiose dehydrogenase. In some additional embodiments, one or more residues in an active site of the cellobiose dehydrogenase in the fungal cell have been genetically modified. In some still further embodiments, one or more residues in a heme binding domain of the cellobiose dehydrogenase in the fungal cell have been genetically modified.

In some embodiments, the present invention provides fungal cells comprising cellobiose dehydrogenase. In some embodiments, the cellobiose dehydrogenase comprises an amino acid sequence that is at least about 85%, about 88%, about 90%, about 93%, about 95%, about 97%, about 98%, or about 99% identical to SEQ ID NO:2. In some additional embodiments, the fungal cell has been modified such that the cell secretes a reduced amount of endogenous cellobiose dehydrogenase 1 (cdh1), as compared to a fungal cell prior to or without such modification.

The present invention also provides an enzyme mixture comprising two or more cellulose hydrolyzing enzymes, wherein at least one of the two or more cellulose hydrolyzing enzymes is expressed by the fungal cell. In some embodiments, the enzyme mixture is a cell-free mixture. In some additional embodiments, pretreated lignocellulose comprises at least one substrate of the enzyme mixture. In some further embodiments, the pretreated lignocellulose comprises lignocellulose treated by at least one treatment method selected from acid pretreatment, ammonia pretreatment, steam explosion, and/or organic solvent extraction.

The present invention also provides methods for generating glucose comprising contacting at least one cellulose substrate with an enzyme mixture comprising two or more cellulose hydrolyzing enzymes, wherein at least one of the two or more cellulose hydrolyzing enzymes is expressed by a fungal cell provided herein. The present invention also provides methods for generating glucose, comprising contacting at least one cellulose substrate with at least one enzyme mixture provided herein. In some further embodiments, the enzyme mixture is a cell-free mixture. In some additional embodiments, the cellulose substrate is pretreated lignocellulose. In still some further embodiments, the pretreated lignocellulose comprises lignocellulose treated by at least one treatment method selected from acid pretreatment, ammonia pretreatment, steam explosion, and/or organic solvent extraction In some additional embodiments, the methods of the present invention further comprise fermenting the glucose to an end product. In some further embodiments, the end product is a fuel alcohol or a precursor industrial chemical. In some additional embodiments, the fuel alcohol is ethanol or butanol. In still some additional embodiments, the methods, enzyme mixtures, and/or fungal cells of the present invention provide at least one cellulose degrading enzyme that is homologous or heterologous to the fungal cell.

The present invention also provides fermentation media comprising at least one fungal cell and/or at least one enzyme mixture as provided herein.

BRIEF DESCRIPTION OF THE DRAWINGS

FIG. 1 provides the nucleotide and amino acid sequences of *M. thermophila* CDH1 (SEQ ID NOS:1 and 2, respectively).

DESCRIPTION OF THE INVENTION

Figure 2:
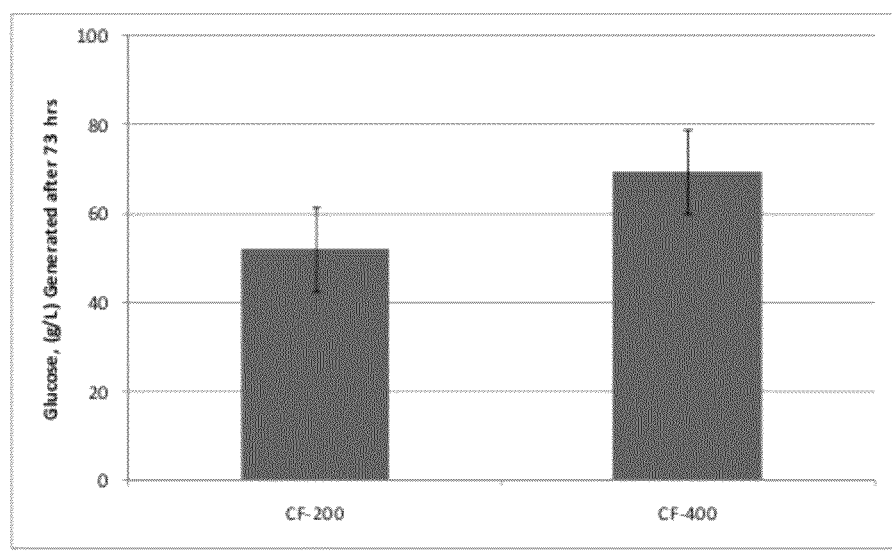
FIG. 2 provides a graph showing the relative saccharification efficiency of CF-200 and CF-400, as measured in glucose produced from 100 g/kg glucan (pre-treated corn stover). Reactions were run at 24.6% solids, with 128 mM NaOAc, at pH 5, 55° C., 3% enzyme, in 110 µL volumes. Glucose was measured using the GOPOD assay. Error bars represent ±1 SD, n=4.

The present invention provides improved fungal strains. In some embodiments, the improved fungal strains find use in hydrolyzing cellulosic material to glucose. As indicated herein, the present invention provides improved fungal strains for the conversion of cellulose to glucose. In particular, the improved fungal strains provided herein are genetically modified to reduce the amount of endogenous cellobiose dehydrogenase activity secreted by the cells. Prior to the present invention, it was generally believed that cellobiose dehydrogenase enhances the rate of cellulose hydrolysis by reducing the concentration of cellobiose, which is a potent inhibitor of some cellulase components (See e.g., Mansfield et al., Appl. Environ. Microbiol., 63:3804-3809 [1997]; and Igarishi et al., Eur. J. Biochem., 253:101-106 [1998]). Furthermore, cellobiose dehydrogenase has been reported as playing a critical role in contributing to synergistic enhancement during cellulose degradation by preventing hydrolysis product inhibition (See e.g., Hai et al., J. Appl. Glycosci., 49:9-17 [2002]). It was also generally believed that cellobiose dehydrogenase was useful in delignifying lignocellulose, thereby enhancing cellulose degradation. Recently, it has been reported that cellobiose dehydrogenases can enhance the activity of cellulolytic enhancing proteins from Glycosyl Hydrolase Family 61 (See e.g., WO2010/080532A1), and may find use in reactions for redox balance purposes.

Contrary to general understanding in the art, the present invention provides genetic modifications (e.g., deletion) of a cellobiose dehydrogenase-encoding gene in cellulase-producing fungal cells. This modification results in an improvement in the yield of fermentable sugars from enzyme mixtures secreted by the genetically modified cells. Thus, reduction of cellobiose dehydrogenase secreted by a cellulase-producing organism provides a mixture of cellulase enzymes that can improve yield of fermentable sugars during enzymatic hydrolysis of cellulose-containing substrates. In addition, deletion of the cdh gene provides additional room in the fungal cell genome for introduction of other sequences (e.g., heterologous sequences encoding proteins of interest).

Accordingly, provided herein is a fungal cell that has been genetically modified to reduce the amount of endogenous cellobiose dehydrogenase activity that is secreted by the cell, wherein the fungal cell is from the family Chaetomiaceae, and wherein the fungal cell is capable of secreting a cellulose-containing enzyme mixture. In some embodiments, the fungal cell is capable of secreting an enzyme mixture comprising two or more cellulase enzymes. In some embodiments, the fungal cell is a Chaetomiaceae family member of the genus *Achaetomium, Aporothielavia, Chaetomidium, Chaetomium, Corylomyces, Corynascus, Farrowia, Thielavia, Zopfiella,* or *Myceliophthora*. In some embodiments, the genetically modified fungal cell provided herein is a Chaetomiaceae family member selected from the genera *Myceliophthora, Thielavia, Corynascus,* or *Chaetomium*.

It is recognized that fungal taxonomy continues to undergo reorganization. Thus, it is intended that all aspects of the present invention encompass genera and species that have been reclassified, including but not limited to such organisms as *Myceliophthora thermophila*, which has also been given various other names (e.g., *Sporotrichum thermophile, Sporotrichum thermophilum, Thelavia heterothallica, Corynascus heterothallica, Chrysoporium thermophilum,* and *Myceliophthora indica*). Indeed, it is intended that the present invention encompass all teleomorphs, anamorphs, and synonyms, basionyms, or taxonomic equivalents thereof.

In some embodiments, the fungal cell has been genetically modified to reduce the amount of endogenous cellobiose dehydrogenase activity that is secreted by the cell. In some embodiments, the fungal cell is a species of *Myceliophthora, Thielavia, Sporotrichum, Corynascus, Acremonium, Chaetomium, Ctenomyces, Scytalidium, Talaromyces,* or *Thermoascus*. In some embodiments, the fungal cell is *Sporotrichum cellulophilum, Thielavia terrestris, Corynascus heterothallicus, Thielavia heterothallica, Chaetomium globosum, Talaromyces stipitatus,* or *Myceliophthora thermophila*. In some embodiments, the fungal cell is an isolated fungal cell.

In some embodiments, the fungal cell has been genetically modified to reduce the amount of endogenous cellobiose dehydrogenase secreted by the cell. In some embodiments, the fungal cell has been genetically modified to disrupt the secretion signal peptide of cellobiose dehydrogenase. In some embodiments, the fungal cell has been genetically modified to reduce the amount of the endogenous cellobiose dehydrogenase expressed by the cell. For example, in some embodiments, the fungal cell is genetically modified to disrupt a translation initiation sequence, while in some other embodiments, the fungal cell is genetically modified to introduce a frameshift mutation in the transcript encoding the endogenous cellobiose dehydrogenase. In some other embodiments, the fungal cell has been genetically modified to reduce the transcription level of a gene encoding the endogenous cellobiose dehydrogenase. For example, in some embodiments, the fungal cell is genetically modified to disrupt the promoter of a gene encoding the endogenous cellobiose dehydrogenase. For example, in some embodiments, the fungal cell is genetically modified to disrupt the gene encoding the endogenous cellobiose dehydrogenase through use of stop codons, terminator elimination, transposons, etc. In some additional embodiments, the fungal cell has been genetically modified to at least partially delete a gene encoding the endogenous cellobiose dehydrogenase. In some other embodiments, the fungal cell has been genetically modified to reduce the catalytic efficiency of the endogenous cellobiose dehydrogenase. In some embodiments, the fungal cell has been genetically modified, such that one or more residues in an active site of the cellobiose dehydrogenase have been mutated. In some embodiments, one or more residues in a heme binding domain of the cellobiose dehydrogenase of the fungal cell have been genetically modified. Indeed, it is intended that any suitable means for modifying the fungal cell to reduce the amount of cellobiose dehydrogenase expressed and/or secreted by the cell will find use in the present invention.

In some embodiments, the cellobiose dehydrogenase is encompassed within EC 1.1.99.18. In some embodiments, the cellobiose dehydrogenase comprises an amino acid sequence that is at least about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:2.

In some embodiments, the fungal cell further comprises at least one gene encoding at least one cellulose degrading enzyme that is heterologous to the fungal cell. For example, in some embodiments, the fungal cell overexpresses a homologous or heterologous gene encoding a cellulose degrading enzyme such as beta-glucosidase. In some embodiments, the fungal cell overexpresses beta-glucosidase and has been genetically modified to reduce the amount of endogenous cellobiose dehydrogenase activity secreted by the cell.

The present invention also provides enzyme mixtures comprising two or more cellulose hydrolyzing enzymes, wherein at least one of the two or more cellulose hydrolyzing enzymes is expressed by a fungal cell as provided herein. For example, in some embodiments, the fungal cell is a cell that has been genetically modified to reduce the amount of endogenous cellobiose dehydrogenase activity secreted by the cell, wherein the fungal cell is a member of the genus *Myceliophthora, Thielavia, Sporotrichum, Corynascus, Acremonium, Chaetomium, Ctenomyces, Scytalidium, Talaromyces,* or *Thermoascus*. In some embodiments, the enzyme mixture is a cell-free mixture. In some additional embodiments, a substrate of the enzyme mixture comprises pretreated lignocellulose. In some embodiments, the pretreated lignocellulose comprises lignocellulose treated by acid pretreatment, ammonia pretreatment, steam explosion, and/or organic solvent extraction. In some embodiments, the enzyme mixture further comprises at least one cellulose degrading enzyme that is heterologous to the fungal cell. In some embodiments, at least one of the two or more cellulose hydrolyzing enzymes is expressed by an isolated fungal cell.

The present invention also provides methods for generating glucose that comprise contacting cellulose with a mixture of at least two enzymes. For example, in some embodiments, the methods comprise contacting cellulose with an enzyme mixture comprising two or more cellulose hydrolyzing enzymes, wherein at least one of the two or more cellulose hydrolyzing enzymes is expressed by a fungal cell as described herein. In some embodiments, the methods comprise contacting cellulose with an enzyme mixture comprising two or more cellulose hydrolyzing enzymes, wherein at least one of the two or more cellulose hydrolyzing enzymes is expressed by a cell that has been genetically modified to reduce the amount of endogenous cellobiose dehydrogenase activity secreted by the cell, wherein the fungal cell is *Myceliophthora, Thielavia, Sporotrichum, Corynascus, Acremonium, Chaetomium, Ctenomyces, Scytalidium, Talaromyces,* or *Thermoascus*. In some embodiments, the methods result in an increased yield of glucose and/or cellobiose from the hydrolyzed cellulose and decreased oxidation of the cellobiose to oxidized sugar products, such as gluconolactone, gluconate, gluconic acid, cellobionolactone, and/or cellobionic acid from the hydrolyzed cellulose.

In some embodiments, the enzyme mixture is a cell-free mixture. In some further embodiments, the cellulose substrate comprises pretreated lignocellulose. In some additional embodiments, the pretreated lignocellulose comprises lignocellulose treated by at least one treatment method such as acid pretreatment, ammonia pretreatment, steam explosion and/or organic solvent extraction.

In some embodiments, the methods further comprise fermentation of the glucose to an end product such as a fuel alcohol or a precursor industrial chemical. In some embodiments, the fuel alcohol is ethanol or butanol. In some embodiments, the methods comprise contacting cellulose with an enzyme mixture that further comprises a cellulose degrading enzyme that is heterologous to the fungal cell.

Also provided herein are fermentation media comprising the fungal cell of any of the above embodiments, and/or comprising the enzyme mixture derived from the fungal cell of any of the above embodiments.

DEFINITIONS

Unless otherwise indicated, the practice of the present invention involves conventional techniques commonly used in molecular biology, protein engineering, and microbiology, which are within the skill of the art. Such techniques are well-known and described in numerous texts and reference works well known to those of skill in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Many technical dictionaries are known to those of skill in the art. Although any suitable methods and materials similar or equivalent to those described herein find use in the practice of the present invention, some preferred methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole.

Also, as used herein, the singular "a", "an," and "the" include the plural references, unless the context clearly indicates otherwise. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein. Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below. Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

As used herein, "substrate" refers to a substance or compound that is converted or meant to be converted into another compound by the action of an enzyme. The term includes not only a single compound but also combinations of compounds, such as solutions, mixtures and other materials which contain at least one substrate.

As used herein, "conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a cellobiose dehydrogenase ("CDH" or "cdh") polypeptide can be expressed as "percent conversion" of the substrate to the product.

As used herein, "secreted activity" refers to enzymatic activity of cellobiose oxidizing enzymes produced by a fungal cell that is present in an extracellular environment. An extracellular environment can be, for example, an extracellular milieu such as a culture medium. The secreted activity is influenced by the total amount of cellobiose oxidizing enzyme secreted, and also is influenced by the catalytic efficiency of the secreted cellobiose oxidizing enzyme.

As used herein, a "reduction in catalytic efficiency" refers to a reduction in the activity of the cellobiose oxidizing enzyme, relative to unmodified cellobiose oxidizing enzyme, as measured using standard techniques, as provided herein or otherwise known in the art.

As used herein, the term "enzyme mixture" refers to a combination of at least two enzymes. In some embodiments, at least two enzymes are present in a composition. In some additional embodiments, the enzyme mixtures are present within a cell (e.g., a fungal cell). In some embodiments, each or some of the enzymes present in an enzyme mixture are produced by different fungal cells and/or different fungal cultures. In some further embodiments, all of the enzymes present in an enzyme mixture are produced by the same cell. In some embodiments, the enzyme mixtures comprise cellulase enzymes, while in some additional embodiments, the enzyme mixtures comprise enzymes other than cellulases. In some embodiments, the enzyme mixtures comprise at least one cellulase and at least one enzyme other than a cellulase. In some embodiments, the enzyme mixtures comprise enzymes including, but not limited to endoxylanases (EC 3.2.1.8), beta-xylosidases (EC 3.2.1.37), alpha-L-arabinofuranosidases (EC 3.2.1.55), alpha-glucuronidases (EC 3.2.1.139), acetylxylanesterases (EC 3.1.1.72), feruloyl esterases (EC 3.1.1.73), coumaroyl esterases (EC 3.1.1.73), alpha-galactosidases (EC 3.2.1.22), beta-galactosidases (EC 3.2.1.23), beta-mannanases (EC 3.2.1.78), beta-mannosidases (EC 3.2.1.25), endo-polygalacturonases (EC 3.2.1.15), pectin methyl esterases (EC 3.1.1.11), endo-galactanases (EC 3.2.1.89), pectin acetyl esterases (EC 3.1.1.6), endo-pectin lyases (EC 4.2.2.10), pectate lyases (EC 4.2.2.2), alpha rhamnosidases (EC 3.2.1.40), exo-galacturonases (EC 3.2.1.82), exo-galacturonases (EC 3.2.1.67), exopolygalacturonate lyases (EC 4.2.2.9), rhamnogalacturonan endolyases EC (4.2.2.B3), rhamnogalacturonan acetylesterases (EC 3.2.1.B11), rhamnogalacturonan galacturonohydrolases (EC 3.2.1.B11), endo-arabinanases (EC 3.2.1.99), laccases (EC 1.10.3.2), manganese-dependent peroxidases (EC 1.10.3.2), amylases (EC 3.2.1.1), glucoamylases (EC 3.2.1.3), lipases, lignin peroxidases (EC 1.11.1.14), and/or proteases.

In some additional embodiments, the present invention further provides enzyme mixtures comprising at least one expansin and/or expansin-like protein, such as a swollenin (See e.g., Salheimo et al., Eur. J. Biochem., 269:4202-4211 [2002]) and/or a swollenin-like protein. Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein and/or swollenin-like protein comprises one or both of such domains and/or disrupts the structure of cell walls (e.g., disrupting cellulose structure), optionally without producing detectable amounts of reducing sugars. In some additional embodiments, the enzyme mixtures comprise at least one polypeptide product of a cellulose integrating protein, scaffoldin and/or a scaffoldin-like protein (e.g., CipA or CipC from *Clostridium thermocellum* or *Clostridium cellulolyticum* respectively). In some additional embodiments, the enzyme mixtures comprise at least one cellulose induced protein and/or modulating protein (e.g., as encoded by cip1 or cip2 gene and/or similar genes from *Trichoderma reesei*; See e.g., Foreman et al., J. Biol. Chem., 278:31988-31997 [2003]). In some additional embodiments, the enzyme mixtures comprise at least one member of each of the classes of the polypeptides described above, several members of one polypeptide class, or any combination of these polypeptide classes to provide enzyme mixtures suitable for various uses. Any combination of at least one two, three, four, five, or more than five enzymes and/or polypeptides find use in various enzyme mixtures provided herein. Indeed, it is not intended that the enzyme mixtures of the present invention be limited to any particular enzymes, polypeptides, nor combinations, as any suitable enzyme mixture finds use in the present invention.

As used herein, the term "saccharide" refers to any carbohydrate comprising monosaccharides (e.g., glucose, ribose, fructose, galactose, etc.), disaccharides (e.g., sucrose, lactose, maltose, cellobiose, trehalose, melibiose, etc.), oligosaccharides (e.g., raffinose, stachyose, amylose, etc.), and polysaccharides (e.g., starch, glycogen, cellulose, chitin, xylan, arabinoxylan, mannan, fucoidan, galactomannan, callose, laminarin, chrysolaminarin, amylopectin, dextran, dextrins, maltodextrins, inulin, oligofructose, polydextrose, etc.). The term encompasses simple carbohydrates, as well as complex carbohydrates. Indeed, it is not intended that the present invention be limited to any particular saccharide, as various saccharides and forms of saccharides find use in the present invention.

As used herein, the term "saccharide hydrolyzing enzyme" refers to any enzyme that hydrolyzes at least one saccharide.

As used herein, the terms "cellobiose oxidizing enzyme" refer to enzymes that oxidize cellobiose. In some embodiments, cellobiose oxidizing enzymes include cellobiose dehydrogenase (EC 1.1.99.18).

As used herein, the terms "cellobiose dehydrogenase," "CDH," and "cdh" refer to a cellobiose:acceptor 1-oxidoreductase that catalyzes the conversion of cellobiose in the presence of an acceptor to cellobiono-1,5-lactone and a reduced acceptor. Examples of cellobiose dehydrogenases fall into the enzyme classification (E.C. 1.1.99.18). Typically 2,6-dichloroindophenol can act as acceptor, as can iron, especially $Fe(SCN)_3$, molecular oxygen, ubiquinone, or cytochrome C, and other polyphenolics, such as lignin. Substrates of the enzyme include cellobiose, cello-oligosaccharides, lactose, and D-glucosyl-1,4-β-D-mannose, glucose, maltose, mannobiose, thiocellobiose, galactosyl-mannose, xylobiose, xylose. Electron donors include beta-1-4 dihexoses with glucose or mannose at the reducing end, though alpha-1-4 hexosides, hexoses, pentoses, and beta-1-4 pentomers can act as substrates for at least some of these enzymes (See e.g., Henriksson et al, Biochim. Biophys. Acta—Prot. Struct. Mol. Enzymol., 1383: 48-54 [1998]; and Schou et al., Biochem. J., 330: 565-571 [1998]). In some embodiments, the cellobiose dehydrogenase of interest in the present invention is CDH1, which is encoded by the cdh1 gene.

As used herein, the terms "oxidation", "oxidize(d)" and the like as used herein refer to the enzymatic formation of one or more cellobiose oxidation products. When used in reference to a percentage of oxidized cellobiose, those percentages reflect a weight percent (w/w) relative to the initial amount of substrate. For example, when the enzyme mixture is contacted with cellobiose, the percentage of oxidized cellobiose reflects a weight percent (w/w) relative to the initial amount of cellobiose present in solution. Where the enzyme mixture is contacted with a cellulose substrate, the percentage of oxidized cellobiose reflects a weight percent (w/w) based on the maximum amount (wt %) of glucose that could be produced from the total hydrolyzed cellulose (i.e., Gmax).

As used herein, "cellulose" refers to a polymer of the simple sugar glucose linked by beta-1,4 glycosidic bonds.

As used herein, "cellobiose" refers to a water-soluble beta-1,4-linked dimer of glucose.

As used herein, the term "cellodextrin" refers to a glucose polymer of varying length (i.e., comprising at least two glucose monomers). Each glucose monomer is linked via a beta-1,4 glycosidic bond. A cellodextrin is classified by its degree of polymerization (DP), which indicates the number of glucose monomers the cellodextrin contains. The most common cellodextrins are: cellobiose (DP=2); cellotriose (DP=3); cellotetrose (DP=4); cellopentose (DP=5); and cellohexose (DP=6). In some embodiments, cellodextrins have a DP of 2-6 (i.e., cellobiose, cellotriose, cellotetrose, cellopentose, and/or cellohexose). In some embodiments, cellodextrins have a DP greater than 6. The degree of polymerization of cellodextin molecules can be measured (e.g., by mass spectrometry, including but not limited to matrix-assisted laser desorption/ionization (MALDI) mass spectrometry and electrospray ionization ion trap (ESI-IT) mass spectrometry). Methods of measuring the degree of polymerization of cellodextrin molecules are known in the art (See e.g., Melander et al., Biomacromol., 7:1410-1421 [2006]).

As used herein, the term "cellulase" refers to any enzyme that is capable of degrading cellulose. Thus, the term encompasses enzymes capable of hydrolyzing cellulose (β-1,4-glucan or β-D-glucosidic linkages) to shorter cellulose chains, oligosaccharides, cellobiose and/or glucose. "Cellulases" are divided into three sub-categories of enzymes: 1,4-β-D-glucan glucanohydrolase ("endoglucanase" or "EG"); 1,4-β-D-glucan cellobiohydrolase ("exoglucanase," "cellobiohydrolase," or "CBH"); and β-D-glucoside-glucohydrolase ("β-glucosidase," "cellobiase," "BG," or "BGL"). These enzymes act in concert to catalyze the hydrolysis of cellulose-containing substrates. Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. Beta-glucosidases split the cellobiose into monomers. Cellulases often comprise a mixture of different types of cellulolytic enzymes (endoglucanases and cellobiohydrolases) that act synergistically to break down the cellulose to soluble di- or oligosaccharides such as cellobiose, which are then further hydrolyzed to glucose by beta-glucosidase. Cellulase enzymes are produced by a wide variety of microorganisms. Cellulases (and hemicellulases) from filamentous fungi and some bacteria are widely exploited for many industrial applications that involve processing of natural fibers to sugars.

As used herein, a "cellulase-producing fungal cell" is a fungal cell that produces at least one cellulase enzyme (i.e., "cellulose hydrolyzing enzyme"). In some embodiments, the cellulase-producing fungal cells provided herein express and secrete a mixture of cellulose hydrolyzing enzymes.

As used herein, the terms "cellulose hydrolyzing enzyme," "cellulolytic enzyme," and like terms refer to an enzyme that acts in the process of breaking down cellulose to soluble di- or oligosaccharides such as cellobiose, which are then further hydrolyzed to glucose by beta-glucosidase. A mixture of cellulose hydrolyzing enzymes is also referred to herein as "cellulases," a "cellulase-containing mixture," and/or a "cellulase mixture."

As used herein, the terms "endoglucanase" and "EG" refer to a category of cellulases (EC 3.2.1.4) that catalyze the hydrolysis of internal β-1,4 glucosidic bonds of cellulose. The term "endoglucanase" is further defined herein as an endo-1,4-(1,3; 1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenan, beta-1,4 bonds in mixed beta-1,3 glucans such as cereal beta-D-glucans or xyloglucans, and other plant material containing cellulosic components. Endoglucanase activity can be determined based on a reduction in substrate viscosity or increase in reducing ends determined by a reducing sugar assay (See e.g., Zhang et al., Biotechnol. Adv., 24:452-481 [2006]). For purposes of the present invention, endoglucanase activity is determined using carboxymethyl cellulose (CMC) hydrolysis (See e.g., Ghose, Pur. Appl. Chem., 59:257-268 [1987]).

As used herein, "EG1" refers to a carbohydrate active enzyme expressed from a nucleic acid sequence coding for a glycohydrolase (GH) Family 7 catalytic domain classified under EC 3.2.1.4 or any protein, polypeptide or catalytically active fragment thereof. In some embodiments, the EG1 is functionally linked to a carbohydrate binding module (CBM), such as a Family 1 cellulose binding domain.

As used herein, the term "EG2" refers to a carbohydrate active enzyme expressed from a nucleic acid sequence coding for a glycohydrolase (GH) Family 5 catalytic domain classified under EC 3.2.1.4 or any protein, polypeptide or catalytically active fragment thereof. In some embodiments, the EG2 is functionally linked to a carbohydrate binding module (CBM), such as a Family 1 cellulose binding domain.

As used herein, the term "EG3" refers to a carbohydrate active enzyme expressed from a nucleic acid sequence coding for a glycohydrolase (GH) Family 12 catalytic domain classified under EC 3.2.1.4 or any protein, polypeptide or catalytically active fragment thereof. In some embodiments, the EG3 is functionally linked to a carbohydrate binding module (CBM), such as a Family 1 cellulose binding domain.

As used herein, the term "EG4" refers to a carbohydrate active enzyme expressed from a nucleic acid sequence coding for a glycohydrolase (GH) Family 61 catalytic domain classified under EC 3.2.1.4 or any protein, polypeptide or fragment thereof. In some embodiments, the EG4 is functionally linked to a carbohydrate binding module (CBM), such as a Family 1 cellulose binding domain.

As used herein, the term "EG5" refers to a carbohydrate active enzyme expressed from a nucleic acid sequence coding for a glycohydrolase (GH) Family 45 catalytic domain classified under EC 3.2.1.4 or any protein, polypeptide or fragment thereof. In some embodiments, the EG5 is functionally linked to a carbohydrate binding module (CBM), such as a Family 1 cellulose binding domain.

As used herein, the term "EG6" refers to a carbohydrate active enzyme expressed from a nucleic acid sequence coding for a glycohydrolase (GH) Family 6 catalytic domain classified under EC 3.2.1.4 or any protein, polypeptide or fragment thereof. In some embodiments, the EG6 is functionally linked to a carbohydrate binding module (CBM), such as a Family 1 cellulose binding domain.

As used herein, the terms "cellobiohydrolase" and "CBH" refer to a category of cellulases (EC 3.2.1.91) that hydrolyze glycosidic bonds in cellulose. The term "cellobiohydrolase" is further defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (See e.g., Teeri, Tr. Biotechnol., 15:160-167 [1997]; and Teeri et al., Biochem. Soc. Trans., 26:173-178 [1998]). In some embodiments, cellobiohydrolase activity is determined using a fluorescent disaccharide derivative 4-methylumbelliferyl-.beta.-D-lactoside (See e.g., van Tilbeurgh et al., FEBS Lett., 149:152-156 [1982]; and van Tilbeurgh and Claeyssens, FEBS Lett., 187:283-288 [1985]).

As used herein, the terms "CBH1" and "type 1 cellobiohydrolase" refer to a carbohydrate active enzyme expressed from a nucleic acid sequence coding for a glycohydrolase (GH) Family 7 catalytic domain classified under EC 3.2.1.91 or any protein, polypeptide or catalytically active fragment thereof. In some embodiments, the CBH1 is functionally linked to a carbohydrate binding module (CBM), such as a Family 1 cellulose binding domain.

As used herein, the terms "CBH2" and "type 2 cellobiohydrolase" refer to a carbohydrate active enzyme expressed from a nucleic sequence coding for a glycohydrolase (GH) Family 6 catalytic domain classified under EC 3.2.1.91 or any protein, polypeptide or catalytically active fragment thereof. Type 2 cellobiohydrolases are also commonly referred to as "the Ce16 family." In some embodiments, the CBH2 is functionally linked to a carbohydrate binding module (CBM), such as a Family 1 cellulose binding domain.

As used herein, the terms "beta-glucosidase," "cellobiase," and "BGL" refers to a category of cellulases (EC 3.2.1.21) that catalyze the hydrolysis of cellobiose to glucose. The term "beta-glucosidase" is further defined herein as a beta-D-glucoside glucohydrolase (E.C. 3.2.1.21), which catalyzes the hydrolysis of terminal non-reducing beta-D-glucose residues with the release of beta-D-glucose. Beta-glucosidase activity can be determined using any suitable method (See e.g., J. Basic Microbiol., 42: 55-66 [2002]). One unit of beta-glucosidase activity is defined as 1.0 pmole of p-nitrophenol produced per minute at 40° C., pH 5 from 1 mM p-nitrophenyl-beta-D-glucopyranoside as substrate in 100 mM sodium citrate containing 0.01% TWEEN® 20.

As used herein, the term "glycoside hydrolase 61" and "GH61" refers to a category of cellulases that enhance cellulose hydrolysis when used in conjunction with one or more additional cellulases. The GH61 family of cellulases is described, for example, in the Carbohydrate Active Enzymes (CAZY) database (See e.g., Harris et al., Biochem., 49(15): 3305-16 [2010]).

A "hemicellulase" as used herein, refers to a polypeptide that can catalyze hydrolysis of hemicellulose into small polysaccharides such as oligosaccharides, or monomeric saccharides. Hemicelluloses include xylan, glucuonoxylan, arabinoxylan, glucomannan and xyloglucan. Hemicellulases include, for example, the following: endoxylanases, beta-xylosidases, alpha-L-arabinofuranosidases, alpha-D-glucuronidases, feruloyl esterases, coumaroyl esterases, alpha-galactosidases, beta-galactosidases, beta-mannanases, and beta-mannosidases.

As used herein, the terms "xylan degrading activity" and "xylanolytic activity" are defined herein as a biological activity that hydrolyzes xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetylxylan esterases, feruloyl esterases, and alpha-glucuronyl esterases) (See e.g., Biely and Puchard, J. Sci. Food Agr. 86:1636-1647 [2006]; Spanikova and Biely, FEBS Lett., 580: 4597-4601 [2006]; and Herrmann et al., Biochem. J., 321: 375-381 [1997]).

Total xylan degrading activity can be measured by determining the reducing sugars formed from various types of xylan, including oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan (See e.g., Bailey et al., J. Biotechnol., 23:257-270 [1992]). In some embodiments, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 mL reactions, 5 mg/mL substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay (See e.g., Lever, Anal. Biochem., 47:273-279 [1972]).

As used herein the term "xylanase activity" refers to a 1,4-beta-D-xylan-xylohydrolase activity (E.C. 3.2.1.8) that catalyzes the endo-hydrolysis of 1,4-beta-D-xylosidic linkages in xylans. In some embodiments, xylanase activity is determined using birchwood xylan as substrate. One unit of xylanase activity is defined as 1.0 µmole of reducing sugar (measured in glucose equivalents; See e.g., Lever, Anal. Biochem., 47:273-279 [1972]) produced per minute during the initial period of hydrolysis at 50° C., pH 5 from 2 g of birchwood xylan per liter as substrate in 50 mM sodium acetate containing 0.01% TWEEN® 20.

As used herein, the term "beta-xylosidase activity" refers to a beta-D-xyloside xylohydrolase (E.C. 3.2.1.37) that catalyzes the exo-hydrolysis of short beta (1-4)-xylooligosaccharides, to remove successive D-xylose residues from the non-reducing termini. In some embodiments of the present invention, one unit of beta-xylosidase activity is defined as 1.0 µmole of p-nitrophenol produced per minute at 40° C., pH 5 from 1 mM p-nitrophenyl-beta-D-xyloside as substrate in 100 mM sodium citrate containing 0.01% TWEEN® 20.

As used herein, the term "acetylxylan esterase activity" refers to a carboxylesterase activity (EC 3.1.1.72) that catalyses the hydrolysis of acetyl groups from polymeric xylan, acetylated xylose, acetylated glucose, alpha-napthyl acetate, and p-nitrophenyl acetate. In some embodiments of the present invention, acetylxylan esterase activity is determined using 0.5 mM p-nitrophenylacetate as substrate in 50 mM sodium acetate pH 5.0 containing 0.01% TWEEN® 20. One unit of acetylxylan esterase activity is defined as the amount of enzyme capable of releasing 1 pmole of p-nitrophenolate anion per minute at pH 5, 25° C.

As used herein, the term "feruloyl esterase activity" refers to a 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. In some embodiments of the present invention, feruloyl esterase activity is determined using 0.5 mM p-nitrophenylferulate as substrate in 50 mM sodium acetate pH 5.0. One unit of feruloyl esterase activity equals the amount of enzyme capable of releasing 1 μmole of p-nitrophenolate anion per minute at pH 5, 25° C.

As used herein, the term "alpha-glucuronidase activity" refers to an alpha-D-glucosiduronate glucuronohydrolase activity (EC 3.2.1.139) that catalyzes the hydrolysis of an alpha-D-glucuronoside to D-glucuronate and an alcohol. One unit of alpha-glucuronidase activity equals the amount of enzyme capable of releasing 1 pmole of glucuronic or 4-O-methylglucuronic acid per minute at pH 5, 40° C. (See e.g., de Vries, J. Bacteriol., 180:243-249 [1998]).

As used herein the term "alpha-L-arabinofuranosidase activity" refers to an alpha-L-arabinofuranoside arabinofuranohydrolase activity (EC 3.2.1.55) that catalyzes the hydrolysis of terminal non-reducing alpha-L-arabinofuranoside residues in alpha-L-arabinosides. The enzyme activity acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per mL of 100 mM sodium acetate pH 5 in a total volume of 200 μL for 30 minutes at 40° C. followed by arabinose analysis by AMINEX®. HPX-87H column chromatography (Bio-Rad Laboratories, Inc., Hercules, Calif., USA).

Enzymatic lignin depolymerization can be accomplished by lignin peroxidases, manganese peroxidases, laccases and cellobiose dehydrogenases (CDH), often working in synergy. These extracellular enzymes, essential for lignin degradation, are often referred to as "lignin-modifying enzymes" or "LMEs." Three of these enzymes comprise two glycosylated heme-containing peroxidases: lignin peroxidase (LIP); Mn-dependent peroxidase (MNP); and, a copper-containing phenoloxidase laccase (LCC). Although the details of the reaction scheme of lignin biodegradation are not fully understood to date, without being bound by theory, it is suggested that these enzymes employ free radicals for depolymerization reactions.

As used herein, the term "laccase" refers to the copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

As used herein, the term "Mn-dependent peroxidase" refers to peroxidases that require Mn. The enzymatic activity of Mn-dependent peroxidase (MnP) in is dependent on $Mn^{2+}$. Without being bound by theory, it has been suggested that the main role of this enzyme is to oxidize $Mn^{2+}$ to $Mn^{3+}$ (See e.g., Glenn et al. Arch. Biochem. Biophys., 251:688-696 [1986]). Subsequently, phenolic substrates are oxidized by the $Mn^{3+}$ generated.

As used herein, the term "lignin peroxidase" refers to an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalysed oxidation of lignin in vivo (See e.g., Harvey et al., FEBS Lett. 195:242-246 [1986]).

As used herein, the term "glucoamylase" (EC 3.2.1.3) refers to enzymes that catalyze the release of D-glucose from non-reducing ends of oligo- and poly-saccharide molecules. Glucoamylase is also generally considered a type of amylase known as amylo-gludosidase.

As used herein, the term "amylase" (EC 3.2.1.1) refers to starch cleaving enzymes that degrade starch and related compounds by hydrolyzing the alpha-1,4 and/or alpha-1,6 glucosidic linkages in an endo- or an exo-acting fashion. Amylases include alpha-amylases (EC 3.2.1.1); beta-amylases (3.2.1.2), amylo-amylases (EC 3.2.1.3), alpha-glucosidases (EC 3.2.1.20), pullulanases (EC 3.2.1.41), and isoamylases (EC 3.2.1.68). In some embodiments, the amylase is an alpha-amylase.

As used herein, the term "pectinase" refers to enzymes that catalyze the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

As used herein, the term "endo-polygalacturonase" (EC 3.2.1.15) refers to enzymes that catalyze the random hydrolysis of 1,4-alpha-D-galactosiduronic linkages in pectate and other galacturonans. This enzyme may also be referred to as "polygalacturonase pectin depolymerase," "pectinase," "endopolygalacturonase," "pectolase," "pectin hydrolase," "pectin polygalacturonase," "poly-alpha-1,4-galacturonide glycanohydrolase," "endogalacturonase," "endo-D-galacturonase," or "poly(1,4-alpha-D-galacturonide) glycanohydrolase."

As used herein, the term "pectin methyl esterase" (EC 3.1.1.11) refers to enzymes that catalyze the reaction: pectin+n $H_2O$=n methanol+pectate. The enzyme may also been known as "pectin esterase," "pectin demethoxylase," "pectin methoxylase," "pectin methylesterase," "pectase," "pectinoesterase," or "pectin pectylhydrolase."

As used herein, the term "endo-galactanase" (EC 3.2.1.89) refers to enzymes that catalyze the endohydrolysis of 1,4-beta-D-galactosidic linkages in arabinogalactans. The enzyme may also be known as "arabinogalactan endo-1,4-beta-galactosidase," "endo-1,4-beta-galactanase," galactanase," "arabinogalactanase," or "arabinogalactan 4-β-D-galactanohydrolase."

As used herein, the term "pectin acetyl esterase" refers to enzymes that catalyze the deacetylation of the acetyl groups at the hydroxyl groups of GalUA residues of pectin.

As used herein, the term "one endo-pectin lyase" (EC 4.2.2.10) refers to enzymes that catalyze the eliminative cleavage of (1→4)-alpha-D-galacturonan methyl ester to give oligosaccharides with 4-deoxy-6-O-methyl-alpha-D-galact-4-enuronosyl groups at their non-reducing ends. The enzyme may also be known as "pectin lyase," "pectin trans-eliminase," "endo-pectin lyase," "polymethylgalacturonic transeliminase," "pectin methyltranseliminase," "pectolyase," "PL," "PNL," "PMGL," or "(1→4)-6-O-methyl-α-D-galacturonan lyase."

As used herein, the term "pectate lyase" (EC 4.2.2.2) refers to enzymes that catalyze the eliminative cleavage of (1→4)-alpha-D-galacturonan to give oligosaccharides with 4-deoxy-alpha-D-galact-4-enuronosyl groups at their non-reducing ends. The enzyme may also be known as "polygalacturonic transeliminase," "pectic acid transeliminase," "polygalacturonate lyase," "endopectin methyltranseliminase," "pectate transeliminase," "endogalacturonate transeliminase," "pectic acid lyase," "pectic lyase," "alpha-1,4-D-endopolygalacturonic acid lyase," "PGA lyase," "PPase-N," "endo-alpha-1,4-polygalacturonic acid lyase," "polygalacturonic acid lyase," "pectin trans-eliminase," "polygalacturonic acid trans-eliminase," or "(1→4)-alpha-D-galacturonan lyase."

As used herein, the term "alpha-rhamnosidase" (EC 3.2.1.40) refers to enzymes that catalyze the hydrolysis of terminal non-reducing alpha-L-rhamnose residues in alpha-L-rhamnosides or alternatively in rhamnogalacturonan. This enzyme may also be known as "alpha-L-rhamnosidase T," "alpha-L-rhamnosidase N," or "alpha-L-rhamnoside rhamnohydrolase."

As used herein, the term "exo-galacturonase" (EC 3.2.1.82) refers to enzymes that hydrolyze pectic acid from the non-reducing end, releasing digalacturonate. The enzyme may also be known as "exo-poly-alpha-galacturonosidase," "exopolygalacturonosidase," or "exopolygalacturanosidase."

As used herein, the term "exo-galacturan 1,4-alpha galacturonidase" (EC 3.2.1.67) refers to enzymes that catalyze reactions of the following types: (1,4-alpha-D-galacturonide)n+H2O=(1,4-alpha-D-galacturonide)n-i+D-galacturonate. The enzyme may also be known as "poly [1→4) alpha-D-galacturonide]galacturonohydrolase," "exopolygalacturonase," "poly(galacturonate) hydrolase," "exo-D-galacturonase," "exo-D-galacturonanase," "exopoly-D-galacturonase," or "poly(1,4-alpha-D-galacturonide) galacturonohydrolase."

As used herein, the term "exopolygalacturonate lyase" (EC 4.2.2.9) refers to enzymes that catalyze eliminative cleavage of 4-(4-deoxy-α-D-galact-4-enuronosyl)-D-galacturonate from the reducing end of pectate (i.e. de-esterified pectin). This enzyme may be known as "pectate disaccharide-lyase," "pectate exo-lyase," "exopectic acid transeliminase," "exopectate lyase," "exopolygalacturonic acid-trans-eliminase," "PATE," "exo-PATE," "exo-PGL," or "(1→4)-alpha-D-galacturonan reducing-end-disaccharide-lyase."

As used herein, the term "rhamnogalacturonanase" refers to enzymes that hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, the term "rhamnogalacturonan lyase" refers to enzymes that cleave alpha-L-Rhap-(1→4)-alpha-D-GalpA linkages in an endo-fashion in rhamnogalacturonan by beta-elimination.

As used herein, the term "rhamnogalacturonan acetyl esterase" refers to enzymes that catalyze the deacetylation of the backbone of alternating rhamnose and galacturonic acid residues in rhamnogalacturonan.

As used herein, the term "rhamnogalacturonan galacturonohydrolase" refers to enzymes that hydrolyze galacturonic acid from the non-reducing end of strictly alternating rhamnogalacturonan structures in an exo-fashion. This enzyme may also be known as "xylogalacturonan hydrolase."

As used herein, the term "endo-arabinanase" (EC 3.2.1.99) refers to enzymes that catalyze endohydrolysis of 1,5-alpha-arabinofuranosidic linkages in 1,5-arabinans. The enzyme may also be known as "endo-arabinase," "arabinan endo-1, 5-α-L-arabinosidase," "endo-1,5-alpha-L-arabinanase," "endo-alpha-1,5-arabanase," "endo-arabanase," or "1,5-alpha-L-arabinan 1,5-alpha-L-arabinanohydrolase."

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include but are not limited to, cysteine proteases including pepsin, papain and serine proteases including chymotrypsins, carboxypeptidases and metalloendopeptidases.

As used herein, "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

As used herein, the terms "isolated" and "purified" are used to refer to a molecule (e.g., an isolated nucleic acid, polypeptide [including, but not limited to enzymes], etc.) or other component that is removed from at least one other component with which it is naturally associated. Thus, the terms refer to a material that is removed from its original environment (e.g., the natural environment, if it is naturally occurring). It is intended that the term encompass any suitable method for removing at least one component with which the molecule is naturally associated. In some embodiments, the terms also encompass cells that are separated from other cells and/or media components. It is intended that any suitable separation method finds use in the present invention. In some embodiments, a material is said to be "purified" when it is present in a particular composition in a higher or lower concentration than exists in a naturally-occurring or wild-type organism or in combination with components not normally present upon expression from a naturally-occurring or wild-type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still considered to be isolated, in that such vector or composition is not part of its natural environment. In some embodiments, a nucleic acid or protein is said to be purified, for example, if it gives rise to essentially one band in an electrophoretic gel or blot.

The term "isolated," when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions (e.g., promoters and terminators). The identification of associated regions will be evident to one of ordinary skill in the art (See e.g., Dynan and Tijan, Nature 316:774-78 [1985]). The term "an isolated DNA sequence" is alternatively referred to as "a cloned DNA sequence."

The term "isolated," when used in reference to a protein, refers to a protein that is found in a condition other than its native environment. In some embodiments, the isolated protein is substantially free of other proteins, particularly other homologous proteins. An isolated protein is more than about 10% pure, preferably more than about 20% pure, and even more preferably more than about 30% pure, as determined by SDS-PAGE. Further aspects of the invention encompass the protein in a highly purified form (i.e., more than about 40% pure, more than about 60% pure, more than about 70% pure, more than about 80% pure, more than about 90% pure, more than about 95% pure, more than about 97% pure, more than about 98% pure, or even more than about 99% pure), as determined by SDS-PAGE.

By "purification" or "isolation," when used in reference to the cellobiose dehydrogenase, it is meant that the cellobiose dehydrogenase is altered from its natural state by virtue of separating the cellobiose dehydrogenase from some or all of the naturally occurring constituents with which it is associated in nature. This may be accomplished by any suitable method, including art recognized separation techniques, including but not limited to ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis, separation on a gradient or any other suitable methods, to remove whole cells, cell debris, impurities, extraneous proteins, or enzymes undesired in the final composition. It is further possible to then add constituents to the cellobiose dehydrogenase-containing composition which provide additional benefits, for example, activating agents, anti-inhibition agents, desirable ions, compounds to control pH, other enzymes, etc.

As used herein, the phrase "substantially pure polypeptide" refers to a composition in which the polypeptide species is the predominant species present (i.e., on a molar or weight basis, it is more abundant than any other individual macromolecular species in the composition), and is generally a substantially purified composition when the object species comprises at least about 50 percent of the macromolecular species present by mole or % weight. Generally, a substantially pure enzyme composition will comprise about 60% or more, about 70% or more, about 80% or more, about 90% or more, about 95% or more, or about 98% or more of all macromolecular species by mole or % weight present in the composition. Solvent species, small molecules (<500 Daltons), and elemental ion species are not considered macromolecular species.

As used herein, the term "purification process" used in reference to an enzyme mixture encompasses any process that physically removes an undesired component of the enzyme mixture. Thus, in some embodiments, purification processes provided herein include purification methodologies that physically remove cellobiose oxidizing activity the enzyme mixture or vice versa. It is contemplated that any suitable purification process known in the art will find use in the present invention. Indeed, it is not intended that the present invention be limited to any particular purification process.

As used herein, the term "cell-free enzyme mixture" comprises enzymes that have been separated from any cells, including the cells that secreted the enzymes. Cell-free enzyme mixtures can be prepared by any of a variety of methodologies that are known in the art, such as filtration or centrifugation methodologies. In some embodiments, the enzyme mixture can be, for example, partially cell-free, substantially cell-free, or entirely cell-free.

As used herein, "polynucleotide" refers to a polymer of deoxyribonucleotides or ribonucleotides in either single- or double-stranded form, and complements thereof.

A polynucleotide is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences. As is known in the art, DNA can be transcribed by an RNA polymerase to produce RNA, but RNA can be reverse transcribed by reverse transcriptase to produce a DNA. Thus, a DNA molecule can effectively encode an RNA molecule and vice versa.

The terms "protein" and "polypeptide" are used interchangeably herein to refer to a polymer of amino acid residues. In addition, the terms "amino acid" "polypeptide," and "peptide" encompass naturally-occurring and synthetic amino acids, as well as amino acid analogs. Naturally occurring amino acids are those encoded by the genetic code, as well as those amino acids that are later modified (e.g., hydroxyproline, γ-carboxyglutamate, and O-phosphoserine).

As used herein, "protein of interest" and "polypeptide of interest" refer to a protein/polypeptide that is desired and/or being assessed. In some embodiments, the protein of interest is expressed intracellularly, while in other embodiments, it is a secreted polypeptide. In some embodiments, the "protein of interest" or "polypeptide of interest" includes the enzymes of the present invention. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

As used herein, the term "amino acid analogs" refers to compounds that have the same basic chemical structure as a naturally occurring amino acid (i.e., an α-carbon that is bound to a hydrogen, a carboxyl group, an amino group, and an R group, including but not limited to homoserine, norleucine, methionine sulfoxide, and methionine methyl sulfonium). In some embodiments, these analogs have modified R groups (e.g., norleucine) and/or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, the amino acid residue number in a test sequence determined by simply counting from the N-terminus will not necessarily be the same as the number of its corresponding position in the reference sequence. For example, in a case where a test sequence has a deletion relative to an aligned reference sequence, there will be no amino acid in the variant that corresponds to a position in the reference sequence at the site of deletion. Where there is an insertion in an aligned test sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "wild-type sequence" and "naturally-occurring sequence" are used interchangeably herein, to refer to a polypeptide or polynucleotide sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for intervention.

As used herein, "naturally-occurring enzyme" refers to an enzyme having the unmodified amino acid sequence identical to that found in nature (i.e., "wild-type"). Naturally occurring enzymes include native enzymes (i.e., those enzymes naturally expressed or found in the particular microorganism).

As used herein, the term "reference enzyme" refers to an enzyme to which another enzyme of the present invention (e.g., a "test" enzyme) is compared in order to determine the presence of an improved property in the other enzyme being evaluated. In some embodiments, a reference enzyme is a wild-type enzyme. In some embodiments, the reference enzyme is an enzyme to which a test enzyme of the present invention is compared in order to determine the presence of an improved property in the test enzyme being evaluated, including but not limited to improved thermoactivity, improved thermostability, and/or improved stability. In some embodiments, a reference enzyme is a wild-type enzyme.

As used herein, the term "biologically active fragment," refers to a polypeptide that has an amino-terminal and/or carboxy-terminal deletion(s) and/or internal deletion(s), but where the remaining amino acid sequence is identical to the corresponding positions in the sequence to which it is being compared and that retains substantially all of the activity of the full-length polypeptide.

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. A nucleic acid construct, nucleic acid (e.g., a polynucleotide), polypeptide, or host cell is referred to herein as "recombinant" when it is non-naturally occurring, artificial or engineered. "Recombination," "recombining" and generating a "recombined" nucleic acid generally encompass the assembly of at least two nucleic acid fragments. The present invention also provides a recombinant nucleic acid construct comprising at least one CDH polynucleotide sequence that hybridizes under stringent hybridization conditions to the complement of a polynucleotide which encodes a polypeptide having the amino acid sequence of SEQ ID NO:2.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: pre-hybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

Moderately stringent conditions encompass those known in the art and described in various standard texts and include the use of washing solution and hybridization conditions (e.g., temperature, ionic strength and % SDS). An example of moderately stringent conditions involves overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

As used in some embodiments herein, stringent conditions or high stringency conditions utilize: (1) low ionic strength and high temperature for washing, for example 0.015 M sodium chloride/0.0015 M sodium citrate/0.1% sodium dodecyl sulfate at 50° C.; (2) during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, the terms "library of mutants" and "library of variants" used in reference to cells, refer to a population of cells which are identical in most of their genome but include different homologues of one or more genes. Such libraries can be used, for example, to identify genes or operons with improved traits. When used in reference to polypeptides or nucleic acids, "library" refers to a set (i.e., a plurality) of heterogeneous polypeptides or nucleic acids. A library is composed of "members." Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids.

As used herein, the term "starting gene" refers to a gene of interest that encodes a protein of interest that is to be improved, deleted, mutated, and/or otherwise changed using the present invention.

The term "property" and grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, and/or enhancer function), a property affecting RNA processing (e.g., RNA splicing, RNA stability, RNA conformation, and/or post-transcriptional modification), a property affecting translation (e.g., level, regulation, binding of mRNA to ribosomal proteins, and/or post-translational modification). For example, a binding site for a transcription factor, polymerase, regulatory factor, etc., of a nucleic acid may be altered to produce desired characteristics or to identify undesirable characteristics.

The term "property" and grammatical equivalents thereof in the context of a polypeptide (including proteins), as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, $k_m$, $k_{cat}$, $k_{cat}/k_m$ ratio, protein folding, inducing an immune response, not inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc. Indeed, it is not intended that the present invention be limited to any particular property.

As used herein, "similarity" refers to an identical or conservative amino acid substitution thereof as defined below. Accordingly, a change to an identical or conservative substitution for the purposes of similarity is viewed as not comprising a change. A deletion of an amino acid or a non-conservative amino acid substitution is viewed herein as comprising a change. Calculation of percent similarity is performed in the same manner as performed for percent identity.

As used herein, "conservative substitution," as used with respect to amino acids, refers to the substitution of an amino acid with a chemically similar amino acid Amino acid substitutions that do not generally alter the specific activity are well known in the art and are described in numerous textbooks. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these in reverse. As used herein, a conservative substitute for a residue is another residue in the same group.

In some embodiments, conservative amino acid substitution can be a substitution such as the conservative substitutions shown in Table A. The substitutions shown are based on amino acid physical-chemical properties, and as such, are independent of organism. In some embodiments, the conservative amino acid substitution is a substitution listed under the heading of exemplary substitutions.

TABLE A

| Original Residue | Substitutions | |
|---|---|---|
| | Conservative Substitutions | Exemplary Substitutions |
| Ala (A) | val; leu; ile | Val |
| Arg (R) | lys; gln; asn | Lys |
| Asn (N) | gln; his; lys; arg | Gln |
| Asp (D) | Glu | Glu |

TABLE A-continued

| Original Residue | Substitutions | |
|---|---|---|
| | Conservative Substitutions | Exemplary Substitutions |
| Cys (C) | Ser | Ser |
| Gln (Q) | Asn | Asn |
| Glu (E) | Asp | Asp |
| Gly (G) | pro; ala | Ala |
| His (H) | asn; gln; lys; arg | Arg |
| Ile (I) | leu; val; met; ala; phe | Leu |
| Leu (L) | ile; val; met; ala; phe | Ile |
| Lys (K) | arg; gln; asn | Arg |
| Met (M) | leu; phe; ile | Leu |
| Phe (F) | leu; val; ile; ala; tyr | Leu |
| Pro (P) | Ala | Ala |
| Ser (S) | Thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala | Leu |

As used herein, the terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The following nomenclature may be used to describe substitutions in a reference sequence relative to a reference sequence or a variant polypeptide or nucleic acid sequence: "R-#-V," where # refers to the position in the reference sequence, R refers to the amino acid (or base) at that position in the reference sequence, and V refers to the amino acid (or base) at that position in the variant sequence.

The term "amino acid substitution set" or "substitution set" refers to a group of amino acid substitutions. A substitution set can comprise 1, 2, 3, 4, 5, 6, 7, 8, 9, 10, 11, 12, 13, 14, 15, or more amino acid substitutions.

As used herein, "identity" and "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection. In some embodiments, the terms "percent identity," "% identity", "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/more accurate pairwise optimal alignments—DNA/Protein Gap Open Penalty:15/10; DNA/Protein Gap Extension Penalty:6.66/0.1; Protein weight matrix: Gonnet series; DNA weight matrix: Identity.

Two sequences are "aligned" when they are aligned for similarity scoring using a defined amino acid substitution matrix (e.g., BLOSUM62), gap existence penalty and gap extension penalty so as to arrive at the highest score possible for that pair of sequences Amino acid substitution matrices and their use in quantifying the similarity between two sequences are well known in the art (See, e.g., Dayhoff et al., in Dayhoff [ed.], Atlas of Protein Sequence and Structure," Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g., Altschul et al., supra).

The present invention also provides a recombinant nucleic acid construct comprising a CDH polynucleotide sequence that hybridizes under stringent hybridization conditions to the complement of a polynucleotide which encodes a polypeptide having the amino acid sequence of SEQ ID NO:2. Two nucleic acid or polypeptide sequences that have 100% sequence identity are said to be "identical." A nucleic acid or polypeptide sequence is said to have "substantial sequence identity" to a reference sequence when the sequences have at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, or greater sequence identity as determined using the methods described herein, such as BLAST using standard parameters.

As used herein, a "secretion signal peptide" can be a propeptide, a prepeptide or both. For example, the term "propeptide" refers to a protein precursor that is cleaved to yield a "mature protein." The signal peptide is cleaved from the pre-protein by a signal peptidase prior to secretion to result in the "mature" or "secreted" protein. The terms "prepeptide" ad "pre-protein" refer to a polypeptide synthesized with an N-terminal signal peptide that targets it for secretion. Accordingly, a "pre-pro-peptide" is a polypeptide that contains a signal peptide that targets the polypeptide for secretion and which is cleaved off to yield a mature polypeptide. Signal peptides are found at the N-terminus of the protein and are typically composed of between 6 to 136 basic and hydrophobic amino acids.

As used herein, "transcription" and like terms refer to the conversion of the information encoded in a gene to an RNA transcript. Accordingly, a reduction of the transcription level of a cellobiose oxidizing enzyme is a reduction in the amount of RNA transcript of an RNA coding for a cellobiose oxidizing enzyme.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In some embodiments, the DNA construct comprises a sequence of interest (e.g., as an "incoming sequence"). In some embodiments, the sequence is operably linked to additional elements such as control elements (e.g., promoters, etc.). In some embodiments, the DNA construct further comprises at least one selectable marker. In some further embodiments, the DNA construct comprises an incoming sequence flanked by homology boxes. In some further embodiments, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In some other embodiments, the DNA construct comprises non-homologous sequences. Once the DNA construct is assembled in vitro, it may be used to: 1) insert heterologous sequences into a desired target sequence of a host cell; 2) mutagenize a region of the host cell chromosome (i.e., replace an endogenous sequence with a heterologous sequence); 3) delete target genes; and/or 4) introduce a replicating plasmid into the host. In some embodiments, the incoming sequence comprises at least one selectable marker. This sequence can code for one or more proteins of interest. It can have other biological functions. In many cases the incoming sequence comprises at least one selectable marker, such as a gene that confers antimicrobial resistance.

As used herein, a "vector" is a polynucleotide construct for introducing a polynucleotide sequence into a cell. In some embodiments, the vector comprises a suitable control sequence operably linked to and capable of effecting the expression of the polypeptide encoded in the polynucleotide sequence in a suitable host. An "expression vector" has a promoter sequence operably linked to the polynucleotide sequence (e.g., transgene) to drive expression in a host cell, and in some embodiments a transcription terminator sequence. In some embodiments, the vectors are deletion vectors. In some embodiments, vectors comprise polynucleotide sequences that produce small interfering RNA or antisense RNA transcripts that interfere with the translation of a target polynucleotide sequence.

As used herein, a "deletion vector" comprises polynucleotide sequences homologous to a polynucleotide sequences 5' and 3' to a target sequence to be deleted from a host genome so as to direct recombination and replacement of the target sequence with a polynucleotide between the 5' and 3' targeting sequences.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell. In general the term, "expression" refers to conversion of the information encoded in a gene to the protein encoded by that gene. Thus, a "reduction of the amount of an expressed cellobiose oxidizing enzyme" is a reduction in the amount of the cellobiose oxidizing enzyme that is eventually translated by the cell.

As used herein, the term "overexpress" is intended to encompass increasing the expression of a protein to a level greater than the cell normally produces. It is intended that the term encompass overexpression of endogenous, as well as heterologous proteins. In some embodiments, overexpression includes an elevated transcription rate and/or level of the gene compared to the endogenous transcription rate and/or level for that gene. For example, in some embodiments, a heterologous gene is introduced into a fungal cell to express a gene encoding a heterologous enzyme such as a beta-glucosidase from another organism. In some other embodiments, a heterologous gene is introduced into a fungal cell to overexpress a gene encoding a homologous enzyme such as a beta-glucosidase.

In some embodiments, the heterologous gene is a gene that has been modified to overexpress the gene product. In some embodiments, "overexpression" refers to any state in which a gene is caused to be expressed at an elevated rate or level as compared to the endogenous expression rate or level for that gene. In some embodiments, overexpression includes elevated translation rate and/or level of the gene compared to the endogenous translation rate and/or level for that gene.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, a "cellobiose dehydrogenase that is secreted by a cell" is a cellobiose dehydrogenase produced by the cell in a manner such that the cellobiose dehydrogenase is exported across a cell membrane and then subsequently released into the extracellular milieu, such as into culture media.

As used herein, a "polynucleotide sequence that has been adapted for expression" is a polynucleotide sequence that has been inserted into an expression vector or otherwise modified to contain regulatory elements necessary for expression of the polynucleotide in the host cell, positioned in such a manner as to permit expression of the polynucleotide in the host cell. Such regulatory elements required for expression include promoter sequences, transcription initiation sequences and, optionally, enhancer sequences. For example, in some embodiments, a polynucleotide sequence is inserted into a plasmid adapted for expression in the fungal host cell.

As used herein, the term "plasmid" refers to a circular double-stranded (ds) DNA construct used as a cloning vector. In some embodiments, plasmids form an extrachromosomal self-replicating genetic element in some eukaryotes and/or prokaryotes, while in some other embodiments, plasmids integrate into the host cell chromosome.

As used herein, a "control sequence" includes all components, which are necessary or advantageous for the expression of a polynucleotide of the present disclosure. Each control sequence may be native or foreign to the polynucleotide of interest. Such control sequences include, but are not limited to, leaders, polyadenylation sequences, propeptide sequences, promoters, signal peptide sequences, and transcription terminators.

As used herein, "operably linked" refers to a configuration in which a control sequence is appropriately placed (i.e., in a functional relationship) at a position relative to a polynucleotide of interest such that the control sequence directs or regulates the expression of the polynucleotide and/or polypeptide of interest.

As used herein, a nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, an "endogenous" or "homologous" gene refers to a gene (including, but not limited to wild-type) that is found in a parental strain of a host cell (e.g., fungal or bacterial cell). As used herein in making comparisons between nucleic acid sequences, "homologous genes" (or "homologue" genes) refers to genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, a "heterologous enzyme" refers to an enzyme that is encoded by a "heterologous gene." However, it is also contemplated that a heterologous gene encodes an endogenous or homologous enzyme, as described herein. In general, the term "heterologous gene" refers to a gene that occurs in a form not found in a parental strain of the host fungal cell (including but not limited to wild-type). Thus, in some embodiments, a heterologous gene is a gene that is derived from a species that is different from the species of the fungal cell expressing the gene and recognized anamorphs, teleomorphs or taxonomic equivalents of the fungal cell expressing the gene. In some embodiments, a heterologous gene is a modified version of a gene that is endogenous to the host fungal cell, which endogenous gene has been subjected to manipulation and then introduced or transformed into the host cell. For example, in some embodiments, a heterologous gene has an endogenous coding sequence, but has modifications to the promoter sequence. Similarly, in some embodiments, a heterologous gene encodes the same amino acid sequence as an endogenous gene, but has modifications to the codon usage or to noncoding regions such as introns, or a combination thereof. For example, in some embodiments, a heterologous gene comprises modifications to the coding sequence to encode a non-wild type polypeptide. In some other embodiments, a heterologous gene has the same promoter sequence, 5' and 3' untranslated regions and coding regions as a parental strain, but be located in another region of the same chromosome, or on an entirely different chromosome as compared to a parental strain of the host cell.

As used herein, the term "introduced" used in the context of inserting a nucleic acid sequence into a cell, means transformation, transduction, conjugation, transfection, and/or any other suitable method(s) known in the art for inserting nucleic acid sequences into host cells. Any suitable means for the introduction of nucleic acid into host cells find use in the present invention.

As used herein, the terms "transformed" and "transformation" used in reference to a cell refer to a cell that has a non-native nucleic acid sequence integrated into its genome or has an episomal plasmid that is maintained through multiple generations. In some embodiments, the terms "transformed" and "stably transformed" refer to a cell that has a non-native (i.e., heterologous) polynucleotide sequence integrated into its genome or as an episomal plasmid that is maintained for at least two generations.

As used herein, the terms "host cell" and "host strain" refer to suitable hosts for expression vectors comprising polynucleotide sequences (e.g., DNA) as provided herein. In some embodiments, the host cells are prokaryotic or eukaryotic cells that have been transformed or transfected with vectors constructed using recombinant techniques as known in the art. Transformed hosts are capable of either replicating vectors encoding at least one protein of interest and/or expressing the desired protein of interest. In addition, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, etc. In some embodiments, host cells are genetically modified to have characteristics that improve protein secretion, protein stability or other properties desirable for expression and/or secretion of a protein. For example, knockout of Alp1 function results in a cell that is protease deficient. Knockout of pyr5 function results in a cell with a pyrimidine deficient phenotype. In some embodiments, host cells are modified to delete endogenous cellulase protein-encoding sequences or otherwise eliminate expression of one or more endogenous cellulases. In some embodiments, expression of one or more endogenous cellulases is inhibited to increase production of cellulases of interest. Genetic modification can be achieved by any suitable genetic engineering techniques and/or classical microbiological techniques (e.g., chemical or UV mutagenesis and subsequent selection). Using recombinant technology, nucleic acid molecules can be introduced, deleted, inhibited or modified, in a manner that results in increased yields of enzyme within the organism or in the culture. For example, knockout of Alp1 function results in a cell that is protease deficient. Knockout of pyr5 function results in a cell with a pyrimidine deficient phenotype. In some genetic engineering approaches, homologous recombination is used to induce targeted gene modifications by specifically targeting a gene in vivo to suppress expression of the encoded protein. In an alternative approach, siRNA, antisense, and/or ribozyme technology finds use in inhibiting gene expression.

The terms "modified sequence" and "modified genes" are used interchangeably herein to refer to a sequence that includes a deletion, insertion, substitution or any other interruption of a naturally occurring nucleic acid sequence. In some embodiments, the expression product of the modified sequence is a truncated protein (e.g., if the modification is a deletion or interruption of the sequence). In some embodiments, the truncated protein retains biological activity. In some alternative embodiments, the expression product of the modified sequence is an elongated protein (e.g., modifications comprising an insertion into the nucleic acid sequence). In some further embodiments, an insertion leads to a truncated protein (e.g., when the insertion results in the formation of a stop codon). Thus, an insertion may result in either a truncated protein or an elongated protein as an expression product.

As used herein, the terms "mutant nucleic acid sequence," "mutant nucleotide sequence," and "mutant gene" are used interchangeably in reference to a nucleotide sequence that has an alteration in at least one codon occurring in a host cell's wild-type nucleotide sequence. The expression product of the mutant sequence is a protein with an altered amino acid sequence relative to the wild-type. In some embodiments, the expression product has an altered functional capacity (e.g., enhanced enzymatic activity).

As used herein, the term "targeted randomization" refers to a process that produces a plurality of sequences where one or several positions have been randomized. In some embodiments, randomization is complete (i.e., all four nucleotides, A, T, G, and C can occur at a randomized position). In some alternative embodiments, randomization of a nucleotide is limited to a subset of the four nucleotides. Targeted randomization can be applied to one or several codons of a sequence, coding for one or several proteins of interest. When expressed, the resulting libraries produce protein populations in which one or more amino acid positions can contain a mixture of all 20 amino acids or a subset of amino acids, as determined by the randomization scheme of the randomized codon. In some embodiments, the individual members of a population resulting from targeted randomization differ in the number of amino acids, due to targeted or random insertion or deletion of codons. In some further embodiments, synthetic amino acids are included in the protein populations produced. In some additional embodiments, the majority of members of a population resulting from targeted randomization show greater sequence homology to the consensus sequence than the starting gene. In some embodiments, the sequence encodes one or more proteins of interest. In some alternative embodiments, the proteins have differing biological functions.

As used herein, "deletion" refers to modification of the polypeptide by removal of one or more amino acids from the reference polypeptide. Deletions can comprise removal of 1 or more amino acids, 2 or more amino acids, 3 or more amino acids, 4 or more amino acids, 5 or more amino acids, 6 or more amino acids, 7 or more amino acids, 8 or more amino acids, 9 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered cellobiose dehydrogenase enzyme. Deletions may be present in the internal portions and/or terminal portions of the polypeptide. In some embodiments, the deletion comprises a continuous segment, while in other embodiments, it is discontinuous.

As used herein, a "gene deletion" or "deletion mutation" is a mutation in which at least part of a sequence of the DNA making up the gene is missing. Thus, a "deletion" in reference to nucleic acids is a loss or replacement of genetic material resulting in a complete or partial disruption of the sequence of the DNA making up the gene. In some embodiments, complete or near-complete deletion of the gene sequence is contemplated. However, a deletion mutation need not completely remove the entire gene sequence for the cellobiose oxidizing enzyme in order to reduce the endogenous cellobiose oxidizing enzyme activity secreted by the fungal cell. For example, a partial deletion that removes one or more nucleotides encoding an amino acid in a cellobiose oxidizing enzyme active site, encoding a secretion signal, or encoding another portion of the cellobiose oxidizing enzyme that plays a role in endogenous cellobiose oxidizing enzyme activity being secreted by the fungal cell. Any number of nucleotides can be deleted, from a single base to an entire piece of a chromosome. Thus, in some embodiments, the term "deletion" refers to the removal of a gene necessary for encoding a specific protein (e.g., cdh1). In this case, the strain having this deletion can be referred to as a "deletion strain."

As used herein, "fragment" refers to a polypeptide that has an amino-terminal and/or carboxy-terminal and/or internal deletion, as compared to a reference polypeptide, but where the remaining amino acid sequence is identical to the corresponding positions in the reference sequence. Fragments can typically have about 80%, about 90%, about 95%, about 98%, or about 99% of the full-length cellobiose dehydrogenase polypeptide, for example the polypeptide of SEQ ID NO:2. In some instances, the sequences of the non-naturally occurring and wild-type cellobiose dehydrogenase polypeptides disclosed herein can include an initiating methionine (M) residue (i.e., M at position 1). However, the skilled artisan will recognize that this initiating methionine residue can be removed during the course of biological processing of the enzyme, such as in a host cell or in vitro translation system, to generate a mature enzyme lacking the initiating methionine residue, but otherwise retaining the enzyme's properties. Thus, for each of the cellobiose dehydrogenase polypeptides disclosed herein having an amino acid sequence comprising an initiating methionine, the present disclosure also encompasses the polypeptide with the initiating methionine residue deleted (i.e., a fragment of the cellobiose dehydrogenase polypeptide lacking a methionine at position 1).

As used herein, a "conditional mutation" is a mutation that has wild-type phenotype under certain environmental conditions and a mutant phenotype under certain other conditions.

As used herein, the term "screening" has its usual meaning in the art and is, in general a multi-step process. In the first step, a mutant nucleic acid or variant polypeptide therefrom is provided. In the second step, a property of the mutant nucleic acid or variant polypeptide is determined. In the third step, the determined property is compared to a property of the corresponding precursor nucleic acid, to the property of the corresponding naturally occurring polypeptide or to the property of the starting material (e.g., the initial sequence) for the generation of the mutant nucleic acid. It will be apparent to the skilled artisan that the screening procedure for obtaining a nucleic acid or protein with an altered property depends upon the property of the starting material, and the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH optima, specificity, etc., before and after mutation, wherein a change indicates an alteration. In some embodiments, the screens are performed in a high-throughput manner, including multiple samples being screened simultaneously, including, but not limited to assays utilizing chips, phage display, multiple substrates and/or indicators, and/or any other suitable method known in the art.

As used in some embodiments, screens encompass selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In some embodiments, a library of variants is exposed to stress (e.g., exposure to heat, protease, or denaturing conditions). Subsequently, variants that are still intact are identified in a screen or enriched by selection. It is intended that the term encompass any suitable means for selection. Indeed, it is not intended that the present invention be limited to any particular method of screening.

As used herein, a "genetically modified" and/or "genetically engineered cell" (e.g., a "genetically engineered fungal cell" and/or a "genetically modified fungal cell") is a cell whose genetic material has been altered using genetic engineering techniques. A genetically modified cell also refers to a derivative of or the progeny of a cell whose genetic material has been altered using genetic engineering techniques. An example of a genetic modification as a result of genetic engineering techniques includes a modification to the genomic DNA; another example of a genetic modification as a result of genetic engineering techniques includes introduction of a stable heterologous nucleic acid into the cell. For example, as provided herein, a genetically modified fungal cell as provided herein is a fungal cell that whose genetic material has been altered in such a way as to either reduce the amount of secreted cellobiose oxidizing enzyme activity, or to reduce the ability of the secreted enzyme to oxidize cellobiose.

In some embodiments, mutant DNA sequences are generated using site saturation mutagenesis in at least one codon. In some other embodiments, site saturation mutagenesis is performed for two or more codons. In some further embodiments, mutant DNA sequences have more than about 50%, more than about 55%, more than about 60%, more than about 65%, more than about 70%, more than about 75%, more than about 80%, more than about 85%, more than about 90%, more than about 95%, or more than about 98% homology with the wild-type sequence. In some alternative embodiments, mutant DNA is generated in vivo using any suitable known mutagenic procedure including, but not limited to the use of radiation, nitrosoguanidine, etc. The desired DNA sequence is then isolated and used in the methods provided herein.

As used herein, the terms "amplification" and "gene amplification" refer to a method by which specific DNA sequences are disproportionately replicated such that the amplified gene becomes present in a higher copy number than was initially present in the genome. In some embodiments, selection of cells by growth in the presence of a drug (e.g., an inhibitor of an inhabitable enzyme) results in the amplification of either the endogenous gene encoding the gene product required for growth in the presence of the drug or by amplification of exogenous (i.e., input) sequences encoding this gene product, or both. "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, that is capable of acting as a synthesis initiation point when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. As known in the art, the exact lengths of the primers will depend on many factors, including temperature, source of primer and the use of the method.

The terms "mutagenic primer" and "mutagenic oligonucleotide" (used interchangeably herein) refer to oligonucleotide compositions which correspond to a portion of a template sequence and which are capable of hybridizing thereto. With respect to mutagenic primers, the primer will not precisely match the template nucleic acid, the mismatch or mismatches in the primer being used to introduce the desired mutation into the nucleic acid library.

As used herein, the terms "non-mutagenic primer" and "non-mutagenic oligonucleotide" (used interchangeably herein) are intended to refer to oligonucleotide compositions which will match precisely to a template nucleic acid. In some embodiments of the invention, only mutagenic primers are used. In some other embodiments, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their precursor sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between about 10-50 bases in length, or more preferably, about 15-45 bases in length. However, it may be necessary to use primers that are either shorter than about 10 bases or longer than about 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added. Primers may be added in a pre-defined ratio according to the present invention. For example, if it is desired that the resulting library have a significant level of a certain specific mutation and a lesser amount of a different mutation at the same or different site, it is possible to produce the desired biased library by adjusting the amount of primer added. Alternatively, by adding lesser or greater amounts of non-mutagenic primers, it is possible to adjust the frequency with which the corresponding mutation(s) are produced in the mutant nucleic acid library.

As used herein, the phrase "contiguous mutations" refers to mutations which are presented within the same oligonucleotide primer. For example, contiguous mutations may be adjacent or nearby each other, however, they will be introduced into the resulting mutant template nucleic acids by the same primer.

As used herein, the phrase "discontiguous mutations" refers to mutations which are presented in separate oligonucleotide primers. For example, discontiguous mutations will be introduced into the resulting mutant template nucleic acids by separately prepared oligonucleotide primers.

As used herein, the term "degenerate codon" refers to a codon used to represent a set of different codons (also referred to as an "ambiguous codon"). For example, the degenerate codon "NNT" represents a set of 16 codons having the base triplet sequence (A, C, T, or G)/(A, C, T, or G)/T.

As used herein, "coding sequence" refers to that portion of a polynucleotide that encodes an amino acid sequence of a protein (e.g., a gene).

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" (PCR) refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This method for amplifying the target sequence is well known in the art.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In some embodiments of the invention, restriction sites are engineered into the selective marker and into 5' and 3' ends of the DNA construct.

As used herein, "homologous recombination" means the exchange of DNA fragments between two DNA molecules or paired chromosomes at the site of identical or nearly identical nucleotide sequences. In some embodiments, chromosomal integration is homologous recombination.

As used herein, the term "C1" refers to *Myceliophthora thermophilia*, including the fungal strain described by Garg (See, Garg, Mycopathol., 30: 3-4 [1966]).

As used herein, "*Chrysosporium lucknowense*" includes the strains described in U.S. Pat. Nos. 6,015,707, 5,811,381 and 6,573,086; US Pat. Pub. Nos. 2007/0238155, US 2008/

0194005, US 2009/0099079; International Pat. Pub. Nos., WO 2008/073914 and WO 98/15633, all of which are incorporated herein by reference, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS143.77, CBS 272.77, CBS122190, CBS122189, and VKM F-3500D. Exemplary C1 derivatives include modified organisms in which one or more endogenous genes or sequences have been deleted or modified and/or one or more heterologous genes or sequences have been introduced. Derivatives include, but are not limited to UV18#100f Δalp1, UV18#100f Δpyr5 Δalp1, UV18#100.f Δalp1 Δpep4 Δalp2, UV18#100.f Δpyr5 Δalp1 Δpep4 Δalp2 and UV18#100.f Δpyr4 Δpyr5 Δalp1 Δpep4 Δalp2, as described in WO 2008073914 and WO 2010107303, each of which is incorporated herein by reference.

As used herein, the term "culturing" refers to growing a population of microbial cells under suitable conditions in a liquid or solid medium. It is contemplated that the culturing be carried out in any suitable format, equipment (e.g., shake flasks, fermentation tanks, bioreactors, etc.). It is also intended that the culturing be conducted using any suitable process methods, including but not limited to batch, fed-batch, and/or continuous culturing. Indeed, it is contemplated that any combination of suitable methods will find use.

In a "batch process," all the necessary materials, with the exception of oxygen for aerobic processes, are placed in a reactor at the start of the operation and the fermentation is allowed to proceed until completion, at which point the product is harvested. In some embodiments, batch processes for producing the fungal cells, enzymes, and/or enzyme mixtures of the present invention are carried out in a shake-flask or a bioreactor.

In a "fed-batch process," the culture is fed continuously or sequentially with one or more media components without the removal of the culture fluid.

In a "continuous process," fresh medium is supplied and culture fluid is removed continuously at volumetrically equal rates to maintain the culture at a steady growth rate. In reference to continuos processes, "steady state" refers to a state in which the concentration of reactants does not vary appreciably, and "quasi-steady state" refers to a state in which, subsequent to the initiation of the reaction, the concentration of reactants fluctuates within a range consistent with normal operation of the continuous hydrolysis process.

As used herein, the term "saccharification" refers to the process in which substrates (e.g., cellulosic biomass) are broken down via the action of cellulases to produce fermentable sugars (e.g. monosaccharides such as but not limited to glucose).

As used herein, the term "fermentable sugars" refers to simple sugars (e.g., monosaccharides, disaccharides and short oligosaccharides), including but not limited to glucose, xylose, galactose, arabinose, mannose and sucrose. Indeed, a fermentable sugar is any sugar that a microorganism can utilize or ferment.

As used herein the term "soluble sugars" refers to water-soluble pentose and hexose monomers and oligomers of up to about six monomer units. It is intended that the term encompass any water soluble mono- and/or oligosaccharides.

As used herein, the term "fermentation" is used broadly to refer to the process of obtaining energy from the oxidation of organic compounds (e.g., carbohydrates). Indeed, "fermentation" broadly refers to the chemical conversion of a sugar source to an end product through the use of a fermenting organism. In some embodiments, the term encompasses cultivation of a microorganism or a culture of microorganisms that use sugars, such as fermentable sugars, as an energy source to obtain a desired product.

As used herein, the term "fermenting organism" refers to any organism, including prokaryotic, as well as eukaryotic organisms (e.g., bacterial organisms, as well as fungal organisms such as yeast and filamentous fungi), suitable for producing a desired end product. Especially suitable fermenting organisms are able to ferment (i.e., convert) sugars, including but not limited to glucose, fructose, maltose, xylose, mannose and/or arabinose, directly or indirectly into at least one desired end product. In some embodiments, yeast that find use in the present invention include, but are not limited to strains of the genus *Saccharomyces* (e.g., strains of *Saccharomyces cerevisiae* and *Saccharomyces uvarum*), strains of the genus *Pichia* (e.g., *Pichia stipitis* such as *Pichia stipitis* CBS 5773 and *Pichia pastoris*), and strains of the genus *Candida* (e.g., *Candida utilis, Candida arabinofermentans, Candida diddensii, Candida sonorensis, Candida shehatae, Candida tropicalis,* and *Candida boidinii*). Other fermenting organisms include, but are not limited to strains of *Zymomonas, Hansenula* (e.g., *Hansenula polymorpha* and *Hansenula anomala*), *Kluyveromyces* (e.g., *Kluyveromyces fragilis*), and *Schizosaccharomyces* (e.g., *Schizosaccharomyces pombe*).

As used herein, the term "slurry" refers to an aqueous solution in which are dispersed one or more solid components, such as a cellulosic substrate. Thus, the term "slurry" refers to a suspension of solids in a liquid. In some embodiments, the cellulosic substrate is slurried in a liquid at a concentration that is thick, but can still be pumped. For example, in some embodiments, the liquid is water, a recycled process stream, and/or a treated effluent. However, it is not intended that the present invention be limited to any particular liquid and/or solid.

The terms "biomass," and "biomass substrate," encompass any suitable materials for use in saccharification reactions. The terms encompass, but are not limited to, materials that comprise cellulose (i.e., "cellulosic biomass," "cellulosic feedstock," and "cellulosic substrate"), as well as lignocellulosic biomass. Indeed, the term "biomass" encompasses any living or dead biological material that contains a polysaccharide substrate, including but not limited to cellulose, starch, other forms of long-chain carbohydrate polymers, and mixtures of such sources. In some embodiments, it is assembled entirely or primarily from glucose or xylose, and in some embodiments, optionally also contains various other pentose and/or hexose monomers. Biomass can be derived from plants, animals, or microorganisms, and includes, but is not limited to agricultural, industrial, and forestry residues, industrial and municipal wastes, and terrestrial and aquatic crops grown for energy purposes. Examples of biomass substrates include, but are not limited to, wood, wood pulp, paper pulp, corn fiber, corn grain, corn cobs, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments, the biomass comprises a mixture of fibers that originate from different biomasses. In some embodiments, the biomass also comprises transgenic plants that express ligninase and/or cellulase enzymes (See e.g., US 2008/0104724 A1).

As used herein, "lignocellulose" refers to a matrix of cellulose, hemicellulose and lignin. Economic production of biofuels from lignocellulosic biomass typically involves conversion of the cellulose and hemicellulose components to fermentable sugars, typically monosaccharides such as glucose (from the cellulose) and xylose and arabinose (from the hemicelluloses). Nearly complete conversion can be achieved by a chemical pretreatment of the lignocellulose followed by enzymatic hydrolysis with cellulase enzymes. The chemical pretreatment step renders the cellulose more susceptible to enzymatic hydrolysis and, in some cases, also hydrolyzes the hemicellulose component. Numerous chemical pretreatment processes are known in the art, and include, but are not limited to, mild acid pretreatment at high temperatures and dilute acid, ammonium pretreatment or organic solvent extraction.

Lignin is a more complex and heterogeneous biopolymer than either cellulose or hemicellulose and comprises a variety of phenolic subunits. Enzymatic lignin depolymerization can be accomplished by lignin peroxidases, manganese peroxidases, laccases and cellobiose dehydrogenases (CDH), often working in synergy. However, as the name suggests, CDH enzymes also oxidize cellobiose to cellobionolactone. Several reports indicate that the oxidation of cellobiose by CDH enhances the rate of cellulose hydrolysis by cellulases by virtue of reducing the concentrations of cellobiose, which is a potent inhibitor of some cellulase components (Mansfield et al., Appl. Environ. Microbiol., 63: 3804-3809 [1997]; and Igarishi et al., Eur. J. Biochem., 253: 101-106 [1998]). Recently, it has been reported that CDHs can enhance the activity of cellulolytic enhancing proteins from Glycosyl Hydrolase family 61 (See e.g., WO2010/080532A1).

As used herein, the term "lignocellulosic biomass" refers to any plant biomass comprising cellulose and hemicellulose, bound to lignin In some embodiments, the biomass is optionally pretreated to increase the susceptibility of cellulose to hydrolysis by chemical, physical and biological pretreatments (such as steam explosion, pulping, grinding, acid hydrolysis, solvent exposure, and the like, as well as combinations thereof).

Various lignocellulosic feedstocks find use, including those that comprise fresh lignocellulosic feedstock, partially dried lignocellulosic feedstock, fully dried lignocellulosic feedstock, and/or any combination thereof. In some embodiments, lignocellulosic feedstocks comprise cellulose in an amount greater than about 20%, more preferably greater than about 30%, more preferably greater than about 40% (w/w). For example, in some embodiments, the lignocellulosic material comprises from about 20% to about 90% (w/w) cellulose, or any amount therebetween, although in some embodiments, the lignocellulosic material comprises less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5% cellulose (w/w). Furthermore, in some embodiments, the lignocellulosic feedstock comprises lignin in an amount greater than about 10%, more typically in an amount greater than about 15% (w/w). In some embodiments, the lignocellulosic feedstock comprises small amounts of sucrose, fructose and/or starch. The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In some embodiments, at least 90% by weight of the particles produced from the size reduction have lengths less than between about 1/16 and about 4 in (the measurement may be a volume or a weight average length). In some embodiments, the equipment used to reduce the particle size is a hammer mill or shredder. Subsequent to size reduction, the feedstock is typically slurried in water, as this facilitates pumping of the feedstock. In some embodiments, lignocellulosic feedstocks of particle size less than about 6 inches do not require size reduction.

As used herein, the term "lignocellulosic feedstock" refers to any type of lignocellulosic biomass that is suitable for use as feedstock in saccharification reactions.

As used herein, the term "pretreated lignocellulosic feedstock," refers to lignocellulosic feedstocks that have been subjected to physical and/or chemical processes to make the fiber more accessible and/or receptive to the actions of cellulolytic enzymes, as described above.

As used herein, the terms "lignocellulose-competent," "lignocellulose-utilizing" and like terms refer to an organism that secretes enzymes that participate in lignin breakdown and hydrolysis. For example, in some embodiments, lignocellulose-competent fungal cells secrete one or more lignin peroxidases, manganese peroxidases, laccases and/or cellobiose dehydrogenases (CDH). These extracellular enzymes, essential for lignin degradation, are often referred to as "lignin-modifying enzymes" or "LMEs."

A biomass substrate is said to be "pretreated" when it has been processed by some physical and/or chemical means to facilitate saccharification. As described further herein, in some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis.

In some embodiments, the substrate is slurried prior to pretreatment. In some embodiments, the consistency of the slurry is between about 2% and about 30% and more typically between about 4% and about 15%. In some embodiments, the slurry is subjected to a water and/or acid soaking operation prior to pretreatment. In some embodiments, the slurry is dewatered using any suitable method to reduce steam and chemical usage prior to pretreatment. Examples of dewatering devices include, but are not limited to pressurized screw presses (See e.g., WO 2010/022511, incorporated herein by reference) pressurized filters and extruders.

In some embodiments, the pretreatment is carried out to hydrolyze hemicellulose, and/or a portion thereof present in lignocellulose to monomeric pentose and hexose sugars (e.g., xylose, arabinose, mannose, galactose, and/or any combination thereof). In some embodiments, the pretreatment is carried out so that nearly complete hydrolysis of the hemicellulose and a small amount of conversion of cellulose to glucose occurs. In some embodiments, an acid concentration in the aqueous slurry from about 0.02% (w/w) to about 2% (w/w), or any amount therebetween, is typically used for the treatment of the cellulosic substrate. Any suitable acid finds use in these methods, including but not limited to, hydrochloric acid, nitric acid, and/or sulfuric acid. In some embodiments, the acid used during pretreatment is sulfuric acid. Steam explosion is one method of performing acid pretreatment of biomass substrates (See e.g., U.S. Pat. No. 4,461,648). Another method of pretreating the slurry involves continuous pretreatment (i.e., the cellulosic biomass is pumped though a reactor continuously). This methods are well-known to those skilled in the art (See e.g., U.S. Pat. No. 7,754,457).

In some embodiments, alkali is used in the pretreatment. In contrast to acid pretreatment, pretreatment with alkali may not hydrolyze the hemicellulose component of the biomass. Rather, the alkali reacts with acidic groups present on the hemicellulose to open up the surface of the substrate. In some embodiments, the addition of alkali alters the crystal structure of the cellulose so that it is more amenable to hydrolysis. Examples of alkali that find use in the pretreatment include, but are not limited to ammonia, ammonium hydroxide, potassium hydroxide, and sodium hydroxide. One method of alkali pretreatment is Ammonia Freeze Explosion, Ammonia Fiber Explosion or Ammonia Fiber Expansion ("AFEX" process; See e.g., U.S. Pat. Nos. 5,171,592; 5,037,663; 4,600,590; 6,106,888; 4,356,196; 5,939,544; 6,176,176; 5,037,663; and 5,171,592). During this process, the cellulosic substrate is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. In some embodiments, the flashed ammonia is then recovered using methods known in the art. In some alternative methods, dilute ammonia pretreatment is utilized. The dilute ammonia pretreatment method utilizes more dilute solutions of ammonia or ammonium hydroxide than AFEX (See e.g., WO 2009/045651 and US 2007/0031953). This pretreatment process may or may not produce any monosaccharides.

An additional pretreatment process for use in the present invention includes chemical treatment of the cellulosic substrate with organic solvents, in methods such as those utilizing organic liquids in pretreatment systems (See e.g., U.S. Pat. No. 4,556,430). These methods have the advantage that the low boiling point liquids easily can be recovered and reused. Other pretreatments, such as the Organosolv™ process, also use organic liquids (See e.g., U.S. Pat. No. 7,465, 791). Subjecting the substrate to pressurized water may also be a suitable pretreatment method (See e.g., Weil et al., Appl. Biochem. Biotechnol., 68: 21-40 [1997]). In some embodiments, the pretreated cellulosic biomass is processed after pretreatment by any of several steps, such as dilution with water, washing with water, buffering, filtration, or centrifugation, or any combination of these processes, prior to enzymatic hydrolysis, as is familiar to those skilled in the art.

The pretreatment produces a pretreated feedstock composition (e.g., a "pretreated feedstock slurry") that contains a soluble component including the sugars resulting from hydrolysis of the hemicellulose, optionally acetic acid and other inhibitors, and solids including unhydrolyzed feedstock and lignin. In some embodiments, the soluble components of the pretreated feedstock composition are separated from the solids to produce a soluble fraction. In some embodiments, the soluble fraction, including the sugars released during pretreatment and other soluble components (e.g., inhibitors), is then sent to fermentation. However, in some embodiments in which the hemicellulose is not effectively hydrolyzed during the pretreatment one or more additional steps are included (e.g., a further hydrolysis step(s) and/or enzymatic treatment step(s) and/or further alkali and/or acid treatment) to produce fermentable sugars. In some embodiments, the separation is carried out by washing the pretreated feedstock composition with an aqueous solution to produce a wash stream and a solids stream comprising the unhydrolyzed, pretreated feedstock. Alternatively, the soluble component is separated from the solids by subjecting the pretreated feedstock composition to a solids-liquid separation, using any suitable method (e.g., centrifugation, microfiltration, plate and frame filtration, cross-flow filtration, pressure filtration, vacuum filtration, etc.). Optionally, in some embodiments, a washing step is incorporated into the solids-liquids separation. In some embodiments, the separated solids containing cellulose, then undergo enzymatic hydrolysis with cellulase enzymes in order to convert the cellulose to glucose. In some embodiments, the pretreated feedstock composition is fed into the fermentation process without separation of the solids contained therein. In some embodiments, the unhydrolyzed solids are subjected to enzymatic hydrolysis with cellulase enzymes to convert the cellulose to glucose after the fermentation process. In some embodiments, the pretreated cellulosic feedstock is subjected to enzymatic hydrolysis with cellulase enzymes.

As used herein, the term "chemical treatment" refers to any chemical pretreatment that promotes the separation and/or release of cellulose, hemicellulose, and/or lignin.

As used herein, the term "physical pretreatment" refers to any pretreatment that promotes the separation and/or release of cellulose, hemicellulose, and/or lignin from cellulosic material.

As used herein, the term "mechanical pretreatment" refers to any mechanical means for treating biomass, including but not limited to various types of grinding or milling (e.g., dry milling, wet milling, or vibratory ball milling).

As used herein, the term "biological pretreatment" refers to any biological pretreatment that promotes the separation and/or release of cellulose, hemicellulose, and/or lignin from cellulosic material.

As used herein, the term "recovered" refers to the harvesting, isolating, collecting, or recovering of protein from a cell and/or culture medium. In the context of saccharification, it is used in reference to the harvesting of fermentable sugars produced during the saccharification reaction from the culture medium and/or cells. In the context of fermentation, it is used in reference to harvesting the fermentation product from the culture medium and/or cells. Thus, a process can be said to comprise "recovering" a product of a reaction (such as a soluble sugar recovered from saccharification) if the process includes separating the product from other components of a reaction mixture subsequent to at least some of the product being generated in the reaction.

As used herein, "increasing" the yield of a product (such as a fermentable sugar) from a reaction occurs when a particular component of interest is present during the reaction (e.g., enzyme) causes more product to be produced, compared with a reaction conducted under the same conditions with the same substrate and other substituents, but in the absence of the component of interest (e.g., without enzyme).

As used herein, a reaction is said to be "substantially free" of a particular enzyme if the amount of that enzyme compared with other enzymes that participate in catalyzing the reaction is less than about 2%, about 1%, or about 0.1% (wt/wt).

As used herein, "fractionating" a liquid (e.g., a culture broth) means applying a separation process (e.g., salt precipitation, column chromatography, size exclusion, and filtration) or a combination of such processes to provide a solution in which a desired protein (e.g., a cellulase enzyme, and/or a combination thereof) comprises a greater percentage of total protein in the solution than in the initial liquid product.

As used herein, the term "enzymatic hydrolysis," refers to the hydrolysis of a substrate by an enzyme. In some embodiments, the hydrolysis comprises methods in which at least one enzyme is contacted with at least one substrate to produce an end product. In some embodiments, the enzymatic hydrolysis methods comprise at least one cellulase and at least one glycosidase enzyme and/or a mixture glycosidases that act on polysaccharides, (e.g., cellulose), to convert all or a portion thereof to fermentable sugars. "Hydrolyzing" and/or "hydrolysis" of cellulose or other polysaccharide occurs when at least some of the glycosidic bonds between two monosaccharides present in the substrate are hydrolyzed, thereby detaching from each other the two monomers that were previously bonded.

It is intended that the enzymatic hydrolysis be carried out with any suitable type of enzyme(s) capable of hydrolyzing at least one substrate to at least one end-product. In some embodiments, the substrate is cellulose, while in some other embodiments, it is lignocelluloses, and in still further embodiments, it is another composition (e.g., starch). In some embodiments, the end-product comprises at least one fermentable sugar. It is further intended that the enzymatic hydrolysis encompass processes carried out with any suitable type of cellulase enzymes capable of hydrolyzing the cellulose to glucose, regardless of their source. It is intended that any suitable source of enzyme will find use in the present invention, including but not limited to enzymes obtained from fungi, such as *Trichoderma* spp., *Aspergillus* spp., *Hypocrea* spp., *Humicola* spp., *Neurospora* spp., *Orpinomyces* spp., *Gibberella* spp., *Emericella* spp., *Chaetomium* spp., *Chrysosporium* spp., *Fusarium* spp., *Penicillium* spp., *Magnaporthe* spp., *Phanerochaete* spp., *Trametes* spp., *Lentinula edodes*, *Gleophyllum trabeiu*, *Ophiostoma piliferum*, *Corpinus cinereus*, *Geomyces pannorum*, *Cryptococcus laurentii*, *Aureobasidium pullulans*, *Amorphotheca resinae*, *Leucosporidium scotti*, *Cunninghamella elegans*, *Thermomyces lanuginosus*, *Myceliopthora thermophila*, and *Sporotrichum thermophile*, as well as those obtained from bacteria of the genera *Bacillus*, *Thermomyces*, *Clostridium*, *Streptomyces* and *Thermobifida*.

In some embodiments, the enzymatic hydrolysis is carried out at a pH and temperature that is at or near the optimum for the cellulase enzymes being used. For example, in some embodiments, the enzymatic hydrolysis is carried out at about 30° C. to about 75° C., or any suitable temperature therebetween, for example a temperature of about 30° C., about 35° C., about 40° C., about 45° C., about 50° C., about 55° C., about 60° C., about 65° C., about 70° C., about 75° C., or any temperature therebetween, and a pH of about 3.5 to about 7.5, or any pH therebetween (e.g., about 3.5, about 4.0, about 4.5, about 5.0, about 5.5, about 6.0, about 6.5, about 7.0, about 7.5, or any suitable pH therebetween). In some embodiments, the initial concentration of cellulose, prior to the start of enzymatic hydrolysis, is preferably about 0.1% (w/w) to about 20% (w/w), or any suitable amount therebetween (e.g., about 0.1%, about 0.5%, about 1%, about 2%, about 4%, about 6%, about 8%, about 10%, about 12%, about 14%, about 15%, about 18%, about 20%, or any suitable amount therebetween). In some embodiments, the combined dosage of all cellulase enzymes is about 0.001 to about 100 mg protein per gram cellulose, or any suitable amount therebetween (e.g., about 0.001, about 0.01, about 0.1, about 1, about 5, about 10, about 15, about 20, about 25, about 30, about 40, about 50, about 60, about 70, about 80, about 90, about 100 mg protein per gram cellulose or any amount therebetween). The enzymatic hydrolysis is carried out for any suitable time period. In some embodiments, the enzymatic hydrolysis is carried out for a time period of about 0.5 hours to about 200 hours, or any time therebetween (e.g., about 2 hours to about 100 hours, or any suitable time therebetween). For example, in some embodiments, it is carried out for about 0.5, about 1, about 2, about 5, about 7, about 10, about 12, about 14, about 15, about 20, about 25, about 30, about 35, about 40, about 45, about 50, about 55, about 60, about 65, about 70, about 75, about 80, about 85, about 90, about 95, about 100, about 120, about 140, about 160, about 180, about 200, or any suitable time therebetween.

In some embodiments, the enzymatic hydrolysis is batch hydrolysis, continuous hydrolysis, and/or a combination thereof. In some embodiments, the hydrolysis is agitated, unmixed, or a combination thereof. The enzymatic hydrolysis is typically carried out in a hydrolysis reactor. The cellulase enzyme composition is added to the pretreated lignocellulosic substrate prior to, during, or after the addition of the substrate to the hydrolysis reactor. Indeed it is not intended that reaction conditions be limited to those provided herein, as modifications are well-within the knowledge of those skilled in the art. In some embodiments, following cellulose hydrolysis, any insoluble solids present in the resulting lignocellulosic hydrolysate, including but not limited to lignin, are removed using conventional solid-liquid separation techniques prior to any further processing. In some embodiments, these solids are burned to provide energy for the entire process.

As used herein, the "total available cellulose" is the amount (wt %) of cellulose that is accessible to enzymatic hydrolysis. Total available cellulose is typically equal to, or very close to being equal to, the amount of initial cellulose present in a hydrolysis reaction.

As used herein, the "residual cellulose" is the portion (wt %) of the total available cellulose in the hydrolysis mixture that remains unhydrolyzed. Residual cellulose can be measured using any suitable method known in the art. For example, it can be directly measured using IR spectroscopy, or it can be measured by determining the amount of glucose generated by concentrated acid hydrolysis of the residual solids.

As used herein, the "total hydrolyzed cellulose" is the portion of the total available cellulose that is hydrolyzed in the hydrolysis mixture. For example, the total hydrolyzed cellulose can be calculated as the difference between the "total available cellulose" and the "residual cellulose."

As used herein, the "theoretical maximum glucose yield" is the maximum amount (wt %) of glucose that could be produced under given conditions from the total available cellulose.

As used herein, "Gmax" refers to the maximum amount (wt %) of glucose that could be produced from the total hydrolyzed cellulose. Gmax can be calculated, for example, by directly measuring the amount of residual cellulose remaining at the end of a reaction under a given reaction conditions, subtracting the amount of residual cellulose from the total available cellulose to determine the total hydrolyzed cellulose, and then calculating the amount of glucose that could be produced from the total hydrolyzed cellulose.

It will be appreciated by those skilled in the art that when calculating theoretical values such as Gmax and theoretical maximum glucose yield, the mass of two hydrogen atoms and one oxygen atom that are added to the glucose molecule in the course of the hydrolysis reaction are taken into account. For example, when a polymer of "n" glucose units is hydrolyzed, (n−1) units of water are added to the glucose molecules formed in the hydrolysis, so the weight of the glucose produced is about 10% greater than the weight of cellulose consumed in the hydrolysis (e.g., hydrolysis of 1 g cellulose would produce about 1.1 g glucose).

Thus, as an example, where 5 g of total available cellulose is present at the beginning of a hydrolysis reaction, and 2 g of residual cellulose remains after the reaction, the total hydrolyzed cellulose is 3 g cellulose. A theoretical maximum glucose yield of 100% (w/w) under the reaction conditions is about 5.5 g of glucose. Gmax is calculated based on the 3 g of cellulose that was released or converted in the reaction by hydrolysis. Thus, in this example, a Gmax of 100% (w/w) is about 3.3 g of glucose. Cellulose levels, either the total available amount present in the substrate or the amount of unhydrolyzed or residual cellulose, can be quantified by any of a variety of methods known in the art, such as by IR spectroscopy or by measuring the amount of glucose generated by concentrated acid hydrolysis of the cellulose (See e.g., U.S. Pat. Nos. 6,090,595 and 7,419,809).

As used herein, the term "undissolved solids" refers to solid material which is suspended, but not dissolved, in a liquid. As is well known in the art, the concentration of suspended or undissolved solids can be determined by any suitable method (e.g., by filtering a sample of the slurry using glass microfiber filter paper, washing the filter cake with water, and drying the cake overnight at about 105° C.).

As used herein, the terms "unhydrolyzed solids," "unconverted solids," and the like refer to cellulose that is not digested by the cellulase enzyme(s), as well as non-cellulosic, or other, materials that are inert to the cellulase enzyme(s), present in the feedstock.

As used herein, the term "by-product" refers to an organic molecule that is an undesired product of a particular process (e.g., saccharification).

As used herein, the term "antibodies" refers to immunoglobulins. Antibodies include but are not limited to immunoglobulins obtained directly from any species from which it is desirable to obtain antibodies. In addition, the present invention encompasses modified antibodies. The term also refers to antibody fragments that retain the ability to bind to the epitope that the intact antibody binds and includes polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), and light chain variable region (VL) fragments.

As used herein, the terms "thermally stable" and "thermostable" refer to enzymes of the present invention that retain a specified amount of enzymatic activity after exposure to identified temperatures over a given period of time under conditions prevailing during the use of the enzyme, for example, when exposed to altered temperatures. "Altered temperatures" include increased or decreased temperatures. In some embodiments, the enzymes retain at least about 50%, about 60%, about 70%, about 75%, about 80%, about 85%, about 90%, about 92%, about 95%, about 96%, about 97%, about 98%, or about 99% enzymatic activity after exposure to altered temperatures over a given time period, for example, at least about 60 minutes, about 120 minutes, about 180 minutes, about 240 minutes, about 300 minutes, etc.

As used herein, the term "thermophilic fungus" refers to any fungus which exhibits optimum growth at a temperature of at least about 37° C., and generally below about 100° C., such as for example between about 37° C. to about 80° C., between about 37° C. to about 75° C., between about 40° C. to about 65° C., or between about 40° C. to about 60° C. Typically, the optimum growth is exhibited at a temperature of at least about 40° to about 60° C.

As used herein, "solvent stable" refers to a polypeptide that maintains similar activity (more than for example, about 60% to about 80%) after exposure to varying concentrations (e.g., about 5 to about 99%) of a non-aqueous solvent (e.g., isopropyl alcohol, tetrahydrofuran, 2-methyltetrahydrofuran, acetone, toluene, butylacetate, methyl tert-butylether, etc.) for a period of time (e.g., about 0.5 to about 24 hrs) compared to a reference polypeptide.

As used herein, the term "oxidation stable" refers to enzymes of the present invention that retain a specified amount of enzymatic activity over a given period of time under conditions prevailing during the use of the invention, for example while exposed to or contacted with oxidizing agents. In some embodiments, the enzymes retain at least about 50%, about 60%, about 70%, about 75%, about 80%, about 85%, about 90%, about 92%, about 95%, about 96%, about 97%, about 98%, or about 99% enzymatic activity after contact with an oxidizing agent over a given time period, for example, at least about 1 minute, about 3 minutes, about 5 minutes, about 8 minutes, about 12 minutes, about 16 minutes, about 20 minutes, etc.

As used herein, "pH stable" refers to a polypeptide that maintains similar activity (more than for example, about 60% to about 80%) after exposure to low or high pH (e.g., about 4.5 to about 6 or about 8 to about 12) for a period of time (e.g., 0.5-24 hrs) compared to a reference polypeptide.

As used herein, the term "enhanced stability" in the context of an oxidation, chelator, thermal and/or pH stable enzyme refers to a higher retained enzymatic activity over time as compared to other enzymes and/or wild-type enzymes.

As used herein, the term "diminished stability" in the context of an oxidation, chelator, thermal and/or pH stable enzyme refers to a lower retained enzymatic activity over time as compared to other enzymes and/or wild-type enzymes.

DETAILED DESCRIPTION OF THE INVENTION

The present invention provides improved fungal strains. In some embodiments, the improved fungal strain finds use in hydrolyzing cellulosic material to glucose. As indicated herein, the present invention provides fungal strains that have reduced secreted activity of an endogenous cellobiose dehydrogenase. In some embodiments, the fungal strains secrete enzyme mixtures that improve the yield of fermentable sugars from cellulose. Previous reports have indicated that the oxidation of cellobiose by cellobiose dehydrogenase enhances the rate of cellulose hydrolysis by cellulases. In contrast to the traditional thinking in the art, the present invention surprisingly provides genomic modifications that reduce cellobiose dehydrogenase activity and result in improvement in the yield of fermentable sugars from cellulose. Advantageously, the genetically modified cellulase-producing fungal cells provided herein secrete enzyme mixtures that result in improved yields of fermentable sugars such as glucose from cellulose.

Lignocellulose (also "lignocellulosic biomass") comprises a matrix of cellulose, hemicellulose and lignin. Economic production of biofuels from lignocellulosic biomass typically involves conversion of the cellulose and hemicellulose components to fermentable sugars, typically monosaccharides such as glucose (from the cellulose) and xylose and arabinose (from the hemicelluloses). Nearly complete conversion can be achieved by a chemical pretreatment of the lignocellulose followed by enzymatic hydrolysis with cellulase enzymes. The chemical pretreatment step renders the cellulose more susceptible to enzymatic hydrolysis and in some cases, also hydrolyzes the hemicellulose component. Numerous chemical pretreatment processes known in the art find use in the present invention, and include, but are not limited to, mild acid pretreatment at high temperatures and dilute acid, ammonium pretreatment and/or organic solvent extraction.

Cellulase is typically a mixture of different types of cellulolytic enzymes (e.g., endoglucanases and cellobiohydrolases, the latter are also referred to as "exoglucanases") that act synergistically to break down the cellulose to soluble di- or oligosaccharides such as cellobiose, which are then further hydrolyzed to glucose by beta-glucosidase. Cellulase enzymes are produced by a wide variety of microorganisms. Cellulases, as well as hemicellulases from filamentous fungi and some bacteria are widely exploited for many industrial applications that involve processing of natural fibers to sugars.

Lignin is a more complex and heterogeneous biopolymer than either cellulose or hemicellulose and comprises a variety of phenolic subunits. Enzymatic lignin depolymerization can be accomplished by lignin peroxidases, manganese peroxidases, laccases, and/or cellobiose dehydrogenases (CDH), often working in synergy. However, as the name suggests, CDH enzymes also oxidize cellobiose to cellobionolactone. Several reports indicate that the oxidation of cellobiose by CDH enhances the rate of cellulose hydrolysis by cellulases by virtue of reducing the concentrations of cellobiose, which is a potent inhibitor of some cellulase components (See e.g., Mansfield et al., Appl. Environ. Microbiol., 63: 3804-3809 [1997]; and Igarishi et al., Eur. J. Biochem., 253:101-106 [1998]). Recently, it has been reported that CDHs can enhance the activity of cellulolytic enhancing proteins from Glycosyl Hydrolase family 61 (See e.g., WO2010/080532A1).

Among the cellulase-producing filamentous fungi, there are those that also produce a variety of enzymes involved in lignin degradation. For example, organisms of such genera as *Myceliophthora*, *Chrysosporium*, *Sporotrichum*, *Thielavia*, *Phanerochaete* and *Trametes* produce and secrete a mixture of cellulases, hemicellulases and lignin degrading enzymes. These types of organisms are commonly called "white rot fungi" by virtue of their ability to digest lignin and to distinguish them from the "brown rot" fungi (such as *Trichoderma*) which typically cannot digest lignin.

Genetically Modified Fungal Cells

The genetically modified fungal cells provided herein permit a reduction in the amount of endogenous cellobiose dehydrogenase activity that is secreted by the cell. In some genetically modified fungal cells provided herein, the cellobiose dehydrogenase activity secreted by the cell is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the level of cellobiose dehydrogenase activity secreted by the unmodified parental fungal cell grown or cultured under essentially the same culture conditions. In some embodiments, a genetically modified fungal cell provides at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more, relative to the level of cellobiose dehydrogenase activity secreted by the unmodified parental fungal cell grown or cultured under essentially the same conditions.

It will be readily appreciated that any suitable genetic modification known in the art can be employed to reduce the secreted activity of the endogenous cellobiose dehydrogenase. For example, as described below, modifications contemplated herein include modifications that reduce the amount of cellobiose dehydrogenase secreted by the cell. Modifications that reduce the amount of cellobiose dehydrogenase expressed by the cell are also contemplated. Additional embodiments include modifications that reduce the transcription level of cellobiose dehydrogenase. Still further embodiments include the complete or partial deletion of a gene encoding cellobiose dehydrogenase. Other embodiments include modifications that reduce the catalytic efficiency of cellobiose dehydrogenase.

Secreted Enzymes.

In some embodiments, the fungal cells of the present invention have been genetically modified to reduce the amount of the endogenous cellobiose dehydrogenase secreted by the cell. A reduction in the amount of secreted cellobiose dehydrogenase can be a complete or partial reduction of the cellobiose dehydrogenase secreted to the extracellular milieu. Reduction in the amount of secreted cellobiose dehydrogenase can be accomplished by reducing the amount of cellobiose dehydrogenase produced by the cell and/or by reducing the ability of the cell to secrete the cellobiose dehydrogenase produced by the cell. Methods for reducing the ability of the cell to secrete a polypeptide can be performed according to any of a variety of suitable methods known in the art (See e.g., Fass and Engels J. Biol. Chem., 271:15244-15252 [1996], which is incorporated by reference herein in its entirety). For example, the gene encoding a secreted polypeptide can be modified to delete or inactivate a secretion signal peptide. In some embodiments, the fungal cells have been genetically modified to disrupt the N-terminal secretion signal peptide of the cellobiose dehydrogenase. In some embodiments, the amount of cellobiose dehydrogenase secreted by the cell is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the secretion of cellobiose dehydrogenase in an unmodified organism grown or cultured under essentially the same culture conditions.

Furthermore, in some embodiments, the total amount of cellobiose dehydrogenase activity is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the total amount of cellobiose dehydrogenase secreted in an unmodified organism grown or cultured under essentially the same culture conditions.

Decreased secretion of a cellobiose dehydrogenase can be determined by any of a variety of suitable methods known in the art for detection of protein or enzyme levels. For example, the levels of cellobiose dehydrogenase in the supernatant of a fungal culture can be detected using Western blotting techniques or any other suitable protein detection techniques that use an antibody specific to cellobiose dehydrogenase. Similarly, secreted cellobiose dehydrogenase activity in the supernatant of a fungal culture can be measured using assays for cellobiose dehydrogenase activity as described in greater detail herein.

Expression Level.

In some embodiments, the fungal cells have been genetically modified to reduce the amount of the endogenous cellobiose dehydrogenase expressed by the cell. As used herein, expression refers to conversion of the information encoded in a gene to the protein encoded by that gene. Thus, a reduction of the amount of an expressed cellobiose dehydrogenase represents a reduction in the amount of the cellobiose dehydrogenase that is eventually translated by the cell. In some such embodiments, the reduction in the expression is accomplished by reducing the amount of mRNA that is transcribed from a gene encoding cellobiose dehydrogenase. In some other embodiments, the reduction in the expression is accomplished by reducing the amount of protein that is translated from a mRNA encoding cellobiose dehydrogenase.

The amount of cellobiose dehydrogenase expressed by the cell can be reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the expression of cellobiose dehydrogenase in an unmodified fungal cell. In some such embodiments, the reduction in the expression is accomplished by reducing the amount of mRNA that is transcribed from a gene encoding cellobiose dehydrogenase in an unmodified organism grown or cultured under essentially the same culture conditions.

Furthermore, in some embodiments, a reduction in the expression level of a cellobiose dehydrogenase results in at least about 5%, about 10%, about 15%, about 20%, about 25%, about 30%, about 35%, about 40%, about 45%, about 50%, about 55%, about 60%, about 65%, about 70%, about 75%, about 80%, 85% about, 90%, about 91%, about 92%, about 93%, about 94%, about 95%, about 96%, about 97%, about 98%, or about a 99% reduction in the total expression level of cellobiose dehydrogenase activity by the fungal cell relative to an unmodified fungal cell grown or cultured under essentially the same culture conditions.

Decreased expression of a cellobiose dehydrogenase can be determined by any of a variety of methods known in the art for detection of protein or enzyme levels. For example, the levels of cellobiose dehydrogenase in the supernatant of a fungal culture can be detected using Western blotting techniques or any other suitable protein detection techniques that use an antibody specific to cellobiose dehydrogenase.

Methods for reducing expression of a polypeptide are well known and can be performed using any of a variety of suitable methods known in the art. For example, the gene encoding a secreted polypeptide can be modified to disrupt a translation initiation sequence such as a Shine-Delgarno sequence or a Kozak consensus sequence. Furthermore, the gene encoding a secreted polypeptide can be modified to introduce a frameshift mutation in the transcript encoding the endogenous cellobiose dehydrogenase. It will also be recognized that usage of uncommon codons can result in reduced expression of a polypeptide. It will be appreciated that in some embodiments, the gene encoding the cellobiose dehydrogenase has at least one nonsense mutation that results in the translation of a truncated protein.

Other methods of reducing the amount of expressed polypeptide include post-transcriptional RNA silencing methodologies such as antisense RNA and RNA interference. Antisense techniques are well-established, and include using a nucleotide sequence complementary to the nucleic acid sequence of the gene. More specifically, expression of the gene by a fungal cell may be reduced or eliminated by introducing a nucleotide sequence complementary to the nucleic acid sequence, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Methods for expressing antisense RNA are known in the art (See e.g., Ngiam et al., Appl Environ Microbiol., 66(2):775-82 [2000]; and Zrenner et al., Planta., 190(2):247-52 [1993]), both of which are hereby incorporated by reference herein in their entirety).

Furthermore, modification, downregulation or inactivation of the gene may be obtained via RNA interference (RNAi) techniques (See e.g., Kadotani et al. Mol. Plant Microbe Interact., 16:769-76 [2003], which is incorporated by reference herein in its entirety). RNA interference methodologies include double stranded RNA (dsRNA), short hairpin RNAs (shRNAs) and small interfering RNAs (siRNAs). Potent silencing using dsRNA may be obtained using any suitable technique (See e.g., Fire et al., Nature 391:806-11 [1998]). Silencing using shRNAs is also well-established (See e.g., Paddison et al., Genes Dev., 16:948-958 [2002]). Silencing using siRNA techniques are also known (See e.g., Miyagishi et al., Nat. Biotechnol., 20:497-500 [2002]). The content of each of the above-cited references is incorporated by reference herein in its entirety.

Transcription Level.

In some embodiments, the fungal cells of the present invention have been genetically modified to reduce the transcription level of a gene encoding the endogenous cellobiose dehydrogenase. As used herein, transcription and similar terms refer to the conversion of the information encoded in a gene to an RNA transcript. Accordingly, a reduction of the transcription level of a cellobiose dehydrogenase is a reduction in the amount of RNA transcript of an RNA coding for a cellobiose dehydrogenase. In some embodiments, the transcription level is reduced by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to the transcription level of a cellobiose dehydrogenase in an unmodified organism grown or cultured under essentially the same culture conditions.

Furthermore, in some embodiments, a reduction in the transcription level of a cellobiose dehydrogenase results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total cellobiose dehydrogenase secreted by the fungal cell relative to an unmodified organism grown or cultured under essentially the same culture conditions. Decreased transcription can be determined by any of a variety of methods known in the art for detection of transcription levels. For example, the levels of transcription of a particular mRNA in a fungal cell can be detected using quantitative RT-PCR techniques or other RNA detection techniques that specifically detect a particular mRNA. Methods for reducing transcription level of a gene can be performed according to any suitable method known in the art, and include partial or complete deletion of the gene, and disruption or replacement of the promoter of the gene such that transcription of the gene is greatly reduced or even inhibited. For example, the promoter of the gene can be replaced with a weak promoter (See e.g., U.S. Pat. No. 6,933,133, which is incorporated by reference herein in its entirety). Thus, where the weak promoter is operably linked with the coding sequence of an endogenous polypeptide, transcription of that gene is greatly reduced or inhibited.

Gene Deletion.

In some embodiments, the fungal cells of the present invention have been genetically modified to at least partially delete a gene encoding the endogenous cellobiose dehydrogenase. Typically, this deletion reduces or eliminates the total amount of endogenous cellobiose dehydrogenase secreted by the fungal cell. In some embodiments, complete or near-complete deletion of the gene sequence is contemplated. However, a deletion mutation need not completely remove the entire gene sequence encoding cellobiose dehydrogenase, in order to reduce the amount of endogenous cellobiose dehydrogenase secreted by the fungal cell. For example, in some embodiments, there is a partial deletion that removes one or more nucleotides encoding an amino acid in a cellobiose dehydrogenase active site, encoding a secretion signal, or encoding another portion of the cellobiose dehydrogenase that plays a role in endogenous cellobiose dehydrogenase activity being secreted by the fungal cell.

A deletion in a gene encoding cellobiose dehydrogenase in accordance with the embodiments provided herein include a deletion of one or more nucleotides in the gene encoding the cellobiose dehydrogenase. In some embodiments, there is a deletion of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100%, of the gene encoding the cellobiose dehydrogenase, wherein the amount of cellobiose dehydrogenase secreted by the cell is reduced.

Thus, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the activity of the cellobiose dehydrogenase secreted by the fungal cell, relative to the activity of cellobiose dehydrogenase secreted by an unmodified organism grown or cultured under essentially the same culture conditions.

Furthermore, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the total cellobiose dehydrogenase secreted by the fungal cell relative to an unmodified fungal cell grown or cultured under essentially the same culture conditions.

Deletion of a cellobiose dehydrogenase gene can be detected and confirmed by any of a variety of methods known in the art for detection of gene deletions, including the methods provide herein and in the Examples. For example, as exemplified herein, gene deletion can be confirmed using PCR amplification of the modified genomic region. It will be appreciated that additional suitable techniques for confirming deletion can be used and are well known, including Southern blot techniques, DNA sequencing of the modified genomic region, and screening for positive or negative markers incorporated during recombination events.

Methods for complete and/or partial deletion of a gene are well-known and the genetically modified fungal cells described herein can be generated using any of a variety of deletion methods known in the art that result in a reduction in the amount of endogenous cellobiose dehydrogenase secreted by the cells. Such methods may advantageously include standard gene disruption using homologous flanking markers (See e.g., Rothstein, Meth. Enzymol., 101:202-211 [1983], incorporated herein by reference in its entirety). Additional techniques for gene deletion include PCR-based methods for standard deletion (See e.g., Davidson et al., Microbiol., 148:2607-2615 [2002], incorporated herein by reference in its entirety).

Additional gene deletion techniques include "positive-negative" cassettes; cre/lox based deletion, biolistic transformation to increase homologous recombination, and *Agrobacterium*-mediated gene disruption. The "positive-negative" method employs cassettes which consist of one marker gene for positive screening and another marker gene for negative screening (See e.g., Chang et al., Proc. Natl. Acad. Sci. USA 84:4959-4963 [1987]). Cre/lox based methodologies employ elimination of marker genes using expression of Cre recombinase (See e.g., Florea et al., Fung. Genet. Biol., 46:721-730 [2009]).

Methods to introduce DNA or RNA into fungal cells are known to those of skill in the art and include, but are not limited to PEG-mediated transformation of protoplasts, electroporation, biolistic transformation, and *Agrobacterium*-mediated transformation. Biolistic transformation employs a process in which DNA or RNA is introduced into cells on micron-sized particles, thus increasing delivery of a deletion construct to the fungal cell (See e.g., Davidson et al., Fung. Genet. Biol., 29:38-48 [2000]). Similarly, *Agrobacterium*-mediated transformation in conjunction with linear or split-marker deletion cassettes can facilitate delivery of deletion constructs to the target cell (See e.g., Wang et al., Curr. Genet., 56:297-307 [2010]).

Further methods for complete or partial gene deletion include disruption of the gene. Such gene disruption techniques are known to those of skill in the art, including, but not limited to insertional mutagenesis, the use of transposons, and marked integration. However, it will be appreciated that any suitable technique that provides for disruption of the coding sequence or any other functional aspect of a gene finds use in generating the genetically modified fungal cells provided herein. Methods of insertional mutagenesis can be performed according to any suitable method known in the art (See e.g., Combier et al., FEMS Microbiol Lett., 220:141-8 [2003], which is incorporated by reference herein in its entirety). In addition, *Agrobacterium*-mediated insertional mutagenesis can be used to insert a sequence that disrupts the function of the encoded gene, such as disruption of the coding sequence or any other functional aspect of the gene.

Transposon mutagenesis methodologies provide another means for gene disruption. Transposon mutagenesis is well known in the art, and can be performed using in vivo techniques (See e.g., Firon et al., Eukaryot. Cell 2:247-55 [2003]); or by the use of in vitro techniques (See e.g., Adachi et al., Curr. Genet., 42:123-7 [2002]); both of these references are incorporated by reference in their entireties. Thus, targeted gene disruption using transposon mutagenesis can be used to insert a sequence that disrupts the function of the encoded gene, such as disruption of the coding sequence or any other functional aspect of the gene.

Restriction enzyme-mediated integration (REMI) is another methodology for gene disruption, and is well known in the art (See e.g., Thon et al., Mol. Plant Microbe Interact., 13:1356-65 [2000], which is incorporated by reference herein in its entirety). REMI generates insertions into genomic restriction sites in an apparently random manner, some of which cause mutations. Thus, insertional mutants that demonstrate a disruption in the gene encoding the endogenous cellobiose dehydrogenase can be selected and utilized as provided herein.

Catalytic Disruption.

In some other embodiments, the fungal cell has been genetically modified to reduce the catalytic efficiency of the cellobiose dehydrogenase. A reduction in catalytic efficiency refers to a reduction in the activity of cellobiose dehydrogenase, relative to unmodified cellobiose dehydrogenase, as measured using standard techniques, as provided herein or otherwise known in the art. Thus, a genetic modification that reduces catalytic efficiency can result in, for example, a translated protein product that has a reduction in enzymatic activity.

A reduction in catalytic efficiency is a reduction of cellobiose dehydrogenase activity of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or more, relative to unmodified cellobiose dehydrogenase, as measured using standard techniques. In some further embodiments, the genetic modification results in a reduction of cellobiose dehydrogenase activity of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% in the total cellobiose dehydrogenase activity secreted by the fungal cell, as compared to unmodified cellobiose dehydrogenase, as measured using standard techniques.

Methods for reducing catalytic efficiency of dehydrogenases are well known, and as such, any of a variety of suitable methods known in the art for reducing catalytic efficiency find use in genetically modifying the fungal cells provided herein. Thus, for example, the fungal cell can be genetically modified to inactivate one or more residues in an active site of the cellobiose dehydrogenase (See e.g., Frederik et al., Biochem., 42:4049-4056 [2003], incorporated by reference herein in its entirety). For example, one or more residues can be modified to decrease substrate binding, and/or one or more residues can be modified to decrease the catalytic activity of the cellobiose dehydrogenase. Accordingly, one or more residues in the electron acceptor (e.g., flavin) binding domain, or any substrate binding domain of cellobiose dehydrogenase can be performed to reduce or inactivate the catalytic efficiency of the cellobiose dehydrogenase. Similarly, it will be apparent that mutation of residues outside an active site can result in allosteric change in the shape or activity of the cellobiose dehydrogenase, such that the catalytic efficient of the enzyme is reduced.

In some embodiments, other domains are targeted for at least one mutation which results in reducing catalytic efficiency of the endogenous cellobiose dehydrogenase. For example, in some embodiments, a mutation to one or more residues in a heme-binding domain of cellobiose dehydrogenase can result in reduced catalytic efficiency (See e.g., Rotsaert et al., Arch. Biochem. Biophys., 390:206-14 [2001], which is incorporated by reference herein in its entirety).

Fungal Cells

As indicated herein, the present invention provides fungal cells from the family Chaetomiaceae that have been genetically modified to reduce the amount of endogenous cellobiose dehydrogenase activity that is secreted by the cell, where the fungal cell is capable of secreting a cellulase-containing enzyme mixture. The Chaetomiaceae are a family of fungi in the Ascomycota, class Sordariomycetes. The family Chaetomiaceae includes the genera *Achaetomium, Aporothielavia, Chaetomidium, Chaetomium, Corylomyces, Corynascus, Farrowia, Thielavia, Zopfiella*, and *Myceliophthora*. In some embodiments, the genetically modified fungal cell provided herein is a Chaetomiaceae family member selected from *Myceliophthora, Thielavia, Corynascus*, and *Chaetomium*.

In some embodiments, the genetically modified fungal cell is an anamorph or teleomorph of a Chaetomiaceae family member selected from *Myceliophthora, Thielavia, Corynascus*, and *Chaetomium*. In some embodiments, the genetically modified fungal cell is selected from *Sporotrichum, Chrysosporium, Paecilomyces, Talaromyces* and *Acremonium*. It is also contemplated that the genetically modified fungal cell can also be selected from the genera *Ctenomyces, Thermoascus*, and *Scytalidium*, including anamorphs and teleomorphs of fungal cells of these genera. In some embodiments, the genetically modified fungal cell is selected from the strains of *Sporotrichum cellulophilum, Thielavia heterothallica, Corynascus heterothallicus, Thielavia terrestris*, and *Myceliophthora thermophila*, including anamorphs and teleomorphs thereof. It is not intended that the present invention be limited to any particular genus within the Chaetomiaceae family. In some further embodiments, the genetically modified fungal cell is a thermophilic species of *Acremonium, Arthroderma, Corynascus, Thielavia, Myceliophthora, Thermoascus, Chromocleista, Byssochlamys, Sporotrichum, Chaetomium, Chrysosporium, Scytalidium, Ctenomyces, Paecilomyces*, or *Talaromyces*. It will be understood that for all of the aforementioned species, the genetically modified fungal cell presented herein encompasses both the perfect and imperfect states, and other taxonomic equivalents (e.g., anamorphs), regardless of the species name by which they are known (See e.g., Cannon, Mycopathol., 111:75-83 [1990]; Moustafa et al., Persoonia 14:173-175 [1990]; Upadhyay et al., Mycopathol., 87:71-80 [1984]; Guarro et al., Mycotaxon 23: 419-427 [1985]; Awao et al., Mycotaxon 16:436-440 [1983]; and von Klopotek, Arch. Microbiol., 98:365-369 [1974]). Those skilled in the art will readily recognize the identity of appropriate equivalents. Accordingly, it will be understood that, unless otherwise stated, the use of a particular species designation in the present disclosure also refers to species that are related by anamorphic or teleomorphic relationship. For example, the following species are anamorphs or teleomorphs and may therefore be considered as synonymous: *Myceliophthora thermophila, Sporotrichum thermophile, Sporotrichum thermophilum, Sporotrichum cellulophilum, Chrysosporium thermophile, Corynascus heterothallicus,* and *Thielavia heterothallica.*

In some embodiments, the genetically modified fungal cells provided herein are cellulase-producing fungal cells. In some embodiments, the cellulase-producing fungal cells express and secrete a mixture of cellulose hydrolyzing enzymes. In some embodiments, the genetically modified fungal cells provided herein are fungal cells from the family Chaetomiaceae that secrete two or more cellulose hydrolyzing enzymes (e.g., endoglucanase, cellobiohydrolase, and/or beta-glucosidase). In some additional embodiments, the cellulase-producing fungal cells produce two or more of these enzymes, in any combination.

Additionally, in some embodiments, the genetically modified fungal cell is derived from a lignocellulose-competent parental fungal cell. In some embodiments, lignocellulose-competent fungal cells secrete one or more lignin peroxidases, manganese peroxidases, laccases and/or cellobiose dehydrogenases (CDH).

The present invention also provides a fungal culture in a vessel comprising a genetically modified fungal cell as described hereinabove. In some embodiments, the vessel comprises a liquid medium, such as fermentation medium. For example, the vessel can be a flask, bioprocess reactor, or any suitable container. In some embodiments, the vessel comprises a solid growth medium. For example, the solid medium can be an agar medium such as potato dextrose agar, carboxymethylcellulose, cornmeal agar, and any other suitable medium. In some embodiments, the fungal cell described hereinabove is an isolated fungal cell.

Cellobiose Dehydrogenase

As indicated herein, the terms "cellobiose dehydrogenase" and "CDH" refer to a cellobiose:acceptor 1-oxidoreductase that catalyzes the conversion of cellobiose in the presence of an acceptor to cellobiono-1,5-lactone and a reduced acceptor. Examples of cellobiose dehydrogenases fall into the enzyme classification (E.C. 1.1.99.18). Typically 2,6-dichloroindophenol can act as acceptor, as can iron, especially Fe(SCN)$_3$, molecular oxygen, ubiquinone, or cytochrome C, and other polyphenolics, such as lignin. Substrates of the enzyme include cellobiose, cello-oligosaccharides, lactose, and D-glucosyl-1,4-β-D-mannose, glucose, maltose, mannobiose, thiocellobiose, galactosyl-mannose, xylobiose, xylose. Electron donors include beta-1-4 dihexoses with glucose or mannose at the reducing end, though alpha-1-4 hexosides, hexoses, pentoses, and beta-1-4 pentomers can act as substrates for at least some of these enzymes (See e.g, Henriksson et al., Biochim. Biophys. Acta Prot. Struct. Mol. Enzymol., 1383: 48-54 [1998]; and Schou et al., Biochem. J., 330: 565-571 [1998]).

In some embodiments, a CDH enzyme contains both the conserved glucose-methanol-choline (GMC) oxido-reductase N and the GMC oxido-reductase C domains. In some other embodiments, a CDH contains the GMC oxido-reductase N domain alone. The GMC oxidoreductases are FAD flavoprotein oxidoreductases (See e.g., Cavener, J. Mol. Biol., 223:811-814 [1992]; and Vrielink and Blow, Biochem., 32:11507-15 [1993]). The GMC oxidoreductases include a variety of proteins, such as choline dehydrogenase, methanol oxidase, and cellobiose dehydrogenase (CDH), which share a number of regions with sequence similarities. One of these regions, located in the N-terminal section, corresponds to the FAD ADP-binding domain, as further defined by the Pfam database under the entry GMC_oxred_N (PF00732). Similarly, the C-terminal conserved domain (GMC oxido-reductase C domain) is defined as set forth in the Pfam database under the entry GMC_oxred_C (PF05199).

Cellobiose dehydrogenases can be categorized into two families. The first family contains a catalytic portion and the second family contains a catalytic portion and a cellulose binding motif (CBM). The 3-dimensional structure of an exemplary cellobiose dehydrogenase features two globular domains, each containing one of two cofactors, namely a heme or a flavin. The active site lies at a cleft between the two domains. Oxidation of cellobiose typically occurs via 2-electron transfer from cellobiose to the flavin, generating cellobiono-1,5-lactone and reduced flavin. The active FAD is regenerated by electron transfer to the heme group, leaving a reduced heme. The native state heme is regenerated by reaction with the oxidizing substrate at the second active site. In some embodiments, the acceptor is preferentially iron ferricyanide, cytochrome C, or an oxidized phenolic compound such as dichloroindophenol (DCIP), an acceptor commonly used for colorimetric assays. Metal ions and $O_2$ are also acceptors, but for most cellobiose dehydrogenases the reaction rate of cellobiose oxidase for these acceptors is several orders of magnitude lower than that observed for iron or organic oxidants. Following cellobionolactone release, the product may undergo spontaneous ring-opening to generate cellobionic acid (See e.g., Hallberg et al., J. Biol. Chem., 278:7160-7166 [2003]). Those of skill in the art will appreciate that cellobiose dehydrogenase enzyme activity typically employs the presence of oxygen or an equivalent redox acceptor, which may be, for example, lignin, molecular oxygen, cytochrome c, redox dyes, benzoquinones and/or $Fe^{2+}$ complexes.

Cellobiose dehydrogenase activity can be measured using any of a variety of suitable methods known in the art (See e.g., Schou et al., Biochem J., 220:565-71 [1998], which is incorporated by reference in its entirety). For example, DCPIP (2,6-dichlorophenolindophenol) reduction by CDH activity in the presence of cellobiose can be monitored by absorbance at 530 nm.

As provided herein, a fungal cell that has been genetically modified to reduce the secreted activity of a cellobiose dehydrogenase typically has reduced secreted activity of an endogenous cellobiose dehydrogenase. Accordingly, one or more cellobiose dehydrogenase enzymes from each of the fungal species described herein can be targeted for genetic modification. In some embodiments, the cellobiose dehydrogenase is from a fungal species in the family Chaetomiaceae. Some examples of cellobiose dehydrogenase enzymes identified from Chaetomiaceae family members are set forth in Table 1, below. In some embodiments, the cellobiose dehydrogenase is from a fungal species selected from *Sporotrichum cellulophilum, Thielavia heterothallica, Corynascus heterothallicus, Thielavia terrestris, Chaetomium globosum* and *Myceliophthora thermophila*. Some cellobiose dehydrogenase enzymes identified from these species are set forth in the table below. The proteins listed in the table below are examples of cellobiose dehydrogenase that are known in the art, or identified herein as being a cellobiose dehydrogenase.

TABLE 1

Cellobiose Dehydrogenase Sequences

| Accession Number | Organism | GMC oxred N Domain | GMC oxred C Domain |
|---|---|---|---|
| AAC26221 | *Myceliophthora thermophila* | 251-554 | 645-781 |
| XP_001229896.1 | *Chaetomium globosum* CBS 148.51 | 226-529 | 620-757 |
| JGIThite5441 | *Thielavia terrestris* | 253-555 | 647-783 |
| JGIThite4524 | *Thielavia terrestris* | 36-337 | NA |
| XP_001225932.1 | *Chaetomium globosum* CBS 148.51 | 36-338 | NA |
| JGIThite6738 | *Thielavia terrestris* | 249-550 | 642-779 |
| CDH2 derived from a C1 strain | *Myceliophthora thermophila* | 249-550 | NA |
| XP_001226549.1 | *Chaetomium globosum* CBS 148.51 | 249-521 | 549-667 |

*Accession numbers for *Thielavia terrestris* refer to the U.S. Department of Energy (DOE) Joint Genome Institute (JGI) genome sequence Certain amino acid sequences encoding cellobiose dehydrogenase are provided herein. For example, the nucleotide sequence encoding *Myceliophthora thermophila* CDH1 is set forth herein as SEQ ID NO:1, and the encoded amino acid sequence of *Myceliophthora thermophila* CDH1 is set forth as SEQ ID NO:2.

In some embodiments, the cellobiose dehydrogenase is cellobiose dehydrogenase EC 1.1.99.18. In some embodiments, the cellobiose dehydrogenase is a cellobiose dehydrogenase with the amino acid sequence of *Myceliophthora thermophila* CDH1 as set forth in SEQ ID NO:2. In some other embodiments, the cellobiose dehydrogenase comprises an amino acid sequence provided in the GenBank entry of any one of the accession numbers set forth in Table 1. In some embodiments, the cellobiose dehydrogenase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:1. In some embodiments, the cellobiose dehydrogenase is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a nucleic acid sequence encoding the amino acid sequence set forth as SEQ ID NO:2, or an amino acid sequence provided in the GenBank entry of any one of the accession numbers set forth in Table 1. In some embodiments, the cellobiose dehydrogenase is encoded by a nucleic acid sequence that can selectively hybridize to SEQ ID NO:1, under moderately stringent or stringent conditions, as described hereinabove. In some embodiments, the cellobiose dehydrogenase is encoded by a nucleic acid sequence that can selectively hybridize under moderately stringent or stringent conditions to a nucleic acid sequence that encodes SEQ ID NO:2, or an amino acid sequence provided in the GenBank entry of any one of the accession numbers set forth in Table 1.

In some embodiments, the cellobiose dehydrogenase comprises an amino acid sequence with at least about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85% about 86%, about 87%, about 88%, about 89%, about 90%, about 91%, about 92%, about 93%, about 94%, about 95%, about 96%, about 97%, about 98%, about 99%, or about 100% similarity to the amino acid sequence set forth as SEQ ID NO:2, or an amino acid sequence provided in the GenBank entry of any one of the accession numbers set forth in Table 1. Cellobiose dehydrogenase sequences can be identified by any of a variety of methods known in the art. For example, a sequence alignment can be conducted against a database, for example against the NCBI database, and sequences with the lowest HMM E-value can be selected.

In some embodiments, the fungal cells of the present invention have been genetically modified to reduce the amount of cellobiose dehydrogenase activity from two or more endogenous cellobiose dehydrogenase enzymes secreted by the cell. In some embodiments, a first of the two or more cellobiose dehydrogenases comprises an amino acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO:2, and a second of the two or more cellobiose dehydrogenase enzymes comprises an amino acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 2.

Enzyme Mixtures

Also provided herein are enzyme mixtures that comprise at least one or more cellulose hydrolyzing enzymes expressed by a fungal cell that has been genetically modified to reduce the amount of endogenous cellobiose dehydrogenase activity secreted by the cell, as described herein. Cellulase enzymes are produced by a wide variety of microorganisms. Cellulases (and hemicellulases) from filamentous fungi and some bacteria are widely exploited for many industrial applications that involve processing of natural fibers to sugars. It is contemplated that mixtures of any enzymes set forth herein will find use in the present invention.

In some embodiments, the enzyme mixture comprises at least one or more cellulose hydrolyzing enzymes expressed by a fungal cell that has been genetically modified to reduce the amount of endogenous cellobiose dehydrogenase activity that is secreted by the cell, as described herein. In some embodiments, the fungal cell is a lignocellulose-utilizing cell from the family Chaetomiaceae. In some embodiments, the genetically modified fungal cell provided herein is a Chaetomiaceae family member selected from *Myceliophthora, Thielavia, Corynascus*, or *Chaetomium*. In some other embodiments, the genetically modified fungal cell can also be an anamorph or teleomorph of a Chaetomiaceae family member selected from *Myceliophthora, Thielavia, Corynascus*, or *Chaetomium*. In addition, the genetically modified fungal cell can also be selected from *Sporotrichum* or *Acremonium* or *Talaromyces*. It is also contemplated that the genetically modified fungal cell be selected from *Ctenomyces, Thermoascus*, and *Scytalidium*, including anamorphs and teleomorphs of fungal cells from those genera. In some embodiments, the fungal cell is a species selected from *Sporotrichum cellulophilum, Thielavia heterothallica, Corynascus heterothallicus, Thielavia terrestris, Chaetomium globosum Talaromyces stipitatus* and *Myceliophthora thermophila*, including anamorphs and teleomorphs thereof.

In addition to the enzymes described above, other enzymes such as laccases find use in the mixtures of the present invention. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

Mn-dependent peroxidases also find use in the mixtures of the present invention. The enzymatic activity of Mn-dependent peroxidase (MnP) in is dependent on $Mn^{2+}$. Without being bound by theory, it has been suggested that the main role of this enzyme is to oxidize $Mn^{2+}$ to $Mn^{3+}$ (See e.g., Glenn et al. Arch. Biochem. Biophys., 251:688-696 [1986]). Subsequently, phenolic substrates are oxidized by the $Mn^{3+}$ generated.

Lignin peroxidases also find use in the mixtures of the present invention. Lignin peroxidase is an extracellular heme that catalyzes the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalysed oxidation of lignin in vivo (See e.g., Harvey et al., FEBS Lett., 195:242-246 [1986]).

In some embodiments, it may be advantageous to utilize an enzyme mixture that is cell-free. A cell-free enzyme mixture typically comprises enzymes that have been separated from any cells, including the cells that secreted the enzymes. Cell-free enzyme mixtures can be prepared using any of a variety of suitable methodologies that are known in the art (e.g., filtration or centrifugation). In some embodiments, the enzyme mixture is partially cell-free, substantially cell-free, or entirely cell-free.

In some embodiments, two or more cellulases and any additional enzymes present in the cellulase enzyme mixture are secreted from a single genetically modified fungal cell or by different microbes in combined or separate fermentations. Similarly, two or more cellulases and any additional enzymes present in the cellulase enzyme mixture may be expressed individually or in sub-groups from different strains of different organisms and the enzymes combined in vitro to make the cellulase enzyme mixture. It is also contemplated that the cellulases and any additional enzymes in the enzyme mixture are expressed individually or in sub-groups from different strains of a single organism, and the enzymes combined to make the cellulase enzyme mixture.

In some embodiments, the enzyme mixture comprises at least one or more cellulose hydrolyzing enzymes expressed by a fungal cell that has been genetically modified to reduce the amount of endogenous cellobiose dehydrogenase activity that is secreted by the cell, as described herein. In some embodiments, the fungal cell is a lignocellulose-utilizing cell from the family Chaetomiaceae. In some embodiments, the genetically modified fungal cell provided herein is a Chaetomiaceae family member selected from *Myceliophthora, Thielavia, Corynascus*, and *Chaetomium*. The genetically modified fungal cell can also be an anamorph or teleomorph of a Chaetomiaceae family member selected from *Myceliophthora, Thielavia, Corynascus*, and *Chaetomium*. In addition, the genetically modified fungal cell can also be selected from *Sporotrichum, Acremonium, Ctenomyces, Scytalidium* and *Thermoascus*, including anamorphs and teleomorphs of fungal cells from these genera. In some embodiments, the fungal cell is a species selected from *Sporotrichum cellulophilum, Thielavia heterothallica, Corynascus heterothallicus, Thielavia terrestris, Chaetomium globosum, Talaromyces stipitatus*, and *Myceliophthora thermophila*, including anamorphs and teleomorphs thereof.

In some embodiments, the cellulase enzyme mixture of the present invention is produced in a fermentation process in which the fungal cells described herein are grown in submerged liquid culture fermentation. In some embodiments, submerged liquid fermentations of fungal cells are incubated using batch, fed-batch or continuous processing. In a batch process, all the necessary materials, with the exception of oxygen for aerobic processes, are placed in a reactor at the start of the operation and the fermentation is allowed to proceed until completion, at which point the product is harvested. In some embodiments, batch processes for producing the enzyme mixture of the present invention are carried out in a shake-flask or a bioreactor. In some embodiments in which a fed-batch process is used, the culture is fed continuously or sequentially with one or more media components without the removal of the culture fluid. In continuous processes, fresh medium is supplied and culture fluid is removed continuously at volumetrically equal rates to maintain the culture at a steady growth rate. Those of skill in the art will appreciate that fermentation medium is typically liquid, and comprises a carbon source, a nitrogen source as well as other nutrients, vitamins and minerals which can be added to the fermentation media to improve growth and enzyme production of the fungal cells. These other media components may be added prior to, simultaneously with or after inoculation of the culture with the fungal cells.

In some embodiments of the process for producing the enzyme mixture of the present invention, the carbon source comprises a carbohydrate that will induce the expression of the cellulase enzymes from the fungal cell. For example, in some embodiments, the carbon source comprises one or more of cellulose, cellobiose, sophorose, xylan, xylose, xylobiose, and/or related oligo- or poly-saccharides known to induce expression of cellulases and beta-glucosidase in such fungal cells. In some embodiments utilizing batch fermentation, the carbon source is added to the fermentation medium prior to or simultaneously with inoculation. In some embodiments utilizing fed-batch or continuous operations, the carbon source is supplied continuously or intermittently during the fermentation process. For example, in some embodiments, the carbon source is supplied at a carbon feed rate of between about 0.2 and about 2.5 g carbon/L of culture/h, or any suitable amount therebetween.

The methods for producing the enzyme mixture of the present invention may be carried at any suitable temperature, typically from about 20° C. to about 100° C., or any suitable temperature therebetween, for example from about 20° C. to about 80° C., 25° C. to about 65° C., or any suitable temperature therebetween, or from about 20° C., about 22° C., about 25° C., about 26° C., about 27° C., about 28° C., about 29° C., about 30° C., about 32° C., about 35° C., about 37° C., about 40° C., about 45° C., about 50° C., about 55° C., about 60° C., about 65° C., about 70° C., about 75° C., about 80° C., about 85° C, about 90° C., about 95° C., and/or any suitable temperature therebetween.

The methods for producing enzyme mixture of the present invention may be carried out at any suitable pH, typically from about 3.0 to 8.0, or any suitable pH therebetween, for example from about pH 3.5 to pH 6.8, or any suitable pH therebetween, for example from about pH 3.0, about 3.2, about 3.4, about 3.5, about 3.7, about 3.8, about 4.0, about 4.1, about 4.2, about 4.3, about 4.4, about 4.5, about 4.6, about 4.7, about 4.8, about 4.9, about 5.0, about 5.2, about 5.4, about 5.5, about 5.7, about 5.8, about 6.0, about 6.2, about 6.5, about 6.8, about 7.0, about 7.2, about 7.5, about 8.0, or any suitable pH therebetween.

In some embodiments, the enzyme mixture is contained in a vessel comprising a genetically modified fungal cell as described herein. In some embodiments, the vessel comprises a liquid medium. In some embodiments, the vessel is a flask, bioprocess reactor, or any other suitable container. In some embodiments, the enzyme mixture is in a liquid volume. In some embodiments, the liquid volume can be greater than about 0.01 mL, about 0.1 mL, about 1 mL, about 10 mL, about 100 mL, about 1000 mL, or greater than about 10 L, about 50 L, about 100 L, about 200 L, about 300 L, about 400 L, about 500 L, about 600 L, about 700 L, about 800 L, about 900 L, about 1000 L, about 10,000 L, about 50,000 L, about 100,000 L, about 250,000 L, about 500,000 L or greater than about 1,000,000 L.

In some embodiments, following fermentation, the fermentation medium containing the fungal cells is used, or the fermentation medium containing the fungal cells and the enzyme mixture is used, or the enzyme mixture is separated from the fungal cells, for example by filtration or centrifugation, and the enzyme mixture in the fermentation medium is used. In some embodiments, low molecular solutes such as unconsumed components of the fermentation medium are removed by ultrafiltration. In some embodiments, the enzyme mixture is concentrated by evaporation, precipitation, sedimentation, filtration, or any suitable means. In some embodiments, chemicals such as glycerol, sucrose, sorbitol, etc., are added to stabilize the enzyme mixture. In some embodiments, other chemicals, such as sodium benzoate or potassium sorbate, are added to the enzyme mixture to prevent growth of microbial contaminants Methods for Generating Glucose The present invention also provides processes for generating glucose, comprising contacting cellulose with the enzyme mixture described herein. For example, in some embodiments, the process comprises contacting cellulose with an enzyme mixture comprising two or more cellulose hydrolyzing enzymes, wherein at least one of the two or more cellulose hydrolyzing enzymes is expressed by a fungal cell as described herein. In some embodiments, the method for generating glucose from cellulose using the enzyme mixture is batch hydrolysis, continuous hydrolysis, or a combination thereof. In some embodiments, the hydrolysis is agitated, unmixed, or a combination thereof.

The methods for generating glucose from cellulose may be carried out at any suitable temperature, including between about 30° C. and about 80° C., or any suitable temperature therebetween, for example a temperature of about 30° C., about 35° C., about 40° C., about 45° C., about 50° C., about 55° C., about 60° C., about 65° C., about 70° C., about 75° C., about 80° C. or any suitable temperature therebetween, and a pH of about 3.0 to about 8.0, or any suitable pH therebetween, for example at a pH of about 3.0, about 3.5, about 4.0, about 4.5, about 5.0, about 5.5, about 6.0, about 6.5, about 7.0, about 7.5, about 8.0, or any suitable pH therebetween. The initial concentration of cellulose in the hydrolysis reactor, prior to the start of hydrolysis, is preferably about 0.1% (w/w) to about 15% (w/w), or any suitable amount therebetween, for example about 2, about 4, about 6, about 8, about 10, about 12, about 14, about 15%, or any suitable amount therebetween.

The dosage of the cellulase enzyme mixture may be about 0.1 to about 100 mg protein per gram cellulose, or any suitable amount therebetween, for example about 0.1, about 0.5, about 1, about 5, about 10, about 15, about 20, about 25, about 30, about 40, about 50, about 60, about 70, about 80, about 90, about 100 mg protein per gram cellulose or any suitable amount therebetween. The hydrolysis may be carried out for a time period of about 0.5 hours to about 200 hours, or any suitable time therebetween. For example, in some embodiments, the hydrolysis is carried out for a period of about 15 hours to about 100 hours, or any time therebetween, or it may be carried out for about 0.5 hour, about 1 hour, about 2 hours, about 4 hours, about 8 hours, about 12 hours, about 15 hours, about 20 hours, about 25 hours, about 30 hours, about 35 hours, about 40 hours, about 45 hours, about 50 hours, about 55 hours, about 60 hours, about 65 hours, about 70 hours, about 75 hours, about 80 hours, about 85 hours, about 90 hours, about 95 hours, about 100 hours, about 120 hours, about 140 hours, about 160 hours, about 180 hours, about 200 hours, or any suitable time therebetween. It should be appreciated that the reaction conditions are not meant to limit the invention in any manner and may be adjusted as desired by those of skill in the art.

In some embodiments, the enzymatic hydrolysis is typically carried out in a hydrolysis reactor. The enzyme mixture is added to the pretreated lignocellulosic feedstock (also referred to as the "substrate") prior to, during, or after the addition of the substrate to the hydrolysis reactor.

In methods of contacting cellulosic material with an enzyme mixture, various environmental conditions may be adjusted according to any variety of methods known in the art in order to maximize the formation of a hydrolysis product such as glucose. For example, temperature, pH, % dissolved oxygen, and stirring speed can each be independently adjusted. In some embodiments, the enzyme mixture is a cell-free mixture, as described herein.

The methods for generating glucose, as described herein, using the enzyme mixture with reduced cellobiose dehydrogenase activity result in a higher yield of glucose from the enzymatically hydrolyzed cellulose than a corresponding process using an enzyme mixture with its full complement of cellobiose dehydrogenase activity. Further, such methods result in decreased conversion of the cellobiose products in the enzymatic hydrolysate to oxidized products.

In some embodiments of the methods using the genetically modified cells and/or enzyme mixtures provided herein, improved glucose yield can be measured and quantified. As described herein, glucose yield can be described in terms of the amount of generated glucose per theoretical maximum glucose yield, or in terms of Gmax. It will be appreciated by those skilled in the art that when calculating theoretical values such as Gmax and theoretical maximum glucose yield, the mass of two hydrogen atoms and one oxygen atom that are added to the glucose molecule in the course of the hydrolysis reaction is taken into account. For example, when a polymer of "n" glucose units is hydrolyzed, (n−1) units of water are added to the glucose molecules formed in the hydrolysis, so the weight of the glucose produced is about 10% greater than the weight of cellulose consumed in the hydrolysis (e.g., hydrolysis of 1 g cellulose produces about 1.1 g glucose). Thus, as an example, where 5 g of total available cellulose is present at the beginning of a hydrolysis reaction, and 2 g of residual cellulose remains after the reaction, the total hydrolyzed cellulose is 3 g cellulose. A theoretical maximum glucose yield of 100% (w/w) under the reaction conditions is about 5.5 g of glucose. Gmax is calculated based on the 3 g of cellulose that was released or converted in the reaction by hydrolysis. Thus, in this example, a Gmax of 100% (w/w) is about 3.3 g of glucose. Cellulose levels, either the total available amount present in the substrate or the amount of unhydrolyzed or residual cellulose, can be quantified by any of a variety of suitable methods known in the art, such as by IR spectroscopy or by measuring the amount of glucose generated by concentrated acid hydrolysis of the cellulose (See e.g., U.S. Pat. Nos. 6,090,595 and 7,419,809, both of which are incorporated by reference herein in their entireties).

For example, in some embodiments, the cellulose content is determined by acid hydrolysis of the cellulose, followed by glucose concentration determination, taking into account the water necessary to hydrolyze the cellulose (See e.g., U.S. Pat. Nos. 6,090,595 and 7,419,809). In one example, a slurry of feedstock is centrifuged, washed with water, and suspended in sulfuric acid at a net sulfuric acid concentration of 70%. The slurry is incubated at 40° C. for 30 minutes, followed by dilution in deionized water to 2% sulfuric acid. At this time point, the samples are steam-autoclaved at 121° C. for 1 hour, to convert the oligomers to monomeric glucose. The glucose concentration is measured by HPLC or any suitable enzymatic assay. In some alternative embodiments, the cellulose content is analyzed by infrared spectroscopy as described in Example 1. For example, solids can be washed and placed on the detection crystal of an infrared spectrometer and the absorbance measured between 500-4000 $cm^{-1}$.

Glucose levels can be quantified by any of a variety of suitable methods known in the art (See e.g., U.S. Pat. Nos. 6,090,595 and 7,419,809). For example, glucose concentrations can be determined using a coupled enzymatic assay based on glucose oxidase and horseradish peroxidase (See e.g., Trinder, Ann. Clin. Biochem., 6:24-27 [1969], which is incorporated herein by reference in its entirety). Additional methods of glucose quantification include chromatographic methods (See e.g., U.S. Pat. Nos. 6,090,595 and 7,419,809). Cellobiose levels can be measured by any number of suitable HPLC methods known to those of skill in the art (See e.g., Kotiranta et al., Appl. Biochem. Biotechnol., 81:81-90 [1999]), which is incorporated herein by reference in its entirety).

Similarly, decreased conversion of cellobiose and glucose products to oxidized products such as cellobionolactone and gluconolactone can be quantified by any of a variety of suitable methods known in the art. For example, products of glucose or cellobiose oxidation can be detected and quantified using infrared spectroscopy, or by chromatographic methodologies such as HPLC (See e.g., Rakotomanga et al., J. Chromatog. B., 4:277-284 [1991]; and Mansfield et al., Appl. Environ. Microbiol., 64:3804-3809 [1997], both of which are incorporated herein by reference in their entireties).

Accordingly, total oxidation of glucose or cellobiose can be determined, for example, as a function of total oxidation products per theoretical maximum glucose yield, or as a function of Gmax.

Cellulosic Material

Any material containing cellulose finds use in the present invention. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. Cellulosic material can be, but is not limited to, herbaceous material, agricultural residue, forestry residue, municipal solid waste, waste paper, and pulp and paper mill residue (See e.g., Wiselogel et al., in Charles E. Wyman, (ed.), *Handbook on Bioethanol*, Taylor & Francis, Washington D.C. [1995], at pp. 105-118; Wyman, Biores. Technol., 50:3-16 [1994]; Lynd, Appl. Biochem. Biotechnol., 24/25: 695-719 [1990]; and Mosier et al., Adv. Biochem. Eng. Biotechnol., 65:23-40 [1999]). It is understood that in some embodiments, the cellulose is in the form of lignocellulose, a plant cell wall material containing lignin, cellulose, and hemicellulose in a mixed matrix. In some embodiments, the cellulosic material is lignocellulose.

A pretreated lignocellulosic feedstock is a material of plant origin that, prior to pretreatment, contains at least 10% cellulose (dry weight), more preferably greater than about 30% cellulose, even more preferably greater than 40% cellulose, for example about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%. about 42%, about 43%, about 44%, about 45%, about 46%, about 47%, about 48%, about 49%, about 50%, about 55%, about 60%, about 65%, about 70%, about 75%, about 80%, about 85%, about 90%, about 95%, or any suitable percent therebetween, and at least about 10% lignin (dry weight), or at least about 12% (dry weight) and that has been subjected to physical and/or chemical processes to make the fiber more accessible and/or receptive to the actions of cellulolytic enzymes. In some embodiments, the lignocellulosic feedstock may contain higher levels of cellulose after pretreatment. For example, if acid pretreatment is employed, the hemicellulose component is hydrolyzed, which increases the relative level of cellulose. In this case, the pretreated feedstock may contain greater than about 20% cellulose and greater than about 12% lignin.

Lignocellulosic feedstocks that find use in the invention include, but are not limited to, agricultural residues such as corn stover, wheat straw, barley straw, rice straw, oat straw, canola straw, sugarcane straw and soybean stover; fiber process residues such as corn fiber, sugar beet pulp, pulp mill fines and rejects or sugar cane bagasse; forestry residues such as aspen wood, other hardwoods, softwood, and sawdust; or grasses such as switch grass, miscanthus, cord grass, and reed canary grass. In some embodiments, the lignocellulosic feedstock is first subjected to size reduction by any of a variety of methods including, but not limited to, milling, grinding, agitation, shredding, compression/expansion, and/or other types of mechanical action. Size reduction by mechanical action can be performed by any type of equipment adapted for the purpose, for example, but not limited to, a hammer mill.

Pretreatment.

In some embodiments, a substrate of the enzyme mixture comprises pretreated cellulosic material. Thus, for example, in some methods described herein, any pretreatment process known in the art can be used to disrupt plant cell wall components of cellulosic material (See e.g., Chandra et al., Adv. Biochem. Engin. Biotechnol., 108: 67-93 [2007]; Galbe and Zacchi, Adv. Biochem. Engin. Biotechnol., 108: 41-65 [2007]; Hendriks and Zeeman, Biores. Technol., 100: 10-18 [2009]; Mosier et al., Biores. Technol., 96: 673-686 [2005]; Taherzadeh and Karimi, Int. J. Mol. Sci., 9:1621-1651 [2008]; and Yang and Wyman, Biofuels Bioprod. Bioref. Biofpr. 2: 26-40 [2008]; all of which are hereby incorporated by reference in their entireties).

In some embodiments, the cellulosic material is subjected to particle size reduction, pre-soaking, wetting, washing, or conditioning prior to pretreatment using any of a variety of suitable methods known in the art. Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber expansion, dilute ammonia pretreatment, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments. In some embodiments, the cellulosic material is pretreated before hydrolysis and/or fermentation. In some embodiments, pretreatment is preferably performed prior to the hydrolysis. In some alternative embodiments, pretreatment is carried out simultaneously with enzyme hydrolysis to release fermentable sugars, such as glucose, xylose, and/or cellobiose. In some embodiments, the pretreatment step itself results in some conversion of biomass to fermentable sugars, even in absence of enzymes.

Steam Pretreatment.

In steam pretreatment, cellulosic material is heated to disrupt the plant cell wall components, including lignin, hemicellulose, and cellulose to make the cellulose and other fractions (e.g., hemicelluloses), accessible to enzymes. Cellulosic material is passed to or through a reaction vessel where steam is injected to increase the temperature to the required temperature and pressure and is retained therein for the desired reaction time. In some embodiments, steam pretreatment is preferably done at about 140° C. to about 230° C., while in other embodiments it is done at about 160° C. to about 200° C., and in additional embodiments, it is done at about 170° C. to about 190° C., where the optimal temperature range depends on any addition of a chemical catalyst. In some embodiments, residence time for the steam pretreatment is about 1 to about 15 minutes, while in other embodiments it is about 3 to about 12 minutes, and in still other embodiments, it is about 4 to about 10 minutes, where the optimal residence time depends on temperature range and any addition of a chemical catalyst. Steam pretreatment allows for relatively high solids loadings, so that cellulosic material is generally only moist during the pretreatment. Steam pretreatment is often combined with an explosive discharge of the material after the pretreatment, which is known as steam explosion, that is, rapid flashing to atmospheric pressure and turbulent flow of the material to increase the accessible surface area by fragmentation (See e.g., U.S. Pat. No. 4,451,648; Duff and Murray, Biores. Technol., 855:1-33 [1996]; Galbe and Zacchi, Appl. Microbiol. Biotechnol., 59: 618-628 [2002]; and U.S. Patent Appln. Publ. No. 2002/0164730, all of which are incorporated herein by reference in their entireties). During steam pretreatment, hemicellulose acetyl groups are cleaved and the resulting acid autocatalyzes partial hydrolysis of the hemicellulose to monosaccharides and oligosaccharides. Lignin is removed to only a limited extent. A catalyst such as $H_2SO_4$ or $SO_2$ (typically about 0.3 to about 3% w/w) is often added prior to steam pretreatment, which decreases the time and temperature, increases the recovery, and improves enzymatic hydrolysis (See e.g., Ballesteros et al., Appl. Biochem. Biotechnol., 129-132: 496-508 [2006]; Varga et al., Appl. Biochem. Biotechnol., 113-116: 509-523 [2004]; and Sassner et al., Enz. Microb. Technol., 39: 756-762 [2006]).

Chemical Pretreatment:

The term "chemical treatment" refers to any chemical pretreatment that promotes the separation and/or release of cellulose, hemicellulose, and/or lignin. Examples of suitable chemical pretreatment processes include, but are not limited to, dilute acid pretreatment, dilute alkali pretreatment (See e.g., U.S. Pat. Appln. Pub. Nos. 2007/0031918 and 2007/0037259), lime pretreatment, wet oxidation, ammonia fiber/freeze explosion or expansion (AFEX), ammonia percolation (APR), dilute ammonia pretreatment, and organosolv pretreatments (See e.g., WO 2006/110891, WO 2006/11899, WO 2006/11900, and WO 2006/110901).

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs (e.g., plug-flow reactors, counter-current reactors, or continuous counter-current shrinking bed reactors) (See e.g., Duff and Murray, supra; Schell et al., Biores. Technol., 91: 179-188 [2004]; and Lee et al., Adv. Biochem. Eng. Biotechnol., 65: 93-115 [1999]).

In some embodiments, lime pretreatment is performed with calcium carbonate, sodium hydroxide, or ammonia at low temperatures of about 85° C. to about 150° C. and residence times from about 1 hour to several days (Wyman et al., Biores. Technol., 96: 1959-1966 [2005]; and Mosier et al., Biores. Technol. 96: 673-686 [2005]).

Wet oxidation is a thermal pretreatment performed typically at about 180° C. to about 200° C. for about 5 to about 15 minutes with addition of an oxidative agent such as hydrogen peroxide or over-pressure of oxygen (See e.g., Schmidt and Thomsen, Biores. Technol., 64:139-151 [1998]; Palonen et al., Appl. Biochem. Biotechnol., 117: 1-17 [2004]; Varga et al., Biotechnol. Bioeng., 88: 567-574 [2004]; Martin et al., J. Chem. Technol. Biotechnol., 81: 1669-1677 [2006]). The pretreatment is performed at preferably about 1% to about 40% dry matter, about 2 to about 30% dry matter, or about 5 to about 20% dry matter, and often the initial pH is increased by the addition of an alkali such as sodium carbonate. In some embodiments, a modification of the wet oxidation pretreatment method, known as wet explosion (combination of wet oxidation and steam explosion), finds use. This method can handle dry matter up to about 30%. In wet explosion, the oxidizing agent is introduced during pretreatment after a certain residence time. The pretreatment is then ended by flashing to atmospheric pressure (See e.g., WO 2006/032282).

In some embodiments, ammonia fiber expansion (AFEX) finds use. This method involves treating cellulosic material with liquid or gaseous ammonia at moderate temperatures such as about 90 to about 100° C. and high pressure such as about 17 to about 20 bar for about 5 to about 10 minutes, where the dry matter content can be as high as about 60% (See e.g., Gollapalli et al., Appl. Biochem. Biotechnol., 98: 23-35 [2002]; Chundawat et al., Biotechnol. Bioeng., 96:219-231 [2007]; Alizadeh et al., Appl. Biochem. Biotechnol., 121: 1133-1141 [2005]; and Teymouri et al., Biores. Technol., 96: 2014-2018 [2005]). AFEX pretreatment results in the depolymerization of cellulose and partial hydrolysis of hemicellulose. Lignin-carbohydrate complexes are cleaved. Dilute ammonia pretreatment utilizes more dilute solutions of ammonia than AFEX and may be conducted at a temperature of about 100° C. to about 150° C., or any suitable temperature therebetween (See e.g., U.S. Pat. Appln. Pub. Nos. 2007/0031918 and 2007/0037259, herein incorporated by reference in their entireties). In some embodiments, the duration of the dilute ammonia pretreatment is about 1 to about 20 minutes, or any suitable duration therebetween.

In some embodiments, organosolv pretreatment finds use. This method delignifies cellulosic material by extraction using aqueous ethanol (about 40% to about 60% ethanol) at about 160° C. to about 200° C. for about 30 to about 60 minutes (See e.g., Pan et al., Biotechnol. Bioeng., 90: 473-481 [2005]; Pan et al., Biotechnol. Bioeng., 94: 851-861 [2006]; and Kurabi et al., Appl. Biochem. Biotechnol., 121: 219-230 [2005]). Sulfuric acid is usually added as a catalyst. In organosolv pretreatment, the majority of hemicellulose is removed.

Other examples of suitable pretreatment methods are known in the art (See e.g., Schell et al., Appl. Biochem. Biotechnol., 105:69-85 [2003]; Mosier et al., Biores. Technol., 96: 673-686 [2005]; and U.S. Pat. Appln. Publ. No. 2002/0164730).

In some embodiments, the chemical pretreatment is preferably carried out as an acid treatment, and more preferably as a continuous dilute and/or mild acid treatment. The acid is typically sulfuric acid, but other acids can also be used, such as nitric acid, phosphoric acid, hydrogen chloride or mixtures thereof. Mild acid treatment is conducted in the pH range of about 1 to about 5, or about 1 to about 4, or about 1 to about 3. In some embodiments, the acid concentration is in the range of from about 0.01 to about 20 wt % acid, while in other embodiments, it is in the range of from about 0.05 to about 10 wt % acid, in other embodiments, it is in the range of from about 0.1 to about 5 wt % acid, and in still other embodiments, it is in the range of from about 0.2 to about 2.0 wt % acid. The acid is contacted with cellulosic material and held at a temperature in the range of preferably about 160° C. to about 220° C., and more preferably about 165° C. to about 195° C., for periods ranging from seconds to minutes to (e.g., about 1 second to about 60 minutes).

In some embodiments, pretreatment takes place in an aqueous slurry. In some embodiments, cellulosic material is present during pretreatment in amounts preferably between about 10 to about 80 wt %, or about 20 to about 70 wt %, or about 30 to about 60 wt %, or about 50 wt %. The pretreated cellulosic material can be unwashed or washed using any suitable method known in the art (e.g., washed with water).

Physical Pretreatment.

Physical pretreatment can involve high pressure and/or high temperature (steam explosion). In some embodiments, high pressure physical pretreatment involves pressure in the range of about 300 to about 600 psi, or about 350 to about 550 psi, or about 400 to about 500 psi, or about 450 psi. In some other embodiments, high temperature pretreatment involves the use of treatment temperatures in the range of about 100° C. to about 300° C., or about 140° C. to about 235° C. In some embodiments, mechanical pretreatment is performed in a batch-process, steam gun hydrolyzer system that uses high pressure and high temperature as defined above (e.g., Sunds Hydrolyzer; Sunds Defibrator AB, Sweden).

Combined Physical and Chemical Pretreatment.

In some embodiments, combined physical and chemical pretreatments find use. Indeed, cellulosic material can be pretreated both physically and chemically. For example, in some embodiments, the pretreatment step involves dilute or mild acid treatment and high temperature and/or pressure treatment. The physical and chemical pretreatments can be carried out sequentially or simultaneously, as desired. In some additional embodiments, mechanical pretreatment is also used in conjunction with the physical and chemical pretreatments. Thus, in some embodiments, cellulosic material is subjected to mechanical, chemical, or physical pretreatment, or any combination thereof, to promote the separation and/or release of cellulose, hemicellulose, and/or lignin.

Biological Pretreatment.

In some embodiments, biological pretreatment techniques find use. In some embodiments, these methods involve applying lignin-solubilizing microorganisms (See e.g., Hsu, in Wyman (ed.), *Handbook on Bioethanol: Production and Utilization*, Taylor & Francis, Washington, D.C., at pp. 179-212 [1996]; Ghosh and Singh, Adv. Appl. Microbiol., 39:295-333 [1993]; McMillan, in Baker and Overend (eds.), *Enzymatic Conversion of Biomass for Fuels Production*, ACS Symposium Series 566, American Chemical Society, Washington, D.C., chapter 15 [1994]; Gong et al., Adv. Biochem. Engineer. Biotechnol., 65: 207-241 [1999]; Olsson and Hahn-Hagerdal, Enz. Microb. Tech., 18:312-331 [1996]; and Vallander and Eriksson, Adv. Biochem. Eng. Biotechnol. 42: 63-95 [1990]).

In some embodiments, the soluble compounds derived from pretreatment process are subsequently separated from the solids. For example, in some embodiments, the separation step comprises one or more of standard mechanical means (e.g., screening, sieving, centrifugation or filtration) to achieve the separation. In some other embodiments, the soluble compounds are not separated from the solids following pretreatment. Those of skill in the art appreciate that pretreatment may be conducted as a batch, fed-batch or continuous process. It will also be appreciated that pretreatment may be conducted at low, medium or high solids consistency as desired (See e.g., WO2010/022511, which is incorporated herein by reference in its entirety).

Fermentation

In some embodiments, methods for generating sugar(s) described herein further comprise fermentation of the resultant sugar(s) to an end product. Fermentation involves the conversion of a sugar source to an end product through the use of a fermenting organism. Any suitable organism finds use in the present invention, including bacterial and fungal organisms (e.g., yeast and filamentous fungi), suitable for producing a desired end product. Especially suitable fermenting organisms are able to ferment (i.e., convert), sugars, such as glucose, fructose, maltose, xylose, mannose and/or arabinose, directly or indirectly into a desired end product. Examples of fermenting organisms include fungal organisms such as yeast. In some embodiments, yeast strains, including but not limited to the following genera find use: the genus *Saccharomyces* (e.g., *S. cerevisiae* and *S. uvarum*); *Pichia* (e.g., *P. stipitis* and *P. pastoris*); *Candida* (e.g., *C. utilis*, *C. arabinofermentans*, *C. diddensii*, *C. sonorensis*, *C. shehatae*,

*C. tropicalis*, and *C. boidinii*). Other fermenting organisms include, but are not limited to strains of *Zymomonas*, *Hansenula* (e.g., *H. polymorpha* and *H. anomala*), *Kluyveromyces* (e.g., *K. fragilis*), and *Schizosaccharomyces* (e.g., *S. pombe*).

In some embodiments, the fermenting organisms are strains of *Escherichia* (e.g., *E. coli*), *Zymomonas* (e.g., *Z. mobilis*), *Zymobacter* (e.g., *Z. palmae*), *Klebsiella* (e.g., *K. oxytoca*), *Leuconostoc* (e.g., *L. mesenteroides*), *Clostridium* (e.g., *C. butyricum*), *Enterobacter* (e.g., *E. aerogenes*) and *Thermoanaerobacter* (e.g., *Thermoanaerobacter* BG1L1 [See e.g., Georgieva and Ahring, Appl. Microbiol, Biotech., 77: 61-86] *T. ethanolicus*, *T thermosaccharolyticum*, or *T. mathranii*), *Lactobacillus*, *Corynebacterium glutamicum* R, *Bacillus thermoglucosidaisus*, and *Geobacillus thermoglucosidasius*. It is not intended that the fermenting organism be limited to these particular strains, as any suitable organism finds use in the present invention.

The fermentation conditions depend on the desired fermentation product and can easily be determined by one of ordinary skill in the art. In some embodiments involving ethanol fermentation by yeast, fermentation is typically ongoing for between about 1 hour to about 120 hours, or about 12 to about 96 hours. In some embodiments, the fermentation is carried out at a temperature between about 20° C. to about 40° C., or between about 26° C. and about 34° C., or about 32° C. In some embodiments, the fermentation pH is from about pH 3 to about pH 7, while in some other embodiments, the pH is about 4 to about 6.

In some embodiments, enzymatic hydrolysis and fermentation are conducted in separate vessels, so that each biological reaction can occur under its respective optimal conditions (e.g., temperature). In some other embodiments, the methods for producing glucose from cellulose are conducted simultaneously with fermentation in a simultaneous saccharification and fermentation (i.e., "SSF") reaction. In some embodiments, SSF is typically carried out at temperatures of about 28° C. to about 50° C., or about 30° C. to about 40° C., or about 35° C. to about 38° C., which is a compromise between the about 50° C. optimum for most cellulase enzyme mixtures and the about 28° C. to about 30° C. optimum for most yeast. However, it is not intended that the present invention be limited to any particular temperature, as any suitable temperature finds use in the present invention.

In some embodiments, the methods for generating glucose further comprise fermentation of the glucose to a desired end product. It is not intended that the methods provided herein be limited to the production of any specific end product. In some embodiments, end products include fuel alcohols or precursor industrial chemicals. For example, in some embodiments, fermentation products include precursor industrial chemicals such as alcohols (e.g., ethanol, methanol and/or butanol); organic acids (e.g., butyric acid, citric acid, acetic acid, itaconic acid, lactic acid, and/or gluconic acid); ketones (e.g., acetone); amino acids (e.g., glutamic acid); gases (e.g., $H_2$ and/or $CO_2$); antimicrobials (e.g., penicillin and/or tetracycline); enzymes; vitamins (e.g., riboflavin, $B_{12}$, and/or beta-carotene); and/or hormones. In some embodiments, the end product is a fuel alcohol. Suitable fuel alcohols are known in the art and include, but are not limited to lower alcohols such as methanol, ethanol, butanol and propyl alcohols.

Increased Expression of Saccharide Hydrolyzing Enzymes

In some embodiments provided herein, the fungal cell is further genetically modified to increase its production of one or more saccharide hydrolyzing enzymes. For example, in some embodiments, the fungal cell overexpresses a homologous or heterologous gene encoding a saccharide hydrolysis enzyme such as beta-glucosidase. In some embodiments, the one or more saccharide hydrolysis enzyme is a cellulase enzyme described herein. For example, in some embodiments, the enzyme is any one of a variety of endoglucanases, cellobiohydrolases, beta-glucosidases, endoxylanases, beta-xylosidases, arabinofuranosidases, alpha-glucuronidases, acetylxylan esterases, feruloyl esterases, and alpha-glucuronyl esterases, and/or any other enzyme involved in saccharide hydrolysis. In some embodiments, the fungal cell is genetically modified to increase expression of beta-glucosidase. Thus, in some embodiments, the fungal cell comprises a polynucleotide sequence for increased expression of beta-glucosidase-encoding polynucleotide. In some embodiments, the fungal cell is further genetically modified to delete polynucleotides encoding one or more endogenous cellobiose dehydrogenase enzymes.

In some embodiments, the saccharide hydrolyzing enzyme is endogenous to the fungal cell, while in other embodiments, the saccharide hydrolyzing enzyme is exogenous to the fungal cell. In some additional embodiments, the enzyme mixture further comprises a saccharide hydrolyzing enzyme that is heterologous to the fungal cell. Still further, in some embodiments, the methods for generating glucose comprise contacting cellulose with an enzyme mixture that comprises a saccharide hydrolyzing enzyme that is heterologous to the fungal cell.

In some embodiments, a fungal cell is genetically modified to increase the expression of a saccharide hydrolysis enzyme using any of a variety of suitable methods known to those of skill in the art. In some embodiments, the hydrolyzing enzyme-encoding polynucleotide sequence is adapted for increased expression in a host fungal cell. As used herein, a polynucleotide sequence that has been adapted for expression is a polynucleotide sequence that has been inserted into an expression vector or otherwise modified to contain regulatory elements necessary for expression of the polynucleotide in the host cell, positioned in such a manner as to permit expression of the polynucleotide in the host cell. Such regulatory elements required for expression include promoter sequences, transcription initiation sequences and, optionally, enhancer sequences. For example, in some embodiments, a polynucleotide sequence is inserted into a plasmid vector adapted for expression in the fungal host cell.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) (hour(s)); U (units); MW (molecular weight); rpm (rotations per minute); ° C. (degrees Centigrade); wt % (weight percent); w.r.t. (with regard to); DNA (deoxyribonucleic acid); RNA (ribonucleic acid); HPLC (high pressure liquid chromatography); MS (mass spectroscopy); LC (liquid chromatography); LC/MS (liquid chromatography/mass spectroscopy); LC/MS/MS (liquid chromatography/multi-stage mass spectroscopy); HMF (hydroxymethylfurfural); YPD (Yeast extract 10 g/L; Peptone 20 g/L; Dextrose 20 g/L); DCPIP (2,6-dichlorophenolindophenol); CV (column volume); NREL (National Renewable Energy Laboratory, Golden, Colo.); ARS (ARS Culture Collection or NRRL Culture Collection, Peoria, Ill.); Lallemand (Lallemand Ethanol Technology, Milwaukee, Wis.); Cayla (Cayla-InvivoGen, Toulouse, France); Agilent New Brunswick (New Brunswick Scientific Co., Edison, N.J.); Sigma (Sigma Aldrich, St. Louis, Mo.); Eppendorf (Eppendorf AG, Hamburg, Germany); GE Healthcare (GE Healthcare, Waukesha, Wis.); Bruker Optics (Bruker Optics, Inc., Billerica, Mass.); Specac (Specac, Inc., Cranston, R.I.); Invitrogen (Invitrogen, Corp., Carlsbad, Calif.); Alphalyse (Alphalyse, Inc., Palo Alto, Calif.); Promega (Promega, Corp., Madison, Wis.); Sartorius (Sartorius-Stedim Biotech, SA, Aubagne, France); Finnzymes (Finnzymes Oy, Espoo, FI [part of Thermo Fisher Scientific]), CalBiochem (CalBiochem, EMD Chemicals, Inc., Gibbstown, N.J.); and Bio-Rad (Bio-Rad Laboratories, Hercules, Calif.).

The following CDH sequences from *M. thermophila* (C1) find use in the present invention. SEQ ID NOS:1 and 2 provide CDH1 nucleic acid and amino acid sequences, respectively. SEQ ID NO:3 is the amino acid sequence of CDH2, while SEQ ID NO:4 is the amino acid sequence of CDH3, SEQ ID NO:5 is the amino acid sequence of CDH4, SEQ ID NO:6 is the amino acid sequence of CDH5, SEQ ID NO:7 is the amino acid sequence of CDH6, and SEQ ID NO:8 is the amino acid sequence of CDH7.

```
CDH1:
                                                                                 (SEQ ID NO: 1)
atgaggacctcctctcgtttaatcggtgcccttgcggcggcactcttgccgtctgcccttgcgcagaacaacgcgccggtaaccttcaccgaccg gactcgggcattaccttcaacacgtggggtctcgccgaggattctccccagactaagggcggtttcacttttggtgttgctctgccctctgatgccctc acgacagacgccaaggagttcatcggttacttgaaatgcgcgaggaacgatgagagcggttggtgcggtgtctccctgggcggcccatgacca actcgctcctcatcgcggcctggccccacgaggacaccgtctacacctctctccgcttcgccaccggctatgccatgccggatgtctaccaggggg acgccgagatcacccaggtctcctcctctgtcaactcgacgcacttcagcctcatcttcaggtgcgagaactgcctgcaatggagtcaaagcggc gccaccggcggtgcctccacctcgaacggcgtgttggtcctcggctgggtccaggcattcgccgaccccggcaacccgacctgccccgaccag atcaccctcgagcagcacgacaacggcatgggtatctggggtgcccagctcaactccgacgcgccagcccgtcctacaccgagtgggccgcc caggccaccaagaccgtcacgggtgactgcggcggtcccaccgagacctctgtcgtcggtgtcccgttccgacgggcgtctcgttcgattacat cgtcgtgggcggcggtgccggtggcatccccgccgccgacaagctcagcgaggccggcaagagtgtgctgctcatcgagaagggctttgcctc gaccgccaacaccggaggcactctcggccccgagtggctcgagggccacgaccttacccgctttgacgtgccgggtctgtgcaaccagatctgg gttgactccaaggggatcgcttgcgaggataccgaccagatggctggctgtgtcctcggcggcggtaccgccgtgaatgccggcctgtggttcaa gccctactcgctcgactgggactacctcttccctagtggttggaagtacaaagacgtccagccggccatcaaccgcgccctctcgcgcatcccggg caccgatgctccctcgaccgacggcaagcgctactaccaacagggcttcgacgtcctctccaagggcctggccggcggcggctggacctcggt cacggccaataacgcgccagacaagaagaaccgcaccttctcccatgcccccttcatgttcgccggcggcgagcgcaacggcccgctgggcac ctacttccagaccgccaagaagcgcagcaacttcaagctctggctcaacacgtcggtcaagcgcgtcatccgccagggcggccacatcaccggc gtcgaggtcgagccgttccgcgacggcggttaccaaggcatcgtcccccgtcaccaaggttacgggccgcgtcatcctctctgccggtacctttggc agtgcaaagatcctgctgaggagcggtatcggtccgaacgatcagctgcaggttgtcgcggcctcggagaaggatggccctaccatgatcagca actcgtcctggatcaacctgcctgtcggctacaacctggatgaccacctcaacaccgacactgtcatctcccaccccgacgtcgtgttctacgacttc tacgaggcgtgggacaatcccatccagtctgacaaggacagctacctcaactcgcgcacgggcatcctcgcccaagccgctcccaacattgggc ctatgttctgggaagagatcaagggtgcggacggcattgttcgccagctccagtggactgcccgtgtcgagggcagcctgggtgcccccaacgg caagaccatgaccatgtcgcagtacctcggtcgtggtgccacctcgcgcggccgcatgaccatcacccgtccctgacaactgtcgtctcggacgt gccctacctcaaggaccccaacgacaaggaggccgtcatccagggcatcatcaacctgcagaacgccctcaagaacgtcgccaacctgacctg gctcttccccaactcgaccatcacgccgcgccaatacgttgacagcatggtcgtctccccgagcaaccggcgctccaaccactggatgggcacca acaagatcggcaccgacgacgggcgcaagggcggctccgccgtcgtcgacctcaacaccaaggtctacggcaccgacaacctcttcgtcatcg acgcctccatcttccccggcgtgccaccaccaaccccacctcgtacatcgtgacggcgtcggagcacgcctcggcccgcatcctcgccctgccc gacctcacgcccgtccccaagtacgggcagtgcggcggccgcgaatggagcggcagcttcgtctgcgccgacggctccacgtgccagatgca gaacgagtggtactcgcagtgcttgtga
                                                                                 (SEQ ID NO: 2)
MRTSSRLIGALAAALLPSALAQNNAPVTFTDPDSGITFNTWGLAEDSPQTKGGFTFGVALPSD

ALTTDAKEFIGYLKCARNDESGWCGVSLGGPMTNSLLIAAWPHEDTVYTSLRFATGYAMPD

VYQGDAEITQVSSSVNSTHFSLIFRCENCLQWSQSGATGGASTSNGVLVLGWVQAFADPGNP

TCPDQITLEQHDNGMGIWGAQLNSDAASPSYTEWAAQATKTVTGDCGGPTETSVVGVPVPT
```

-continued

GVSFDYIVVGGGAGGIPAADKLSEAGKSVLLIEKGFASTANTGGTLGPEWLEGHDLTRFDVP

GLCNQIWVDSKGIACEDTDQMAGCVLGGGTAVNAGLWFKPYSLDWDYLFPSGWKYKDVQ

PAINRALSRIPGTDAPSTDGKRYYQQGFDVLSKGLAGGGWTSVTANNAPDKKNRTFSHAPF

MFAGGERNGPLGTYFQTAKKRSNFKLWLNTSVKRVIRQGGHITGVEVEPFRDGGYQGIVPV

TKVTGRVILSAGTFGSAKILLRSGIGPNDQLQVVAASEKDGPTMISNSSWINLPVGYNLDDHL

NTDTVISHPDVVFYDFYEAWDNPIQSDKDSYLNSRTGILAQAAPNIGPMFWEEIKGADGIVRQ

LQWTARVEGSLGAPNGKTMTMSQYLGRGATSRGRMTITPSLTTVVSDVPYLKDPNDKEAVI

QGIINLQNALKNVANLTWLFPNSTITPRQYVDSMVVSPSNRRSNHWMGTNKIGTDDGRKGG

SAVVDLNTKVYGTDNLFVIDASIFPGVPTTNPTSYIVTASEHASARILALPDLTPVPKYGQCGG

REWSGSFVCADGSTCQMQNEWYSQCL

CDH2:                                                                (SEQ ID NO: 3)

MKLLSRVGATALAATLSLQQCAAQMTEGTYTDEATGIQFKTWTASEGAPFTFGLTLPADAL

EKDATEYIGLLRCQITDPASPSWCGISHGQSGQMTQALLLVAWASEDTVYTSFRYATGYTLP

GLYTGDAKLTQISSSVSEDSFEVLFRCENCFSWDQDGTKGNVSTSNGNLVLGRAAAKDGVT

GPTCPDTAEFGFHDNGFGQWGAVLEGATSDSYEEWAKLATTTPETTCDGTGPGDKECVPAP

EDTYDYIVVGAGAGGITVADKLSEAGHKVLLIEKGPPSTGLWNGTMKPEWLESTDLTRFDVP

GLCNQIWVDSAGIACTDTDQMAGCVLGGGTAVNAGLWWKPHPADWDENFPEGWKSSDLA

DATERVFKRIPGTSHPSQDGKLYRQEGFEVISKGLANAGWKEISANEAPSEKNHTYAHTEFM

FSGGERGGPLATYLASAAERSNFNLWLNTAVRRAVRSGSKVTGVELECLTDGGFSGTVNLN

EGGGVIFSAGAFGSAKLLLRSGIGPEDQLEIVASSKDGETFTPKDEWINLPVGHNLIDHLNTDL

IITHPDVVFYDFYAAWDEPITEDKEAYLNSRSGILAQAAPNIGPMMWDQVTPSDGITRQFQW

TCRVEGDSSKTNSTHAMTLSQYLGRGVVSRGRMGITSGLSTTVAEHPYLHNNGDLEAVIQGI

QNVVDALSQVADLEWVLPPPDGTVADYVNSLIVSPANRRANHWMGTAKLGTDDGRSGGTS

VVDLDTKVYGTDNLFVVDASVFPGMSTGNPSAMIVIVAEQAAQRILALRS

CDH3:                                                                (SEQ ID NO: 4)

MKFLRKSDRGSVLGSTLFSLAFLFYSPPTAAQSPPPDGAVYDYIVIGSGPGGGVVGANLAKA

GYSVLLLEAGDDSPGAGFGVYTPTVTWDFYVKHYPEGDPRDNQYSHLTWLTPDGRYWVGQ

SGAPEGSRLLGVYYPRGATLGGSSMINAMVVWLPNDSDWDYHAEVTGDDSWRAENMHKIF

QKIEKNNYLPRGTANHGFDGWFQTQMGTMVQTNRTGPLQGNGVMTTYAQDWNLTIPMSD

LLIRDPNEIGPDRDQTSSIYGQVSHQFANGNRYSSRHYVQDAVSSGANLTVSLTSLATRILFDT

VTEPDSPRATGVEYLFGKSLYRGDRRRADGAIGVNRTAVARREVIVSGGAFNSPQLLLLSGIG

NATELEALGIPVIRDLPGVGRNLMDNQEMPIVGTSPGGGPGAVAGVAMYKTRHPAHGERD

MFLFGGPGFLFRGFWPNEAVHLPDEPAQPVYGVSMVKGSSVNNGGWVKLRSRDPTDTPEIN

FNHYAVGAEYDLEAVKDTVAWIRSVYRRVGIATVEPPCARGPDENGYCGEEDEAWIHKQTF

GHHPTSTNKIGADDDPTAVLDSKFRVRGVRALRVVDASAFARIPGVFPVVSTFMISQKASDDI

LAELEAESR

CDH4:                                                                (SEQ ID NO: 5)

MGFLAATLVSCAALASAASIPRPHAKRQVSQLRDDYDFVIVGGGTSGLTVADRLTEAFPAKN

VLVIEYGDVHYAPGTFDPPTDWITPQPDAPPSWSFNSLPNPDMANTTAFVLAGQVVGGSSAV

NGMFFDRASRHDYDAWTAVGGSGFEQSSHKWDWEGLFPFFQKSVTFTEPPADIVQKYHYT

WDLSAYGNGSTPIYSSYPVFQWADQPLLNQAWQEMGINPVTECAGGDKEGVCWVPASQHP

-continued

VTARRSHAGLGHYADVLPRANYDLLVQHQVVRVVFPNGPSHGPPLVEARSLADNHLFNVT

VKGEVIISAGALHTPTVLQRSGIGPASFLDDAGIPVTLDLPGVGANLQDHCGPPVTWNYTEPY

TGFFPLPSEMVNNATFKAEAITGFDEVPARGPYTLAGGNNAIFVSLPHLTADYGAITANIRAM

VADGTAASYLAADVRTIPGMVAGYEAQLLVLADLLDNPEAPSLETPWATSEAPQTSSVLAFL

LHPLSRGSVRLNLSDPLAQPVLDYRSGSNPVDIDLHLAHVRFLRGLLDTPTMQARGALETAP

GSAVADSDEALGEYVRSHSTLSFMHPCCTAAMLPEDRGGVVGPDLKVHGAEGLRVVDMSV

MPLLPGAHLSATAYAVGEKAADIIIQEWMDKEQ

CDH5: (SEQ ID NO: 6)

MELLRVSLAAVALSPLILFGVAAAHPTARSIARSTILDGADGLLPEYDYIIIGGGTSGLTVADR

LTENRKRKFSRSPLPTSPARSSPAWCYSVLVLERGIFQNSSSVTTISGGSRGLFDPSLTFNINSV

PQAGLDNRSIAVIGGLILGGSSGVNGLQVLRGQREDYDRWGSYFGPNSDWSWKGLLPYFKK

AWNFHPPRPELVSQFDIKYDPSYWGNTSDVHASFPTTFWPVLKLEMAAFGDIPGVEYPPDSA

SGETGAYWHPASVDPATVLRSFARPAHWDNIEAARPNYHTLTGQRVLKVAFDGNRATSVVF

VPANATDHSTARSVKAKKEIVLAAGAIHTPQILQASGVGPKQVLKEAGVPLVVDAPGVGSNF

QDQPYVVAPTFNFTKFPFHPDFYDMILNQTFIAEAQAQFEKDRTGPHTIASGYCGSWLPLQIIA

PNSWKDIARRYESQDPAAYLPAGTDETVIEGYRAQQKALARSMRSKQSAMYNFFLRGGYEE

GSVVYLHPTSRGTVRINRSDPFFSPPEVDYRALSNPTDLEVLLEFTPFTRRYFLETRLKSLDPV

ELSPGANVTAPADIEAWLRSVMIPSSFHPIGTAAMLPRHLGGVVDENLLVYGVEGLSVVDAS

VMPDLPGSYTQQTVYAIAEKAADLIKSRA

CDH6: (SEQ ID NO: 7)

MQVASKLVAVTGGALALWLHPVAAQEGCTNISSTETYDYIVVGSGAGGIPVADRLSEAGHK

VLLIEKGPPSTGRWGGIMKPEWLIGTNLTRFDVPGLCNQIWADPTGAICTDVDQMAGCMLG

GGTAVNAGLWWKPHPADWDVNFPEGWHSEDMAEATERVFERIPGTITPSMDGKRYLSQGF

DMLGGSLEAAGWEYLVPNEHPDRKNRTYGHSTFMYSGGERGGPLATYLVSAVQREGFTLW

MNTTVTRIIREGGHATGVEVQCSNSEAGQAGIVPLTPKTGRVIVSAGAFGSAKLLFRSGIGPK

DQLNIVKNSTDGPSMISEDQWIELPVGYNLNDHVGTDIEIAHPDVVFYDYYGAWDEPIVEDT

ERYVANRTGPLAQAAPNIGPIFWETIKGSDGVSRHLQWQARVEGKLNTSMTITQYLGTGSRS

RGRMTITRRLNTVVSTPPYLRDEYDREAVIQGIANLRESLKGVANLTWITPPSNVTVEDFVDS

IPATPARRCSNHWIGTAKIGLDDGREGGTSVVDLNTKVYGTDNIFVVDASIFPGHITGNPSAAI

VIAAEYAAAKILALPAPEDAAS

CDH7: (SEQ ID NO: 8)

MASVDLDQPFDYIVVGGGTAGLVVANRLSEDSNVRVLVVEAGADRNADPLVLTPGLVAGL

YGKDEYDWNFSSPPQPTLNNRRINQARGKMLGGTSGLNFMMLLYPSKGNIDSWAALGNPS

WNYDALAPYLRKFATVHPSPQSARDLLGLTYIDESLAAGDGPIQVSHTDGHNVTNKAWLET

FASLGLEVSTDPRDGKALGAFQNHASIDPATHTRSFAGPAYYTPDVAKRPNLVVLTETLVAR

VLFDTAGGEGDAVATGVEIITKDGQKKQVSACGEVILAAGALQSPQILELSGVGGRELLEKH

NIPVVVDNPNVGEHVQDHPIVCQSFEVADGVPSGDVLRDPNVLQAVVGMYQSGGGAGPLG

QSVISVAYTPLVDGSGVVSAEAKAELLARHESSFSTAEGKVLRDLVESPSEATFEFLLFPSQV

DIPENPTSMAQYITPVLPENYISVMTFIHQPFSRGKVHITSPDIRAAPLWDPRYNSDPLDLELLA

RGVQFVERIVDSATPFGRVLKQGGKRQPPLRADDLETAREIVRQRQISVFHVSGSCTMRPRD

QGGVVDERLRVYGTRGLRVVDASVFPIEPVGNIQSVVYAVAERAADLIKEDRAKA

Example 1

Fungal Strains and Methods

This Example describes the production of variants of fungal strain C1.

Strain Nomenclature

Strain CF-200 (UV18#100fΔalp1) is a derivative C1 strain. Strain CF-400 is a derivative of C1 strain ("UV18#100fΔalp1Δpyr5"), further modified by deletion of cdh1, wherein cdh1 comprises the polynucleotide sequence of SEQ ID NO:1. Cellulolytic enzymes from these strains were produced by submerged liquid culture fermentation using methods and a suitable fungal growth medium, as well-known in the art.

GOPOD Assay

The GOPOD assay kits (Sigma-Aldrich) used in these experiments to measure the amount of glucose produced. In these experiments, 10 ul of test sample was added to 190 ul of the GOPOD assay mix provided in the kit. The reaction was allowed to shake for 30 min at 50° C. Absorbance of the solution was measured at 510 nm to determine the amount of glucose produced. The glucose concentration of the samples was calculated in comparison with the glucose standards (0-150 g/L).

Example 2

Purification of C1 CDH1

In this Example, 400 mL of C1 supernatant produced using the methods of Example 1 were first concentrated to 140 mL using a rotary evaporator. Then, 63 mL of the concentrate was buffer-exchanged into 20 mM MOPS buffer, pH 7.0, using 4 in-line Hi-Prep 26/10 desalting columns (GE Healthcare, 17-5087-02). The resulting buffer-exchanged supernatant (~150 g/L total protein) was loaded onto a column containing 500 mL DEAE Fast Flow resin (GE Healthcare, 17-0709-01) pre-equilibrated with 20 mM pH7.0 MOPS buffer. The column was rinsed with 1 column volume (CV) of 20 mM MOPS (pH7.0) and then a 0-300 mM sodium chloride gradient was run over 12 column volumes. Fractions were collected and analyzed by NuPage® Novex® Bis-tris SDS-PAGE gels (Invitrogen, NP0322BOX). The SDS-PAGE bands corresponding to the apparent molecular weight of CDH1 were analyzed by MS (performed by Alphalyse). The mass-mapping analysis confirmed the presence of CDH1 in late-eluting fractions. Fractions containing CDH1, as demonstrated by SDS-PAGE gel, and confirmed by MS were pooled and concentrated by ultrafiltration using Sartorius centrifugal 10 kDa filter (Sartorius-Stedim, VS2002). Then, 10 mL 500 mM piperazine (pH 5.6) and 45 mL saturated ammonium sulfate were added to 45 mL of the CDH1-containing pool and the resulting mixture was loaded onto a Phenyl FF (high sub) 16/10 column (GE Healthcare, 28-9365-45) pre-equilibrated with 1.6M ammonium sulfate in 50 mM piperazine, pH 5.6. A gradient of 1.6 M to 0 M ammonium sulfate in 50 mM piperazine, pH 5.6, was run over 30 CV. Fractions were collected and SDS-PAGE gel analysis was performed on the selected fractions as described above, revealing that CDH1 eluted in the final rinse step with approximately 80-90% purity.

CDH1 activity was measured using a DCPIP reduction assay similar to that described by Schou et. al. (See, Schou et al., Biochem J., 330:565-71 [1998]). In a UV-transparent flat-bottom 96-well plate, 50 μL CDH1-containing fractions were added to 150 μL of a solution of 1.0 g/L cellobiose and 100 μM DCPIP in 100 mM sodium acetate, pH 5.0. Samples were agitated briefly at room temperature and then the absorbance at 530 nm ($A_{530}$) was measured for 10 minutes. C1-CDH1-containing fractions displayed a rapid drop in absorbance at 530 nm. DCPIP assays were performed using varying amounts of glucose or cellobiose with purified CDH1. Serial dilutions of cellobiose (1.0 g/L to 7.8 mg/L) and glucose (10 g/L to 78 mg/L) were prepared in a 96-well shallow-well plate. Then, 20 μL glucose and cellobiose standards were added to 160 μL/well 200 mM DCPIP (in 100 mM pH 5.0 sodium acetate). Reactions were initiated by addition of 20 μL CDH1 solution. Absorbance at 530 nm was monitored for 30 minutes. Comparisons of the rates of decrease in absorbance at 530 nm indicate that C1-CDH1 is approximately 10-fold more active on cellobiose than glucose.

Example 3

Making of CDH1 Split Marker Deletion Constructs

Genomic DNA was isolated from the C1 strain using standard procedures. Briefly, hyphal inoculum was seeded into a growth medium and allowed to grow for 72 hours at 35° C. The mycelial mat was collected by centrifugation, washed, and 50 μL DNA extraction buffer (200 mM TRIS, pH 8.0; 250 mM NaCl; 125 mM EDTA; 0.5% SDS) was added. The mycelia were ground with a conical grinder, re-extracted with 250 μL extraction buffer, and the suspension was centrifuged. The supernatant was transferred to a new tube containing 300 μL isopropanol. DNA was collected by centrifugation, washed twice with 70% ethanol, and diluted in 100 μL of water.

Genomic DNA fragments flanking the cdh1 gene were cloned using primers cf09067 and cf09068 (cdh1 upstream homology) and primers cf09069 and cf09070 (cdh1 downstream homology). PCR reactions were performed by using the GoTaq® polymerase (Promega) following the manufacturer's instructions using 0.2 uM of each primer. The amplification conditions were 95° C. for 2 minutes, 35 cycles of 95° C. for 30 seconds, 55° C. for 30 seconds (for upstream homology) or 53° C. for 30 seconds (for downstream homology), 72° C. for 1 minute and final extension at 72° C. for 5 minutes. The pyr5 gene was PCR amplified as a split marker from a vector using primers cf09024 and cf09025 (for the 5' portion of the gene) and cf09026 and cf09027 (for the 3' portion of the gene). PCR reactions were performed using the GoTaq® polymerase (Promega) following the manufacturer's instructions using 0.2 uM of each primer. The amplification conditions were 95° C. for 2 minutes, 35 cycles of 95° C. for 30 seconds, 53° C. for 30 seconds, 72° C. for 1 minute and final extension at 72° C. for 5 minutes. The primers used are shown in Table 3-1. In separate strand overlap extension reactions (See, Horton et al., Meth. Enzymol., 217:270-279 [1993]), the PCR products resulting from primers cf09067 and cf09068 and primers cf09026 and cf09027 were fused, as were the PCR products resulting from primers cf09069 and cf09070, and primers cf09024 and cf09025. PCR reactions were performed by using Finnzymes' Phusion® DNA polymerase following the manufacturer's instructions including 3% DMSO and using 0.2 uM of each primer. The amplification conditions were 98° C. for 1 minute, 35 cycles of 98° C. for 10 seconds, 62° C. for 20 seconds, 72° C. for 2 minutes and final extension at 72° C. for 5 minutes. The strand overlap extension products were used for cdh1 deletion.

TABLE 3-1

Primer Names and Sequences

| Primer Name | Sequence(5'-3') | SEQ ID NO: |
|---|---|---|
| cf09067 | CACGCGGGGTTCTTTCTCCATCTC | 9 |
| cf09068 | TGAGGAAAACGCCGAGACTGAGCTCGACTCTGCCGG CCTACCTACGA | 10 |
| cf09069 | ATCAGTTGGGTGCACGAGTGGGTTTTGATGGGGAGT TGAGTTTGTGAA | 11 |
| cf09070 | GGATGGATGAGGTTGTTTTTGAGC | 12 |
| cf09024 | AACCCACTCGTGCACCCAACTGAT | 13 |
| cf09025 | GACCACGATGCCGGCTACGATACC | 14 |
| cf09026 | ACATGGCCCCACTCGCTTCTTACA | 15 |

Example 4

Transformation Method

C1 cells and derivative strains were inoculated into 100 mL growth medium in a 500 mL Erlenmeyer flask using $10^6$ spores/mL. The culture was incubated for 48 hours at 35° C., 250 rpm. To harvest the mycelia, the culture was filtered over a sterile Myracloth filter (CalBiochem) and washed with 100 mL 1700 mosmol NaCl/CaCl$_2$ solution (0.6 M NaCl, 0.27 M CaCl$_2$*H$_2$O). The washed mycelia were transferred into a 50 mL tube and weighed. Caylase (20 mg/gram mycelia; Cayla) was dissolved in 1700 mosmol NaCl/CaCl$_2$ and UV-sterilized for 90 sec. Then, 3 mL of sterile Caylase solution was added into the tube containing washed mycelia and mixed. Then, 15 mL of 1700 mosmol NaCl/CaCl$_2$ solution was added into the tube and mixed. The mycelium/Caylase suspension was incubated at 30° C., 70 rpm for 2 hours. Protoplasts were harvested by filtering through a sterile Myracloth filter into a sterile 50 mL tube. 25 mL cold STC (1.2 M sorbitol, 50 mM CaCl$_2$*H$_2$O, 35 mM NaCl, 10 mM Tris-HCl) was added to the flow through and spun down at 2720 rpm for 10 min at 4° C. The pellet was resuspended in 50 mL STC and centrifuged again. After the washing steps, the pellet was resuspended in 1 mL STC.

Then, 2 µg DNA of each strand overlap extension product was pipetted into the bottom of a 15 mL sterile tube and 1 µL aurintricarboxylic acid and 100 µL of the protoplast suspension were added. The contents were mixed and the protoplasts were incubated with the DNA at room temperature for 25 min. Then, 1.7 mL PEG4000 solution (60% PEG4000; polyethylene glycol, average molecular weight 4000 daltons), 50 mM CaCl$_2$.H$_2$O, 35 mM NaCl, 10 mM Tris-HCl) was added and mixed thoroughly. The solution was kept at room temperature for 20 min. The tube was filled with STC, mixed and centrifuged at 2500 rpm for 10 min at 4° C. The STC was poured off and the pellet was resuspended in the remaining STC and plated on minimal selective media plates. The plates were incubated for 5 days at 35° C. Colonies were restreaked and checked for the deletion of cdh1; colonies with this deletion were designated as strain "CF-400".

Example 5

Confirmation of CDH1 Deletion

Genomic DNA was prepared as described in Example 3. PCR reactions were performed by using the GoTaq® polymerase (Promega) following the manufacturer's instructions using 0.2 uM of each primer (primers cf09112 and cf09113). The amplification conditions were 95° C. for 2 minutes, 35 cycles of 95° C. for 30 seconds, 54° C. for 30 seconds, 72° C. for 30 seconds and final extension at 72° C. for 5 minutes. PCR was also conducted using primers cf09110 and cf09111 and GoTaq® polymerase (Promega) following the manufacturer's instructions using 0.2 uM of each primer. The amplification conditions were 95° C. for 2 minutes, 35 cycles of 95° C. for 30 seconds, 55.4° C. for 30 seconds, 72° C. for 30 seconds and final extension at 72° C. for 5 minutes). These primers were used in separate PCR reactions to confirm absence of the cdh1 gene. Primers cf09181 and cf09091 were used in PCR to confirm proper junction structure and targeting of the pyr5 marker construct (See, Table 5-1). The PCR reaction was performed by using the GoTaq® polymerase (Promega) following the manufacturer's instructions using 0.2 uM of each primer. The amplification conditions were 95° C. for 2 minutes, 35 cycles of 95° C. for 30 seconds, 54.4° C. for 30 seconds, 72° C. for 3 minutes 30 seconds, and final extension at 72° C. for 5 minutes. PCR products were run on an agarose gel to confirm a banding pattern indicative of cdh1 deletion.

TABLE 5-1

Primer Names and Sequences

| Primer name | Sequence(5'-3') | SEQ ID NO: |
|---|---|---|
| cf09110 | AAGCGTGCCGATTTTCCTGATTTC | 16 |
| cf09111 | GCATTTCTGGGGCGGTTAGCA | 17 |
| cf09112 | TCATCGACGCCTCCATCTTCC | 18 |
| cf09113 | TTTCGGTTGTCGTGTTTCCATTAT | 19 |
| cf09181 | GGAGATCCTGGAGGATTTCC | 20 |
| cf09091 | CAGGCGGTGTGCGTTATCAAAA | 21 |

A colorimetric dichlorophenolindophenol (DCPIP) assay was used to test for deletion of cdh1 in CF-400. Deletion of cdh1 was determined by observing a decreased ability to reduce the DCPIP substrate compared to a parent strain. Cells of the parental C1 strain and putative cdh1 delete strain were grown and the supernatants tested for DCPIP activity. In these tests, 160 µL of freshly made DCPIP reagent solution (0.2 mM DCPIP in 100 mM sodium acetate, pH 5.0), 20 µL cellobiose solution (1 g/L cellobiose in deionized water), and 20 mLs of undiluted cell supernatant were combined in microtiter plates. The absorbance of the solution was immediately measured over time at 530 nm in kinetic mode for 30 minutes to track loss of absorbance as a result of DCPIP reduction. Supernatant from strains displaying decreased ability to reduce the DCPIP substrate were run on SDS-PAGE to confirm the absence of CDH1. Proteins from culture supernatants of submerged liquid culture fermentations of CF-400 and the untransformed parent were separated by SDS-PAGE using standard protocols. The proteins were visualized by staining with Simply Blue Safe Stain (Invitrogen), as per manufacturer's instructions. The Cdh1 protein was observed as a ~90 kD band in the untransformed parent but was absent in CF-400.

Example 6

Hydrolysis of Corn Stover

In these experiments, acid pretreated corn stover (NREL) was pH adjusted to 5.0 with aqueous ammonium hydroxide. The material was 41.3% solids, with a moisture content of 58.7%. The glucan content in the solids was 40.7%. The acid pretreated corn stover was loaded into a 96-well plate and diluted with sodium acetate buffer to an average volume of 110 μL per well with 128 mM sodium acetate, at pH 5. The total solids loading were 24.7% in all experiments, and the concentration of glucan was 100 g glucan/kg reaction. CF-200 and CF-400 enzyme supernatants were used at 3 g cellulase/kg reaction. A set of wells in the 96-well plate was also run wherein water was used in place of enzyme to serve as a control, due to the presence of free glucose in the substrate. The level of this control was subtracted from the final measured glucose concentration. The plate was sealed once all reaction components were added and placed in a shaker at 55° C. rotating at 950 rpm for 73 hours. At the end of reaction, the plate was allowed to cool. Samples were withdrawn, diluted and subsequently analyzed by GO assay kit (Sigma) to determine glucose production. The results are provided in FIG. 2. As indicated, the CF-200 supernatant generated 52.1 g/L glucose, while CF-400 supernatant generated 69.4 g/L glucose. CF-400 supernatant exhibited higher saccharification performance, indicating that deletion of cdh1 gene reduces formation of the gluconate from glucose during the saccharification reaction.

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of this invention.

What is claimed is:

1. A *Myceliophthora thermophila* fungal cell that has been genetically modified to reduce the amount of endogenous cellobiose dehydrogenase I activity that is secreted by the cell, wherein said cell comprises a deletion in the cellobiose dehydrogenase 1 (cdh1) gene set forth in SEQ ID NO:1.

2. The *Myceliophthora thermophila* fungal cell of claim 1, wherein said fungal cell has been genetically modified to disrupt the secretion signal peptide of the cellobiose dehydrogenase I.

3. The *Myceliophthora thermophila* fungal cell of claim 1, wherein said fungal cell has been genetically modified to reduce the amount of the endogenous cellobiose dehydrogenase I expressed by the cell.

4. The *Myceliophthora thermophila* fungal cell of claim 1, wherein said fungal cell has been genetically modified to disrupt a translation initiation sequence in the transcript encoding the endogenous cellobiose dehydrogenase I.

5. The *Myceliophthora thermophila* fungal cell of claim 1, wherein said fungal cell has been genetically modified to introduce a frameshift mutation in the transcript encoding the endogenous cellobiose dehydrogenase I.

6. The *Myceliophthora thermophila* fungal cell of claim 1, wherein said fungal cell has been genetically modified to reduce the transcription level of a gene encoding the endogenous cellobiose dehydrogenase I.

7. The *Myceliophthora thermophila* fungal cell of claim 6, wherein said fungal cell has been genetically modified to disrupt the promoter of a gene encoding endogenous cellobiose dehydrogenase I.

8. The *Myceliophthora thermophila* fungal cell of claim 1, wherein said fungal cell has been genetically modified to at least partially delete a gene encoding endogenous cellobiose dehydrogenase I.

9. The *Myceliophthora thermophila* fungal cell of claim 1, wherein said fungal cell has been genetically modified to reduce the catalytic efficiency of the endogenous cellobiose dehydrogenase I.

10. The *Myceliophthora thermophila* fungal cell of claim 9, wherein one or more residues in an active site of the cellobiose dehydrogenase I of said fungal cell has been genetically modified.

11. The *Myceliophthora thermophila* fungal cell of claim 10, wherein one or more residues in a heme binding domain of the cellobiose dehydrogenase I of said fungal cell have been genetically modified.

12. The *Myceliophthora thermophila* fungal cell of claim 1, wherein said cellobiose dehydrogenase I comprises an amino acid sequence that is at least about 85%, about 88%, about 90%, about 93%, about 95%, about 97%, about 98%, or about 99% identical to SEQ ID NO:2.

13. The *Myceliophthora thermophila* fungal cell of claim 1, further comprising a cellulose degrading enzyme that is homologous or heterologous to said fungal cell.

14. A fermentation medium comprising the *Myceliophthora thermophila* fungal cell of claim 1.

* * * * *